United States Patent [19]
Abelman et al.

[11] Patent Number: 5,670,479
[45] Date of Patent: Sep. 23, 1997

[54] α-KETOAMIDE DERIVATIVES AS INHIBITORS OF THROMBOSIS

[75] Inventors: Matthew M. Abelman, Solana Beach, Calif.; Daniel A. Pearson, Bedford, N.H.; George P. Vlasuk, Carlsbad; Thomas R. Webb, Encinitas, both of Calif.

[73] Assignee: Corvas International, Inc., San Diego, Calif.

[21] Appl. No.: 218,329

[22] Filed: Mar. 25, 1994

Related U.S. Application Data

[63] Continuation-in-part of Ser. No. 37,574, Mar. 25, 1993.
[51] Int. Cl.$^6$ .............................. A61K 38/00; C07K 5/00; C07K 7/00; C07K 17/00
[52] U.S. Cl. ............................ 514/12; 514/13; 530/324; 530/325; 530/326; 424/1.69; 424/9.341
[58] Field of Search ............... 514/12–13; 530/324–326; 424/1.69, 9.341

[56] References Cited

U.S. PATENT DOCUMENTS

| | | |
|---|---|---|
| 4,418,052 | 11/1983 | Wong ........................................ 424/1.69 |
| 4,652,440 | 3/1987 | Paik et al. . |
| 4,957,939 | 9/1990 | Gries et al. ............................. 514/492 |
| 4,980,148 | 12/1990 | Dean et al. . |
| 5,011,686 | 4/1991 | Pang ........................................ 424/94.1 |
| 5,024,829 | 6/1991 | Berger et al. ......................... 424/1.49 |
| 5,051,405 | 9/1991 | Klein et al. ............................ 514/18 |
| 5,053,392 | 10/1991 | Klein et al. ............................ 514/18 |
| 5,118,790 | 6/1992 | Winant et al. ......................... 530/324 |
| 5,196,404 | 3/1993 | Maraganore et al. .................. 514/13 |
| 5,240,913 | 8/1993 | Maraganore et al. .................. 514/13 |

FOREIGN PATENT DOCUMENTS

| | | |
|---|---|---|
| 0293881 | 12/1988 | European Pat. Off. . |
| 0372503 | 6/1990 | European Pat. Off. . |
| 0468339 | 1/1992 | European Pat. Off. . |
| 9101142 | 2/1991 | WIPO . |
| 9102750 | 3/1991 | WIPO . |
| 9119734 | 12/1991 | WIPO . |
| 9212140 | 7/1992 | WIPO . |
| 9314779 | 8/1993 | WIPO . |

OTHER PUBLICATIONS

Boudron et al., *FEBS Letters*, 294(3):163–166 (Dec. 1991).
DiMaio, et al., *J. Med. Chem.*, 35:3331–3341 (1992).
Fischman et al., *J. Nucl. Med.*, 34(12):2253–2263 (Dec. 1993).
Angelastro et al., "α–Diketone and α–Keto Ester Derivatives of N–Protected Amino Acids and Peptides as Novel Inhibitors of Cysteine and Serine Proteinases," *J. Med. Chem.* 33:11–13 (1990).
Bajusz et al., "Highly Active and Selective Anticoagulants: $_D$–Phe–Pro–Arg–H, a Free Tripeptide Aldehyde Prone to Spontaneous Inactivation, and Its Stable N–Methyl Derivative, $_D$–MePhe–Pro–Arg–H", *J. Med. Chem.* 33:1729–1735 (1990).
Bajusz, "Interaction of Trypsin–Like Enzymes with Small Inhibitors", *Symposia Biologica Hungarica* 25:277–298 (1984).
Bajusz et al., "Inhibition of Thrombin and Trypsin by Tripeptide Aldehydes," *Int. J. Peptide Protein Res.* 12:217–221 (1978).
Berndt and Phillips, "Platelet Membrane Proteins: Composition and Receptor Function," *Platelets in Biology and Pathology*–2, pp. 43–75, Elsevier/North Holland Biomedica Press (1981).
Bourdon et al., "Structure–function relationships of hirulog peptide interactions with thrombin," *FEBS* 294:163–166 (1991).
Brechbiel et al., "Synthesis of 1–p–Isothiocyanatobenzyl) Derivatives of DTPA and EDTA. Antibody Labeling and Tumor Imaging Studies," *Inorg. Chem.* 25:2772–2781 (1986).
Brown et al., "Conjugation of Methallothionein to a Murine Monoclonal Antibody," *Analytical Biochemistry* 172:22–28 (1988).
Califf et al., "Research After Coronary Angioplasty: An Overview," *J. Am. Coll. Cardiol.* 17:2B–13B (1991).
Chen and Buchanan, "Mitogenic Activity of Blood Components. I. Thrombin and Prothrombin (Chick Embryo Fibroblasts/Growth Factors in Plasma and Serum/Wound Healing)," *Proc. Natl. Acad. Sci. USA* 72:131–135 (1975).
Church et al., "Chimeric Antithrombin Peptide," *The Journal of Biological Chemistry* 226:11975–11979 (1991).
Connolly et al.,. "An Inhibitor of Collagen–Simulated Platelet Activation from the Salivary Glands of the *Haementeria officinalis* Leech," *J. Biol. Chem.* 267:6893–6898 (1992).
DeRoos et al., "Myocardial infarct sizing and assessment of reperfusion by magnetic resonance imaging: a review," *Int. J. Card. Imaging* 7:133–138 (1991).
Dixon, "The Graphical Determination of $K_m$ and $K_i$," *Biochem J.* 129:197–202 (1972).

(List continued on next page.)

*Primary Examiner*—Toni R. Scheiner
*Assistant Examiner*—Sheela J. Huff
*Attorney, Agent, or Firm*—Lyon & Lyon LLP

[57] ABSTRACT a-Ketoamide derivatives, their pharmaceutically acceptable salts, compositions, diagnostic compositions and pharmaceutical compositions, which are useful for preventing or treating in a mammal a pathological condition characterized by thrombosis are described.

a-Ketoamide derivatives, their pharmaceutically acceptable salts, compositions and diagnostic compositions, which are useful for in vivo imaging of thrombi in a mammal are also described.

Methods of preventing or treating in a mammal a pathological condition characterized by thrombosis and methods of in vivo imaging of thrombi in a mammal are also disclosed.

60 Claims, 10 Drawing Sheets

OTHER PUBLICATIONS

Edwards et al., "Design, Synthesis, and Kinetic Evaluation of a Unique Class of Elastase Inhibitors, the Peptidyl α-Ketobenzoxazoles, and the X-Ray Crystal Structure of the Covalent Complex Between Porcine Pancreatic Elastase and Ac-Ala-Pro-Val-2-Benzoxazole," *J. Am. Chem. Soc.* 114:1854–1863 (1992).

Eidt et al., "Thrombin is an Important Mediator of Platelet Aggregation in Stenosed Canine Coronary Arteries with Endothelial Injury," *J. Clin. Invest.* 84:18–27 (1989).

Fehrentz and Castro, "An Efficient Synthesis of Optically Active α-(t-Butoxycarbonylamino)-aldehydes from α-Amino Acids," *Synthesis* 7:676–678 (1983).

Fusetani and Matsunaga, "Cyclotheonamides, Potent Thrombin Inhibitors, From a Marine Sponge Theonella sp," *J. Am. Chem. Soc.* 112:7053–7054 (1990).

Gash et al., "Factors Influencing Reocclusion After Coronary Thrombolysis for Acute Myocardial Infarction," *Am. J. Cardiol.* 57:175–177 (1986).

Haghiara and Schreiber, "Reassignment of Stereochemistry and Total Synthesis of the Thrombin Inhibitor Cyclotheonamide B," *J. Am. Chem. Soc.* 114:6570–6571 (1992).

Hladovec, "A Sensitive Model of Venous Thrombosis in Rats," *Thrombosis Research* 43:539–544 (1986).

Houghten, "General Method for the Rapid Solid-Phase Synthesis of Large Numbers of Peptides: Specificity of Antigen-Antibody Interaction at the Level of Individual Amino Acids," *Proc. Natl. Acad. Sci. USA* 82:5131–5135 (1985).

Jakubowski and Maraganore, "Inhibition of Coagulation and Thrombin-Induced Platelet Activities by a Synthetic Dodecapeptide Modeled on the Carboxy-Terminus of Hirudin," *Blood* 75:399–406 (1990).

Jang et al., "In Vivo Thrombin Inhibition Enhances and Sustains Arterial Recanalization With Recombinant Tissue-Type Plasminogen Activator," *Cir. Res.* 67:1552–1561 (1990).

Jang et al., "Prevention of Platelet-Rich Arterial Thrombosis by Selective Thrombin Inhibition," *Circulation* 81:219–225 (1990).

Kelly et al., "Hirudin Interruption of Heparin-Resistant Arterial Thrombus Formation in Baboons," *Blood* 77:1006–1012 (1991).

Kelly et al., "Relative Antithrombotic Potencies and Hemostatic Risks of Reversible D-Phe-Pro-Arg (D-FPR) Antithrombin Derivatives," *Thromb. Haemostas.* 65:736 at abstract 257 (1991).

Kettner et al., "The Selective Inhibition of Thrombin by Peptides of Boroarginine," *J. Biol. Chem.* 265:18289–18297 (1990).

Kettner and Shaw, "Inactivation of Trypsin-Like Enzymes with Peptides of Arginine Chloromethyl Ketone," *Methods Enzymol.* 80:826–842 (1987).

Khaw et al., "Myocardial Infarct Imaging of Antibodies to Canine Cardiac Myosin with Indium-111-Diethylenetriamine Pentaacetic Acid," *Science* 209:295–297 (1980).

Kline et al., "Hirulog Peptides with Scissile bond Replacements Resistant to Thrombin Cleavage," *Biochem. Biophys. Res. Commun.* 177:1049–1055 (1991).

Krstenansky et al., "Development of MDL 28,050, a Small Stable Antithrombin Agent Based on a Functional Domain of the Leech Protein, Hirudin," *Thrombosis and Haemostasis* 63:208–214 (1990).

Krstenansky and Mao, "Antithrombin Properties of C-Terminus of Hirudin Using Synthetic Unsulfated $N^\alpha$-acetyl-hirudin$_{45-65}$," *FEBS Lett* 211:10–16 (1987).

Kurz et al., "Rat Model of Arterial Thrombosis Induced by Ferric Chloride," *Thrombosis Research* 60:269–280 (1990).

Levin et al., "Specificity of the Thrombin-Induced Release of Tissue Plasminogen Activator From Cultured Human Endothelial Cells," *Thromb. Haemostas.* 56:115–119 (1986).

Liu et al., "The Region of the Thrombin Receptor Resembling Hirudin Binds to Thrombin and Alters Enzyme Specificity," *J. Biol. Chem.* 266:16977–16980 (1991).

Lorand and Konishi, "Activation of the Fibrin Stabilizing Factor of Plasma by Thrombin," *Arch. Biochem. Biophys.* 105:58–67 (1964).

Mann et al., "Surface-Dependent Reactions of Vitamin K-Dependent Enzyme Complexes," *Blood* 76:1–16 (1990).

Mao et al., "Interaction of Hirudin with Thrombin: Identification of a Minimal Binding Domain of Hirudin That Inhibits Cloning Activity," *Biochemistry* 27:8170–8173 (1988).

Maraganore et al., "Anticoagulant Activity of Synthetic Hirudin Peptides," *J. Biol. Chem.* 264:8692–8698 (1989).

Maraganore et al., "Design and Characterization of Hirulogs: A Novel Class of Bivalent Peptide Inhibitorsr of Thrombin," *Biochemistry* 29:7095–7101 (1990).

Maraganore et al., "Comparison of Anticoagulant and Antithrombotic Activities of Hirulog-1 and Argatroban (MD-805)," *Thromb. Haemostas.* 65:651 at abstract 17 (1991).

Marki et al., "Total Solid-Phase Synthesis of Porcine Gut Gastrin Releasing Peptide (GRP), a Mammalian Bombesin," *J. Am. Chem. Soc.* 103:3178–3185 (1981).

Marki and Wallis, "The Anticoagulant of Antithrombiotic Properties of Hirudins," *Thrombosis and Haemostasis* 64:344–348 (1990).

Markwardt et al.,"Pharmacological Survey of Recombinant Hirudin," *Pharmazie* 43:202–207 (1988).

Meares et al.,"Conjugation of Antibodies with Bifunctional Chelating Agents: Isothiocyanate and Bromoacetamide Reagents, Methods of Analysis, and Subsequent Addition of Metal Ions," *Analytical Biochemistry* 142:68–78 (1984).

Mehdi et al., "The Inhibition of Human Neutrophil Elastase and Cathepsin G by Peptidyl 1,2-Dicarbonyl Derivatives," *Biochem. Biophys. Res. Commun.* 166:595–600 (1990).

Merrifield, "Solid Phase Peptide Synthesis," *Advances in Enzymology*, pp. 221–296, Nord ed., Interscience Publishers, New York, (1969).

Merrifield, "Solid Phase Peptide Synthesis: I. The Synthesis of a Tetrapeptide," *J. Am. Chem. Soc.* 85:2149–2154 (1963).

Merrifield, "Automated Synthesis of Peptides," *Science* 150:178–185 (1965).

Merrifield, "Solid Phase Synthesis," *Science* 232:341–347 (1986).

Morelock and Tolman, "Methallothionen: A Bifuncational Chelator for the Radiolabeling of Biologically Active Molecules," *Metallothione II*, Kagi and Kojima eds, pp. 247–253, Birkhauser Verlag and Basel, Boston (1987).

Morrison, "Kinetics of the Reversible Inhibition of Enzyme-Catalysed Reactions by Tight-Binding Inhibitors," *Biochem. Biophys. Acta* 185:269–287 (1969).

Musci et al., "Evidence for Multiple Conformational Changes in the Active Center of Thrombin Induced by Complex Formation with Thrombomodulin: An Analysis Employing Nitroxide Spin–Labels," *Biochemistry* 27:769–773 (1988).

Nagai et al., "Poststatin, a New Inhibitor of Prolyl Endopeptidase, Produced by *Streptomyces Viridochromogenes* MH534–30F3, II. Structure Determination and Inhibitory Actions," *J. Antibiotics* 44:956–961 (1991).

Nakahara et al., "Preparation of Tyrosine–O–[$^{35}$S] Sulfated Cholecytokinin Octapeptide from a Nonsulfated Precursor Peptide," *Annal. Biochem.* 154:194–199 (1986).

Naski et eal., "The COOH–terminal Domain of Hirudin," *J. Biol. Chem.* 265:13484–13489 (1990).

Nemerson and Nossell, "The Biology of Thrombosis," *Ann. Rev. Med.* 33:479–488 (1982).

Ocain and Rich, "α–Keto Amide Inhibitors of Aminopeptidases," *J. Med. Chem.* 35:451–456 (1992).

Okamoto and Hijikata, "Potent Inhibition of Thrombin by the Newly Synthesized Arginine Derivative No. 805. The Importance of Stero–Structure of its Hydrophobic Carboxamide Portion," *Biochem. Biophys. Res. Commun.* 101:440–446 (1981).

Pande et al. "Interaction of Lysine Residues with the Metal Thiolate Clusters in Metallothionein," *Biochemistry,* 24:6717–6722 (1985).

Powers et al., "Indium–111 Platelet Scintigraphy in erebrovascular Disease," *Neurology* 32:938–943 (1982).

Prins and Hirsh, "Heparin as Adjunctive Treatment After Thrombolytic Therapy for Acute Myocardial Infarction," *Amer. Journal of Cardiol.* 67:3A–11A (1991).

Ross, "Myocardial Infarction: Adjunctive Antithrombotic Therpay to Thrombolysis," *Thrombosis in Cardiovascular Disorder,* pp. 327–341, W.B. Saunders Co. (1991).

Ross, "The Pathogeneis of Atherosclerosis—An Update," *New England J. Med.* 314:488–500 (1986).

Rubens et al., "The Effect of Antithrombin III–Independent Thrombin Inhibitors and Heparin on Fibrin Accretion onto Fibrin–Coated Polyethylene," *Thrombosis and Haemostasis* 69:130–134 (1993).

Rydel et al., "The Structure of a Complex of Recombinant Hirudin and Human α–Thrombin," *Science* 249:277–280 (1990).

Sarembock et al., "Effectiveness of Recombinant Desulphatohriudin in Reducing Restenosis After Balloon Angio-Plasty of Atherosclerotic Femoral Arteries in Rabbits," *Circulation* 84:232–243 (1991).

Scharf et al., "Primary Structures of New 'iso–hirudins'", *FEBS Lett* 255:155–110 (1989).

Shuman, "Thrombin–Cellular Interactions," *Ann. NY Acad. Sci.* 485:228–239 (1986).

Skrzypczak–Janukn et al., "X–Ray Crystallographic Structures of the Hirugen: Thrombin and Hirulog: Thrombin Complexes at 2.2 a Resolution," *Thromb. Haemostas,* 65:830 at abstract 507 (1991).

Stone and Hofsteenge, "Kinetics of the Inhibition of Thrombin by Hirudin," *Biochemistry* 25:4622–4628 (1986).

Sugrue et al., "Coronary artery thrombus as a risk factor for actue vessel occlusion during percutaneous transluminal coronary angioplasty: improving results," *Br. Heart J.* 56:62–66 (1986).

Talbot et al., "Recombinant Desulphatohirudin (CGP 39393) Anticoagulant and Antithrombotic Properties in Vivo," *Thrombosis and Haemostasis* 61:77–80 (1989).

Tans et al., "Comparison of Anticoagulant and Procoagulant Activities of Stimulated Platelets and Platelet–Derived Microparticles," *Blood* 77:2641–2648 (1991).

Thakur et al., "Indium–111 Labeled Platelets: Studies on Preparation and Evaluation of In Vitro and In Vivo Functions," *Thromb. Res.* 9:345–357 (1976).

Vale et al., "Characterization of a 41–Residue Ovine Hypothalamic Peptide That Stimulates Secretion of Corticotropin and β–Endorphin," *Science* 213:1394–1395 (1981).

Walz et al., "Thrombin–Elicited Contractile Responses of Aortic Smooth Muscle (42211)," *Proc. Soc. Expl. Biol. Med.* 180:518–526 (1985).

Westerberg et al., "Synthesis of Novel Bifunctional Chelators and Their Use in Preparing Monoclonal Antibody Conjugates for Tumor Targeting," *J. Med. Chem.* 32:236–243 (1989).

Williams and Morrison, "The Kinetics of Reversible Tight–Binding Inhibition," *Methods Enzymol.* 63:437–467 (1979).

Wipf and Kim, "An Approach Toward the Total Synthesis of Cyclotheonamides; Preparation of A C(1) to N(14) Segment," *Tetrahedron Lett.* 33:4275–4278 (1992).

Witting et al., "Thrombin–Specific Inhibition by and Slow Cleavage of Hirulog$_1$–1," *Biochem. J.* 283:737–743 (1992).

Witting et al., "Hirulog–1 and –B2 thrombin specificty," *Biochem J.* 287:663–664 (1992).

α-KETOAMIDE DERIVATIVES AS INHIBITORS OF THROMBOSIS

RELATED APPLICATIONS

This application is a continuation-in-part of U.S. Ser. No. 08/037,574, filed Mar. 25, 1993, the disclosure of which is incorporated by reference herein, including the drawings attached thereto.

FIELD OF INVENTION

In one aspect, the present invention relates to novel compounds, their pharmaceutically acceptable salts, compositions and pharmaceutical compositions, which are useful for preventing or treating in a mammal a pathological condition characterized by thrombosis. Another aspect of the present invention is directed to novel compounds, their pharmaceutically acceptable salts, therapeutic compositions and diagnostic compositions which are useful for in vivo imaging of thrombi in a mammal. In yet another aspect, the present invention relates to methods of preventing, treating or diagnosing in a mammal a pathological condition characterized by thrombosis and methods of in vivo imaging of thrombin in a mammal.

BACKGROUND OF INVENTION

Normal hemostasis is the result of a complex balance between the processes of clot initiation and formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479, (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

The serine protease, thrombin, is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen with the platelet integrin receptor glycoprotein IIb/IIIa which assume their active conformation following thrombin activation of the cell. Berndt, M. C. and Phillips, D. R., Platelets in Biology and Pathology, pp 43–74, Elsevier/North Holland Biomedical Press (Gordon, J. L. edit. 1981). Thrombin-activated platelets can more effectively support additional thrombin production through the assembly of new prothrombinase (factor Xa and Factor Va) and tenase (factor IXa and factor VIIIa) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of high concentrations of thrombin within the vicinity of the thrombus which supports further thrombus growth and extension. Mann, K. G. et al., Blood, 75: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and protolytically activate the circulating zymogen, protein C, to give activated protein C (aPC). Musci, G. et al., Biochemistry, 27: 769 (1988). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 56: 115 (1986). In addition to these direct effects on vascular cells, the enzyme can indirectly elicit proliferation of vascular smooth muscle cells by the release of several potent growth factors (e.g. platelet-derived growth factor and epidermal growth factor) from platelet a-granules following thrombin-induced activation. Ross, R., N. Engl. J. Med., 314: 408 (1986).

Many significant disease states are related to abnormal hemostasis. With respect to the coronary arterial vasculature, local thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in this vascular bed which can result in reduced blood flow to the affected extremity and a predisposition to pulmonary embolism with high risk of mortality. Disseminated intravascular coagulopathy is commonly associated with septic shock, certain viral infections and cancer and is characterized by the rapid consumption of coagulation factors and disseminated vascular microthrombosis which may result in leukocyte activation, inflammation and organ failure.

Arterial thrombosis is a major clinical cause of morbidity and mortality. It is the primary cause of acute myocardial infarction which is one of the leading causes of death in the Western world. Arterial rethrombosis also remains one of the primary causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, notably platelets, which make up a large percentage of arterial thrombi. There is currently no clinically approved effective therapy for the treatment or prevention of acute arterial thrombosis or rethrombosis since heparin, the most widely used clinical anticoagulant administered i.v., has not been shown to be universally effective in this setting. Prins, M. H. and Hirsh, J., J. Am. Coll. Cardiol., 67: 3A (1991).

Besides the unpredictable, recurrent thrombotic reocclusion which frequently occurs following PTCA, a profound restenosis of the recanalized vessel occurs in 30 to 40% of patients 1 to 6 months following this procedure. Califf, R. M. et al., J. Am. Coll. Cardiol., 17: 2B (1991). Many of these patients require further treatment with either a repeat. PTCA or coronary artery bypass surgery to relieve the newly formed stenosis which results in restriction of blood supply to the myocardium. Restenosis of a mechanically damaged vessel is not the direct result of a thrombotic process but instead is the result of a proliferative response of the vascular smooth muscle cells constituting the wall of the artery. Over time this results in a decreased luminal diameter of the affected vessel and decreased blood flow due to increased cellular and pericellular mass. Id. As for arterial thrombosis, there is currently no effective pharmacologic treatment for the prevention of vascular restenosis following mechanical recanalization.

The need for safe and effective therapeutic anticoagulants has in one aspect focused on the role of thrombin as the final enzyme in the process of blood coagulation.

As previously mentioned, recurrent arterial thrombosis remains one of the leading causes of failure following enzymatic or mechanical recanalization of occluded Coronary vessels using thrombolytic agents or percutaneous transluminal coronary angioplasty (PTCA), respectively. After lysis of a clot by enzymatic means, residual thrombi may be responsible for reocclusion of the recanalized coronary artery via increased thrombus growth. Gash, A. K. et al., Am. J. Cardiol., 57: 175 (1986); Shaer, D. H. et al., Circulation, 76: 57 (1984). Mechanical recanalization by coronary angioplasty may not prevent reocclusion, and in the presence of a residual thrombus, may precipitate acute reocclusion, requiring bypass surgery. Sugrue, D. et al., Br. Heart J., 56: 62 (1986). The development of methods for direct thrombus imaging have been stimulated by these clinical problems.

In vivo diagnostic imaging for intravascular thrombi has been reported. These imaging methods use compounds which are detectable by virtue of being labelled with radioactive or paramagnetic atoms. For example, platelets labelled with the gamma emitter, In-111, have been reported as an imaging agent for detecting thrombi. Thakur, M. L. et al., Thromb. Res., 9: 345 (1976); Powers et al., Neurology, 32: 938 (1982). A thrombolytic enzyme, such as streptokinase, labelled with the gamma emitter Tc-99m, has been proposed as an imaging agent. Wong, D. W., U.S. Pat. No. 4,418,052 (1983). The fibrin-binding domains of *Staphylcoccus aureus* derived protein A labelled with the gamma emitters, I-125 and I-131, have been proposed as imaging agents. Pang, R. H. L., U.S. Pat. No. 5,011,686 (1991). Monoclonal antibodies having specificity for fibrin (in contrast to fibrinogen) and labelled with the gamma emitter, Tc-99m, have been proposed as imaging agents. U.S. Pat. Nos. 5,024,829 (1991) to Berger, H. J. et al.; and 4,980,148 (1990) to Dean, R. T. et al. The use of the paramagnetic contrasting agent, gadolinium diethylenetriaminepentaacetic acid, in magnetic resonance imaging of patentis treated by thrombolysis for acute myocardial infarction has been reported. De Roos, A. et al., Int. J. Card. Imaging, 7: 133 (1991).

Most preferred natural substrates for thrombin are reported to contain an uncharged amino acid in the P3 recognition subsite. For example, the thrombin cleavage site on the Aa chain of fibrinogen, which is a physiological substrate for thrombin, is reported to contain a glycine residue in this position while the cleavage site on the Bb chain contains a serine, as shown below:

| P4 | P3 | P2 | P1 | P1' | | |
|---|---|---|---|---|---|---|
| Gly | Gly | Val | Arg/Gly | Fibrinogen Aa Chain | | [SEQ. ID. NO.1[ |
| Phe | Ser | Ala | Arg/Gly | Fibrinogen Bb Chain | | [SEQ. ID. NO. 2] |

Peptidyl derivatives having an uncharged residue in the P3 position which are believed to bind to the active site of thrombin and thereby inhibit the conversion of fibrinogen to fibrin and cellular activation have been reported. Additionally, these derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 (1990) and Bajusz, S. et al., Int. J. Peptide Protein Res. 12: 217 (1970); Kettner, C. and Shaw, E., Methods Enzymol., 80: 826 (1987); Kettner, C. et al., EP 293,881 (published Dec. 7, 1988); Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991).

Peptidyl compounds which are said to be active site inhibitors of thrombin but which are said to differ in structure from those containing a uncharged amino acid in the P3 recognition subsite have been reported. The compound, Argatroban (also called 2R,4R-4-methyl-1-[N-2-(3-methyl-1,2,3,4-tetrahydro-8-quinolinesulfonyl)-L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to the active site as well as an accessory or exo-site on the enzyme have been reported. For example, hirudin and its various peptidyl derivatives have been reported to inhibit both conversion of fibrinogen to fibrin and platelet activation by binding to either both the active site and exo-site, or to the exo-site only, of thrombin. Markwardt, F., Thromb.

Haemostas., 66: 141 (1991). Hirudin is said to be one of the most potent inhibitors of thrombin known. Marki, W. E. and Wallis, R. B., Thromb. Haemostas., 64: 344 (1990). Hirudin is reported to inhibit thrombin by binding to both its anion-binding exo-site and to its catalytic active site, sites which are distinct and physically distant from each other. Rydel, T. J. et al., Science, 249: 277 (1990). Its potency as measured by the inhibitory constant ("Ki") was determined to be $22 \times 10^{-15}$M. Stone et al., Biochemistry, 25: 4622, 4624 (1986). Hirudin has been reported to be a potent antithrombotic agent in vitro and in vivo. Markwardt, F. et al., Pharmazie, 43: 202 (1988); Kelly, A. B. et al., Blood, 77: 1 (1991). In addition to its antithrombotic effects, hirudin has been reported to also inhibit smooth muscle proliferation and the associated restenosis following mechanical damage to a atherosclerotic rabbit femoral artery. Sarembock, I. J. et al., Circulation, 84: 232 (1991).

Hirudin has been reported to be a 65 amino acid polypeptide which was originally isolated from leech salivary gland extracts. The primary amino acid sequence, as shown below, has been reported. Krstenansky J. L. et al., Thromb. Hemostasis, 63: 208 (1990).

[SEQ. ID. NO. 3]

```
1               5                    10
Val—Val—Tyr—Thr—Asp—Cys—Thr—Glu—Ser—Gly—Gln—Asn—
             15                20
Leu—Cys—Leu—Cys—Glu—Gly—Ser—Asn—Val—Cys—Gly—Gln—
25                      30                      35
Gly—Asn—Lys—Cys—Ile—Leu—Gly—Ser—Asp—Gly—Glu—Lys—
             40                      45
Asn—Gln—Cys—Val—Thr—Gly—Glu—Gly—Thr—Pro—Lys—Pro—
50                      55                      60
Gln—Ser—His—Asn—Asp—Gly—Asp—Phe—Glu—Glu—Ile—Pro—
                          65
Glu—Glu—Tyr(SO₃)—Leu—Gln—OH
```

The primary amino acid sequence of various isoforms of hirudin has also been reported. Scharf M. et al., FEBS Lett., 255: 105 (1989). The C-terminal portion (comprised of amino acids 56 to 64) of hirudin has been reported to be the minimal domain required for the binding of hirudin to the exo-site of thrombin. Krstenansky, J. L., et al., Thromb. Hemostasis, 63: 208 (1990); Mao, S. J. T., et al., Biochemistry, 27: 8170 (1988); Krstenansky, et al., FEBS Lett., 211: 10 (1987). Peptides similar to this C-terminal portion have been reported to inhibit thrombin-induced clot formation and/or thrombin-mediated platelet aggregation.

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989.). The region of hirudin represented by hirugen has been shown using x-ray crystallographic techniques to bind directly to the exo-site of thrombin. Skrzypczak-Jankun, E. et al., Thromb. Haemostas., 65: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Naski, M. C. et al., J. Biol. Chem., 265: 13484 (1990); Liu, L. W. et al., J. Biol. Chem., 266: 16977 (1991). Hirugen also is reported to block thrombin-mediated platelet aggregation. Jakubowski, J. A. and Maraganore, J. M., Blood, 75: 399 (1990). The inhibition of thrombin-induced fibrin clot formation resulting from substitution of the various amino acid residues on a C-terminal peptide of hirudin has also been reported. Krstenansky, J. L., et al., Thromb. Hemostasis, 63: 208 (1990).

A chimeric peptide has been reported to be comprised of a C-terminal peptide of hirudin (amino acids 53 to 64) coupled to a peptide containing an Arg-Gly-Asp (RGD) sequence. The C-terminal peptide, with or without the RGD-containing peptide, is said to inhibit both thrombin-induced clot formation and thrombin-mediated platelet aggregation with an IC$_{50}$ of 0.6 mM and 7 mM, respectively. Church, F. C. et al., J. Biol. Chem., 266: 11975 (1991).

Another chimeric peptide, Hirulog, has been reported to be a synthetic molecule comprised of a hirugen-like sequence (amino acids 53 to 64 of hirudin) linked by a glycine-spacer region to the peptide, D-phenylalanyl-prolyl-arginine. The latter portion of this peptide is said to be based on a preferred substrate recognition site for thrombin. The hirugen-like sequence is said to be located at the C-terminus of this peptide. Maraganone, J. M. et al., Biochemistry, 29: 7095 (1990); Maraganone, J. M. et al., International Application No. WO 91/02750 (published Mar. 7, 1991); and Dimaio, J. et al., International Application No. WO 91/19734 (published Dec. 26, 1991). Hirulog is said to bind to thrombin in a bivalent manner and this binding is characterized by an Ki of $2.56 \times 10^{-9}$M. The D-phenylalanyl-prolyl-arginine peptide is said to bind to the catalytic site of thrombin, whereas the hirugen-like sequence binds to its anion-binding exo-site. Witting, J. I. et al., Biochem. J., 283: 737 (1992). Hirulog has been reported to be an effective antithrombotic agent in vivo, preventing both fibrin-rich and platelet-rich thrombosis. Maraganone, J. M. et al., Thromb. Haemostas., 65: 651 at abstract 17 (1991).

Hirulog has been reported to have the structure, H-(D-Phe)-Pro-Arg-Pro-(Gly)$_4$-Asn-Gly-Asp-Phe-Glu-Glu-Ile-Pro-Glu-Glu-Tyr-Leu, and is said to be potent thrombin inhibitor. The substitution of various amino acids on the hirugen-like sequence of Hirulog and the effect thereof on binding constant has been reported. Bourdon, P. et al., FEBS, 294: 163 (1991). Substitution of the D-phenylalanine residue with a b-cyclohexyl-D-alanine residue is said to provide a more potent thrombin inhibitor, characterized by a Ki of $0.077 \times 10^{-9}$M. Witting, J. I. et al., Biochem. J., 287: 663, 664 (1992). Addition of a methylene group between the arginine a-carbon and carbonyl of Hirulog is said to provide a non-cleavable thrombin inhibitor characterized by a Ki of $7.4 \times 10^{-9}$M, while substitution of a methylene group for this carbonyl alone is said to provide a poor thrombin inhibitor having a Ki of greater than $2000 \times 10^{-9}$M. Kline, T. et al., Biochem. Biophys. Res. Commun., 177: 1049, 1052–1054 (1991). N-acetyl-D-Phe-Pro Arg-[yC(=O)—CH$_2$]—CH$_2$—CH$_2$—CH$_2$—(C=O)-Gln-Ser-His-Asn-Asp-Gly-Asp-Phe-Glu-Glu-Ile-Pro-Glu-Glu-Tyr-Leu-Gln is said to be potent thrombin non-cleavable inhibitor having a. Ki of $0.14 \times 10^{-9}$M. Dimaio, J. et al., International Application, at page 44.

Cyclotheonamide A and B, isolated from the marine sponge, Theonella, a genus of marine sponges, have been reported to be inhibitors of thrombin with an IC$_{50}$ of 0.076 mg/mL ($9.9 \times 10^{-8}$M). Structurally, they have been characterized as cyclic peptides containing an arginine a-keto amide moiety. Fusetani et al., J. Am. Chem. Soc. 112: 7053–7054 (1991).and Hagihara et al., J. Am. Chem. Soc, 114: 6570–6571 (1992). It has been proposed that the a-keto group of the cyclotheonamides may function as an electrophilic mimic of the Arg-X scissile amide bond of the thrombin substrates. Hagihara et al., Id. at 6570. The partial synthesis of cyclotheonamide A and the total synthesis of cyclotheonamide B have been reported. Wipf et al., Tetrahedron Lett., 33: 4275–4278 (1992) and Hagihara et al., J. Am. Chem. Soc, 114: 6570–6571 (1992).

a-Keto-amide derivatives of other amino acids and peptides have also been reported to be inhibitors of proteases. For example, L-valyl-L-valyl-3-amino-2-oxovaleryl-D-leucyl-L-valine had been reported to be an inhibitor of prolyl endopeptidase. Nagai et al., J. Antibiotics, 44: 956–961 (1991). 3-Amino-2-oxo-4-phenylbutanoic acid amide has been reported to be an inhibitor of arginyl aminopeptidase (with a Ki of 1.5 mM), cytosol aminopeptidase (with a Ki of 1.0 mM) and microsomal aminopeptidase (with a Ki of 2.5 mM). Ocain et al., J. Med. Chem., 35: 451–456 (1992). 2-Oxo-2-(pyrrolidin-2-yl)acetyl derivatives have been reported to be inhibitors of prolyl endopeptidase. Someno et al., European Patent Application No. 468,339 (published Jan. 29, 1992). Certain a-keto-amide derivatives of peptides have been reported to inhibit various serine and cysteine proteases. Powers J. C., International Application No. WO 92/12140 (published Jul. 23, 1992).

a-Keto ester derivatives of N-protected amino acids and peptides have also been reported as inhibitors of serine proteases, such as neutrophil elastase and cathepsin. G. Mehdi et al., Biochem. Biophys. Res. Commun., 166: 595–600 (1990) and Angelastro et al., J. Med. Chem., 33: 11–13 (1990).

SUMMARY OF INVENTION

The present invention includes novel compounds useful for preventing or treating in a mammal a pathological condition characterized by thrombus formation.

Among other factors, the present invention is based on our discovery of a novel class of compounds which are surprisingly active as inhibitors of thrombin. According to a preferred aspect, provided are certain compounds which by virtue of their novel structures exhibit the ability to inhibit thrombin in a potent manner substantially exceeding that of thrombin inhibitors described in the art. Their high potency allows the preferred compounds of the present invention to be especially useful in the formulation of compositions, therapeutic compositions and diagnostic compositions which can be administered at comparatively lower doses for the various therapeutic or diagnostic procedures in which they are useful.

According to one aspect, compounds of the present invention are provided which are represented by the formula:

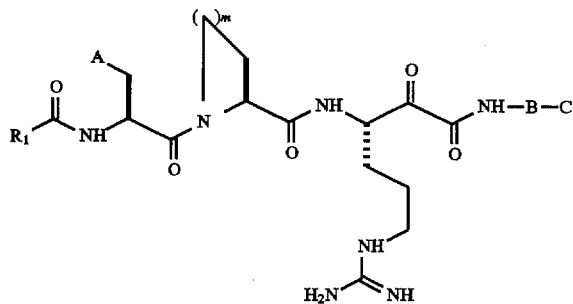

wherein $R_1$ is alkyl of 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of 1 to about 12 carbon atoms, alkenyloxy of about 3 to about 8 carbon atoms, aryloxy of about 6 to about 14 carbon atoms, or aralkyloxy of about 6 to about 15 carbon atoms;

A is selected from the group consisting of

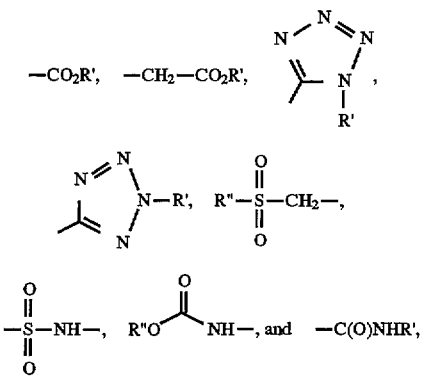

wherein R' is H, alkyl of 1 to about 6 carbon atoms, or aralkyl of about 6 to about 15 carbon atoms and R" is alkyl of 1 to 6 carbon atoms or aralkyl of about 6 to about 15 carbon atoms;

m is 1, 2 or 3;

B is a peptide represented by the formula, $B_1$-$B_2$-$B_3$-$B_4$-$B_5$, wherein $B_1$ is peptide of 5 to 8 amino acids, $B_2$ is Arg, Asn, Asp or Gln; $B_3$ is Gly; $B_4$ is Asp; and $B_5$ is Nap, Phe, Tha, Trp or Tyr;

C is a peptide represented by the formula: $C_1$-$C_2$-$C_3$-$C_4$-$C_5$-$C_6$-$C_7$-Z, wherein $C_1$ is Glu; $C_2$ is Ala, Glu or Pro; $C_3$ is Ile, Leu or Ser; $C_4$ is Hyp, Leu or Pro; $C_5$ is Asp, Glu, Ala-Asp, Ala-Glu, Asp-Asp, Asp-Glu, Glu-Asp or Glu-Glu; $C_6$ is Ala, Ile, Tyr, Tyr(O-SO$_3$H), Tyr(3-iodo), Tyr(3,5-diiodo), Ala-Tyr, Ala-Tyr(O—SO$_3$H), Ala-Tyr(3-iodo) or Ala-Tyr(3,5-diiodo): $C_7$ is Ala, Asp, Cha, Leu or Tyr; and Z is —OH or —NH$_2$; or pharmaceutically acceptable salt thereof.

In another aspect, the present invention includes pharmaceutical compositions useful for preventing or treating in a mammal a pathological condition characterized by thrombus formation, comprising a pharmaceutically acceptable carrier and a therapeutically effective amount of a compound of the present invention.

In another aspect, the present invention includes methods of preventing or treating in a mammal a pathological condition characterized by thrombus formation.

In another aspect, the present invention includes novel compounds which are useful for in vivo imaging of thrombi in a mammal. According to a preferred aspect, compounds of the present invention include those represented by the formula:

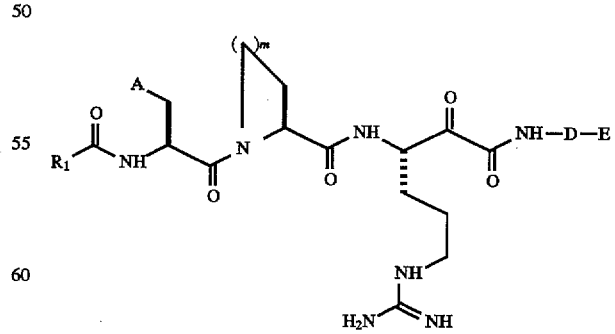

wherein $R_1$ is alkyl of 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of 1 to about 12 carbon atoms, alkenyloxy of about 3 to about 8 carbon atoms, aryloxy of about 6 to about 14 carbon atoms, or aralkyloxy of about 6 to about 15 carbon atoms;

A is selected from the group consisting of

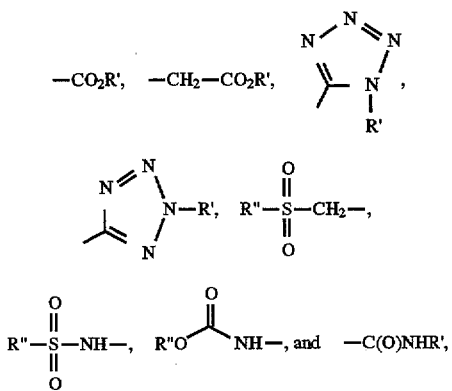

wherein R' is H, alkyl of 1 to about 6 carbon atoms, or aralkyl of about 6 to about 15 carbon atoms and R" is alkyl of 1 to 6 carbon atoms or aralkyl of about 6 to about 15 carbon atoms;

m is 1, 2 or 3;

D is a peptide represented by the formula, $D_1$-$D_2$-$D_3$-$D_4$-$D_5$, wherein $D_1$ is $(Gly)_p$-X-$(Gly)_q$ when $D_2$ is Arg, Asn, Asp or Gln, or $D_1$ is —$(Gly)_{p+q}$-Gly— when $D_2$ is X, wherein p and q are independently selected integers from 1 to 7, such that their sum is 4 to 7, and X has the formula:

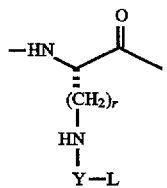

wherein r is an integer selected from 2 to 6, L is a chelating means for chelating a radioactive or paramagnetic atom, and Y is an attaching means for attaching chelating means to the amino group;

$D_3$ is Gly;

$D_4$ is Asp; and $D_5$ is Nap, Phe, Tha, Trp or Tyr;

E is a peptide represented by the formula: $E_1$-$E_2$-$E_3$-$E_4$-$E_5$-$E_6$-$E_7$-Z, wherein $E_1$ is Glu;

$E_2$ is Ala, Glu or Pro;

$E_3$ is Ile, Leu or Ser;.

$E_4$ is Hyp, Leu or Pro;

$E_5$ is Asp, Glu, Ala-Asp, Ala-Glu, Asp-Asp, Asp-Glu, Glu-Asp or Glu-Glu;

$E_6$ is Ala, Ile, Tyr(3-iodo), Tyr(3,5-diiodo), Tyr(O—$SO_3H$), Ala-Tyr(3-iodo), Ala-Tyr(3,5-diiodo), or Ala-Tyr(O—$SO_3H$);

$E_7$ is Ala, Asp, Cha, Leu or Tyr; and

Z is —OH or —$NH_2$; or pharmaceutically acceptable salt thereof.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, preferably a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

Definitions

In accordance with the present invention and as used herein, the following terms are defined with the following meanings, unless explicitly stated otherwise.

The term "alkoxy" refers to the group —OR wherein R is alkyl.

The term "alkyl" refers to saturated aliphatic groups including straight-chain, branched-chain and cyclic groups.

The term "alkenyl" refers to unsaturated hydrocarbyl groups which contain at least one carbon-carbon double bond and includes straight-chain, branched-chain and cyclic groups.

The term "alkenyloxy" refers to the group —OR wherein R is alkenyl.

The term "amino acid" refers to and includes the L-isomers of the naturally occurring a-amino acids, as well as nonnatural a-amino acids such as those used in peptide synthesis of analogs of naturally occurring peptides. The naturally occurring amino acids include glycine (Gly), alanine (Ala), valine (Val), leucine (Leu), isoleucine (Ile), serine (Ser), methionine (Met), threonine (Thr), phenylalanine (Phe), tyrosine (Tyr), tryptophan (Trp), cysteine (Cys), proline (Pro), histidine (His), aspartic acid (Asp), asparagine (Asn), glutamic acid (Glu), glutamine (Gln), g-carboxyglutamic acid, arginine (Arg), ornithine (Orn) and lysine (Lys). Examples of nonnatural a-amino acids include alloisoleucine, 2-aminobutyric acid (Abu), a-cyclohexylglycine b-cyclohexylalanine (Cha), homoarginine (HArg), hydroxyproline (Hyp), homoserine (HSer), norleucine (Nle), norvaline (Nva), phenylalanines substituted on its phenyl ring with one or more alkyl, alkenyl, aryl, aralkyl, alkoxy, alkenyloxy, aryloxy, aralkyloxy, alkylsulfonic, alkylphosphonic, sulfate, phosphate, halogen or nitro groups, b-(2-thienyl)-alanine (Tha), b-furanylalanine (Fua), b-pyridylalanine (Pya), b-benzothienylalanine (Btha), b-(2'naphthyl)-alanine (Nap), 0-alkylated derivatives of serine, threonine or tyrosine, S-alkylated cysteine, 4-phenylacetic acid, 3-iodotyrosine, 3,5-diiodotyrosine, lysine and ornithine substituted with an alkyl group, and D-isomers of naturally occurring amino acids.

The term "anionic amino acid" refers to Phe, Cha or Tyr which are either mono- or di-substituted with a carboxyl, phosphoryl, or sulfonyl group on their respective aromatic or cyclic alkyl rings, as well as Glu, Asp, phosphothreonine, phosphoserine, phosphotyrosine, 3-sulfotyrosine, 4-sulfotyrosine, 5-sulfotyrosine, 3-methylphosphonyltyrosine, and 3-methylsulphonyltyrosine.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to the group —OR wherein R is aryl.

The term "aralkyl" refers to an alkyl group substituted with an aryl group. Suitable aralkyl groups include benzyl, picolyl, and the like, all of which may be optionally substituted.

The term "aralkenyl" refers to an alkenyl group substituted with an aryl group. Suitable aralkenyl groups include styrenyl and the like, all of which may be optionally substituted.

The term "aralkyloxy" refers to the group —OR wherein R is aralkyl.

The term "lipophilic amino acid" refers to Tyr, Trp, Phe, Leu, Nle, Val, Cha, or Pro.

The term "methylene" refers to —$CH_2$—.

In addition, the following abbreviations stand for the following:

"Bn" refers to benzyl.

"Boc" refers to t-butoxycarbonyl.

"$Boc_2O$" refers di-t-butyldicarbonate.

"BocAsp$^{Bn}$-OH" refers to N-Boc-L-aspartic acid-(b-benzyl ester).

"BocPro-OH" refers to N-Boc-L-proline.

"BOP" refers to benzotriazol-1-yloxy-tris-(dimethylamino)-phosphonium-hexafluorophosphate.

"Brine" refers to an aqueous saturated solution of sodium chloride.

"Cbz" refers to benzoyloxy carbonyl.

"DCA" refers to dichloroacetic acid.

"DEC" refers to dicyclohexylcarbodiimide.

"3,4-dehydroPro" refers to 3,4-dehydroproline.

"EDAC-HCl" refers to 1-ethyl-3=(3-dimethylaminopropyl)carbodiimide hydrochloride salt.

"EDT" refers to ethanedithiol.

"Fmoc" refers to 9-fluorenymethyloxycarbonyl.

"HBTU" refers to 2-(1H-benzotriazol-1-yl)-1,1,3,3 tetramethyluroniumhexafluorophosphate.

"HOBT" refers to 1-hydroxybenzotriazole.

"Nap" refers to b-(2'-naphthyl)-alanine.

"TFA" refers to trifluoroacetic acid.

"Tha" refers to b-(2-thienyl)-alanine.

"Tyr(O-SO3H)" refers to tyrosine substituted on its aromatic ring hydroxyl with a sulfate group.

"Tyr(3-iodo)" refers to 3'-iodotyrosine.

"Tyr (3,5-diiodo)" refers to 3',5'-diiodotyrosine

BRIEF DESCRIPTION OF THE DRAWINGS

In FIG. 1, "i" represents potassium cyanide, potassium bicarbonate, water; "ii" represents HCl/water/dioxane; "iii" represents dry HCl/methanol; "iv" represents $Boc_2O$/THF/$NaHCO_3$/$H_2O$/; "v" represents lithiumhydroxide/methanol/water; and "vi" represents Dowex-50 acid form.

DETAILED DESCRIPTION

Compounds and Their Preparation

A. Preferred Compounds

Figure 1:
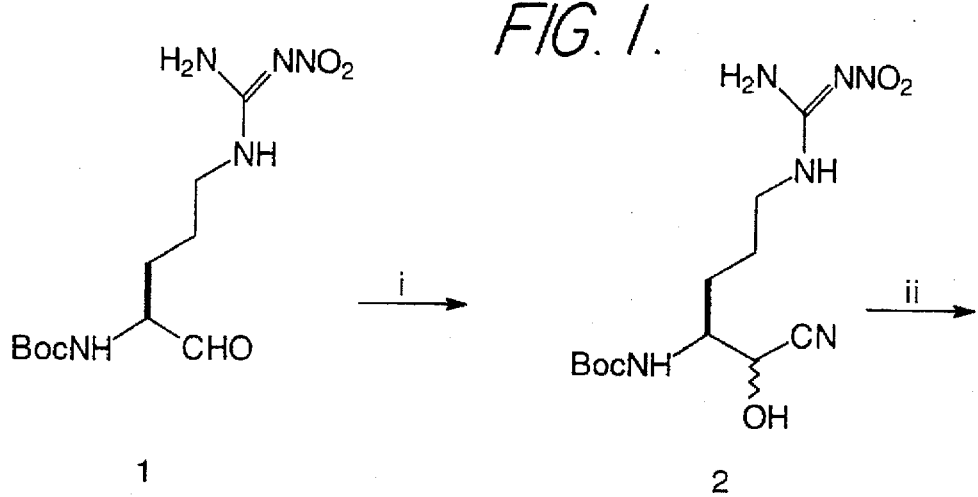
FIG. 1 depicts a reaction scheme describing a process for synthesis of the intermediates of the present invention.
Figure 1:
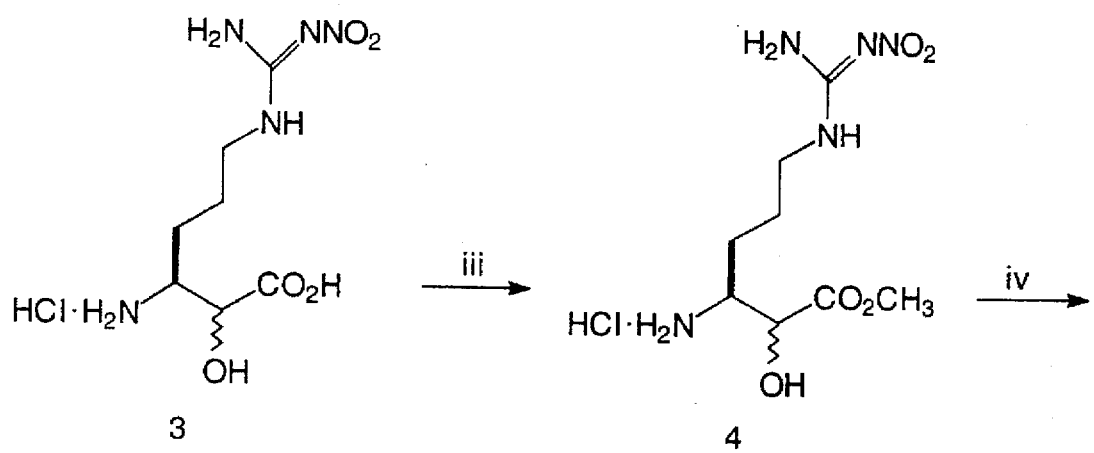
Figure 1:
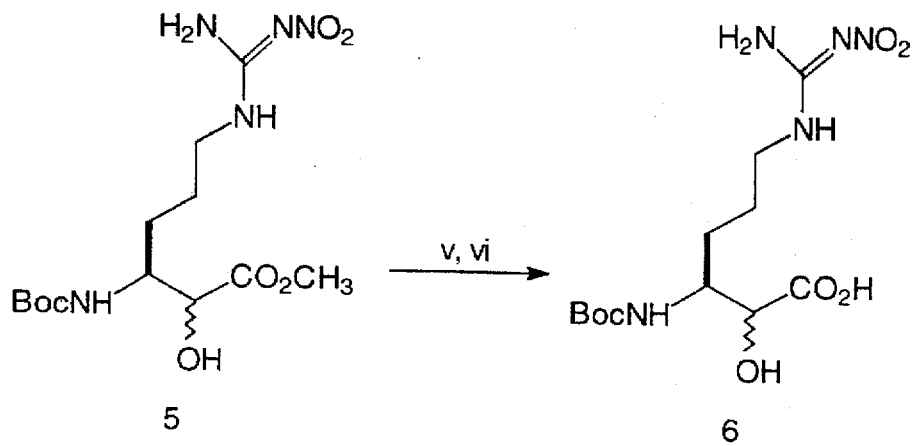

The present invention provides novel compounds useful for preventing or treating in a mammal a pathological condition characterized by thrombosis. These compounds are represented by formula I.

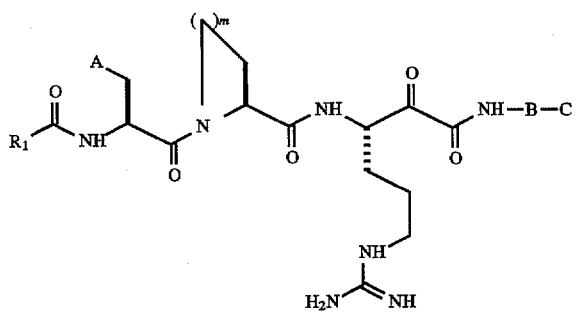

I

These compounds of formula I include those wherein m is 1, 2 or 3. Preferred are those compounds wherein m is 2.

The compounds of the present invention also include those wherein B is a peptide represented by the formula: $B_1$-$B_2$-$B_3$-$B_4$-$B_5$, wherein $B_1$ is peptide of 5 to 8 amino acids, $B_2$ is Arg, Asn, Asp or Gln; $B_3$ is Gly; $B_4$ is Asp; and $B_5$ is Nap, Phe, Tha, Trp or Tyr. Preferred are those compounds, wherein B is selected from the group consisting of -Gly-Gly-Gly-Gly-Gly-Asn-Gly-Asp-Phe- [SEQ. ID. NO. 4] or -Gly-Gly-Gly-Gly-Gly-Arg-Gly-Asp-Phe-. [SEQ. ID. NO. 5]

The compounds of formula I also include those wherein C is a peptide represented by the formula: $C_1$-$C_2$-$C_3$-$C_4$-$C_5$-$C_6$-$C_7$-Z, wherein $C_1$ is Glu; $C_2$ is Ala, Glu or Pro; $C_3$ is Ile, Leu or Ser; $C_4$ is Hyp, Leu or Pro; $C_5$ is Asp, Glu, Ala-Asp, Ala-Glu, Asp-Asp, Asp-Glu, Glu-Asp or Glu-Glu; $C_6$ is Ala, Ile, Tyr, Tyr(O—SO$_3$H), Tyr(3-iodo), Tyr(3,5-diiodo), Ala-Tyr, Ala-Tyr(O—SO$_3$H), Ala-Tyr(3-iodo) or Ala-Tyr(3,5-diiodo); $C_7$ is Ala, Asp, Cha, Leu or Tyr; and Z is —OH or —NH$_2$. Preferred are those compounds, wherein C is selected from the group consisting of -Glu-Glu-Ile-Pro-Glu-Tyr-Leu-OH, [SEQ. ID. NO. 6] -Glu-Glu-Ile-Pro=Glu-Glu-Tyr-Leu-OH, [SEQ. ID. NO. 7] -Glu-Glu-Ile-Pro-Glu-Tyr-Leu-NH$_2$ [SEQ. ID. NO. 8] or -Glu-Glu-Ile-Pro-Glu-Glu-Tyr-Leu-NH$_2$. [SEQ. ID. NO. 9] Especially preferred are those compounds having B as -Gly-Gly-Gly-Gly-Gly-Asn-Gly-Asp-Phe- [SEQ. ID. NO. 10] and C as -Glu-Glu-Ile-Pro-Glu-Tyr-Leu-OH; [SEQ. ID. NO. 11] B as -Gly-Gly-Gly-Gly-Gly-Asn-Gly-Asp-Phe- [SEQ. ID. NO. 12] and C as -Glu-Glu-Ile-Pro-Glu-Glu-Tyr-Leu-OH; [SEQ. ID. NO. 13] B as -Gly-Gly-Gly-Gly-Gly-Arg-Gly-Asp-Phe- [SEQ. ID. NO. 14] and C as -Glu-Glu-Ile-Pro-Glu-Tyr-Leu-OH; [SEQ. ID. NO. 15] or B as -Gly-Gly-Gly-Gly-Gly-Arg-Gly-Asp-Phe- [SEQ. ID. NO. 16] and C as -Glu-Glu-Ile-Pro-Glu-Glu-Tyr-Leu-OH. [SEQ. ID. NO.17]

The compounds of formula I also include those wherein $R_1$ which is an alkyl of 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of 1 to about 12 carbon atoms, alkenyloxy of about 3 to about 8 carbon atoms, aryloxy of about 6 to about 14 carbon atoms, or aralkyloxy of about 6 to about 15 carbon atoms. Compounds of the present invention include those wherein $R_1$ is cyclohexyl, 4-heptyl, 3-methylpentyl, 2-methylpropyl, 3-octyl or 2-phenylethyl. Preferred are those compounds, wherein $R_1$ is 4-heptyl.

The compounds of formula I also include those wherein A is selected from the group consisting of

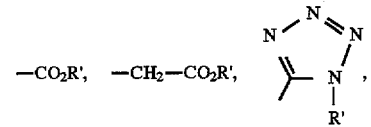

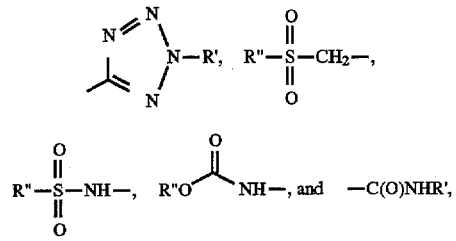

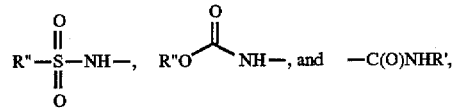

wherein R' is H, alkyl of 1 to about 6 carbon atoms, or aralkyl of about 6 to about 15 carbon atoms and R" is alkyl of 1 to 6 carbon atoms or aralkyl of about 6 to about 15 carbon atoms. The preferred compounds of the present invention include those which are potent inhibitors of human a-thrombin, which potency is characterized by an inhibitor constant, Ki, of less than 0.050 nM.

As previously noted the present invention is based on our discovery of the novel compounds of formula I. Certain of the compounds of the present invention by virtue of their novel structures have imparted to them the ability to inhibit thrombin with a potency substantially exceeding that of thrombin inhibitors reported in the art. This substantial enhanced potency exhibited by these preferred compounds allows then to be used in the formulation of compositions, therapeutic compositions and diagnostic compositions which can then be administered at comparatively and advantageously lower doses in the various therapeutic or diagnostic procedures in which they are useful.

The substantial difference in potency of the preferred compounds of the present invention over compounds described in the art is exemplified in Example A. Certain preferred compounds of the present invention have been found to have an inhibitor constant (Ki) against a-thrombin in the range of 0.0019 to 0.040 nM, while a compound of the art, Hirulog-1, was found to a have Ki of 0.437 nM under the same assay conditions. The improvement in potency provided by the preferred compounds of the present invention is therefore at least ten-fold, and as demonstrated, can exceed a hundred-fold.

Compounds illustrative of the present invention include:

[1] [SEQ. ID. NO. 18]
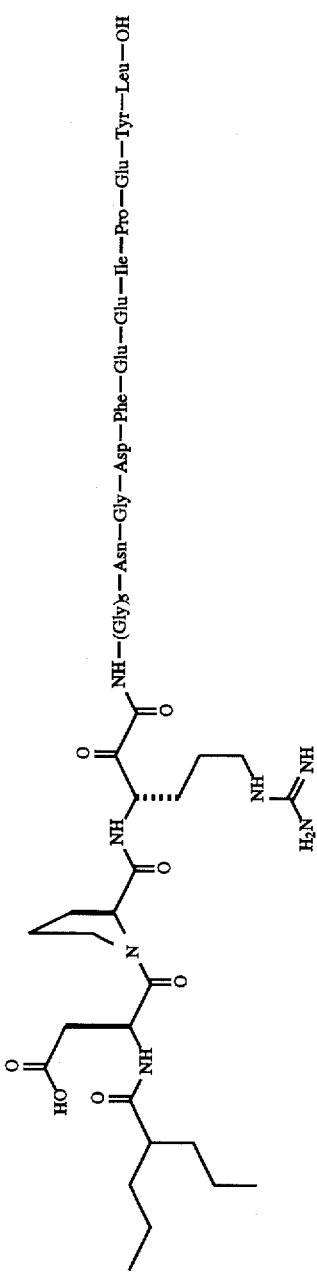
[2] [SEQ. ID. NO. 19]
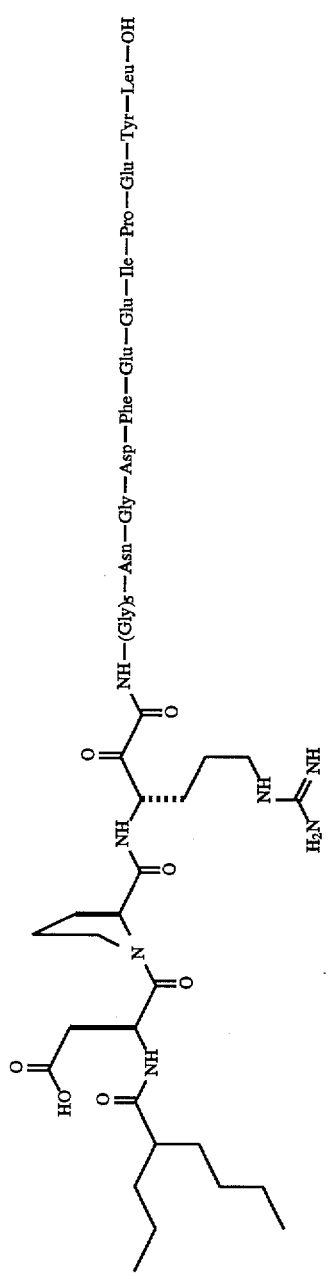
[3] [SEQ. ID. NO. 20]
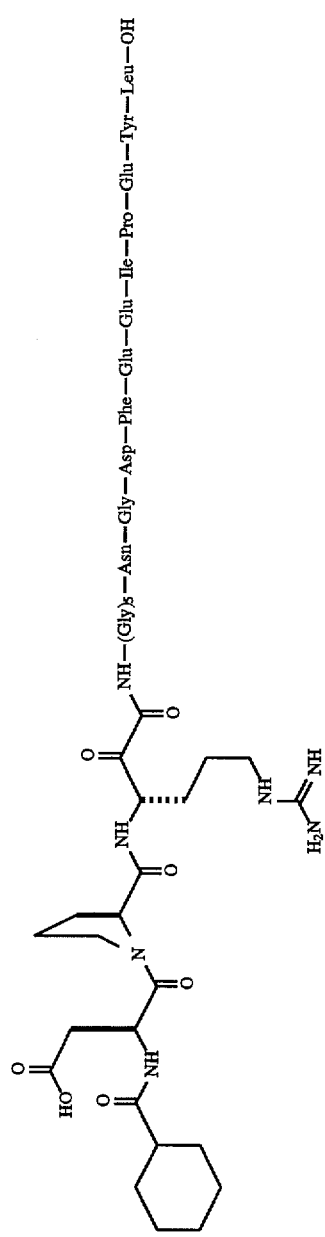

[4] [SEQ. ID. NO. 21]
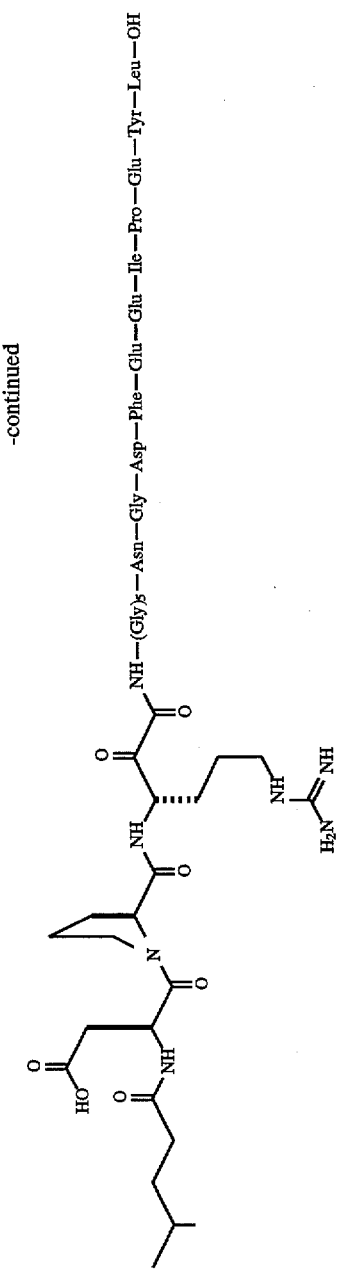
[5] [SEQ. ID. NO. 22]
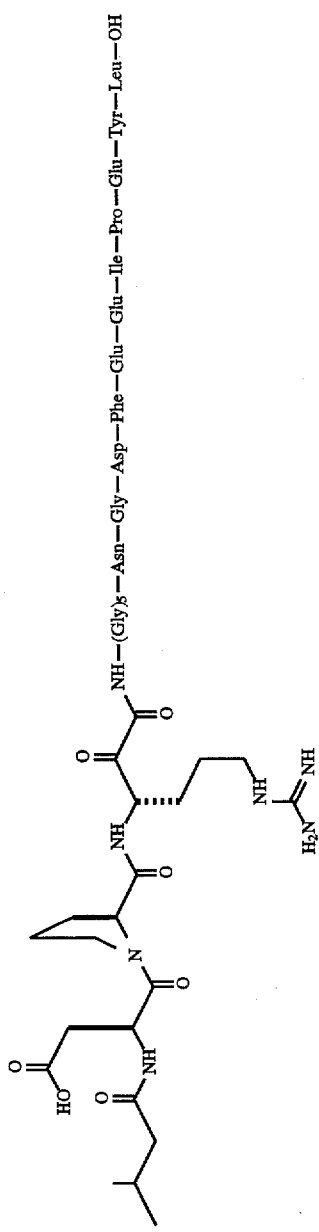
[6] [SEQ. ID. NO. 23]
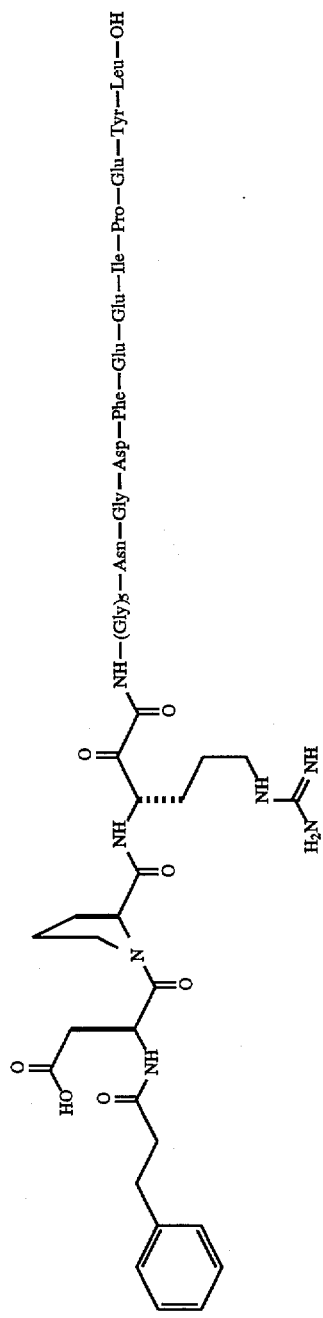

[7] [SEQ. ID. NO. 24]
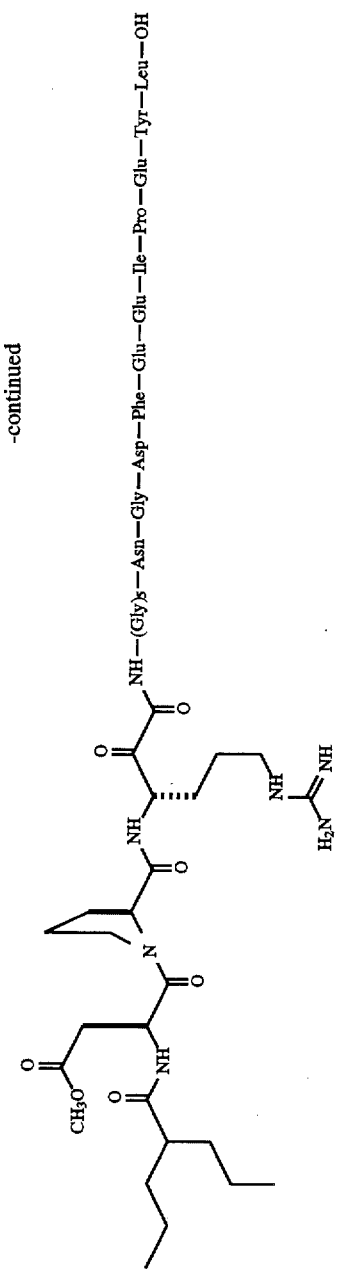
[8] [SEQ. ID. NO. 25]
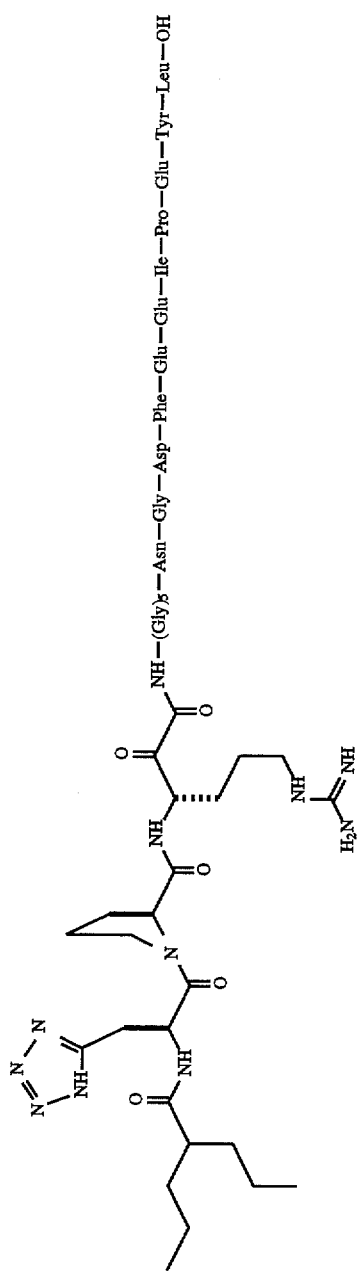
[9] [SEQ. ID. NO. 26]
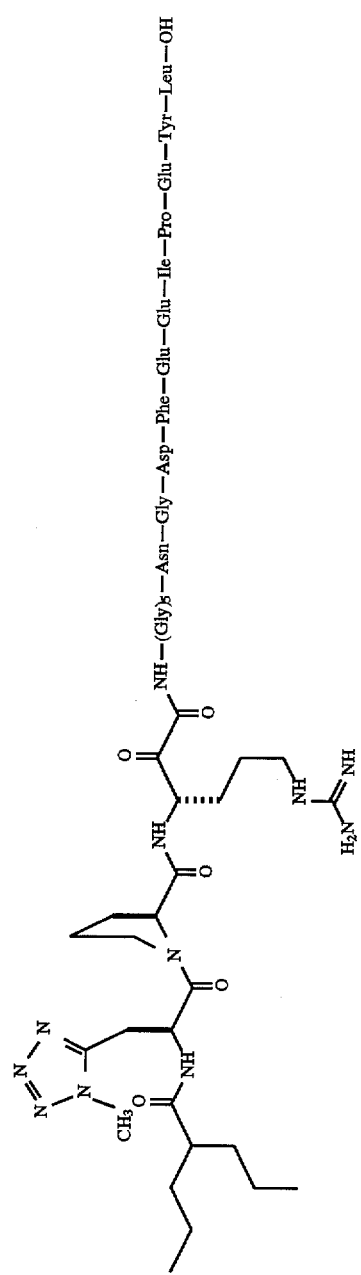

[10] [SEQ. ID. NO. 27]
[11] [SEQ. ID. NO. 28]
[12] [SEQ. ID. NO. 29]
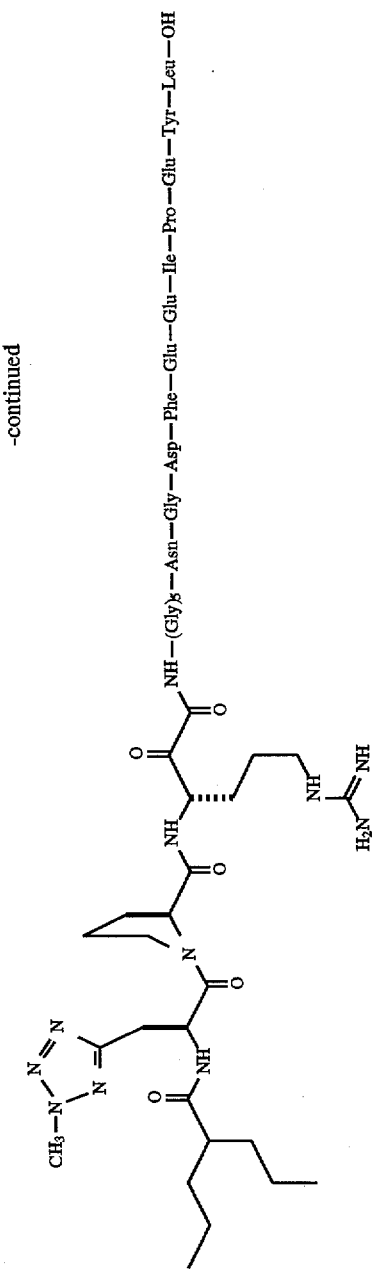
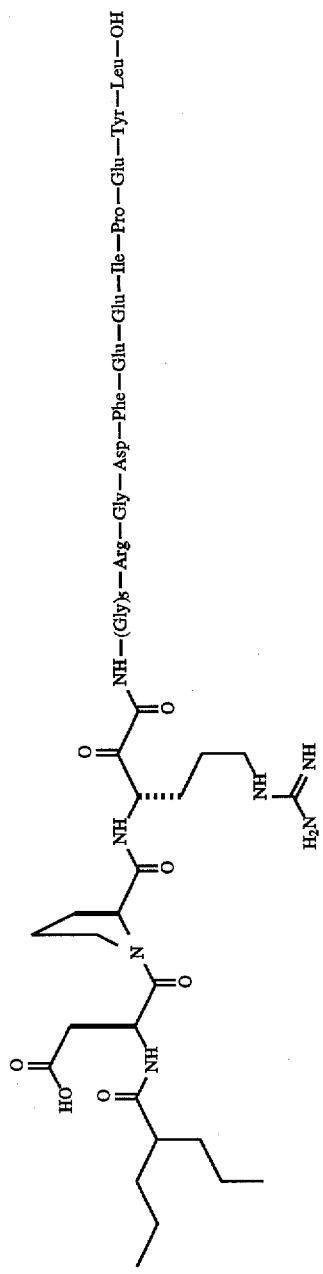
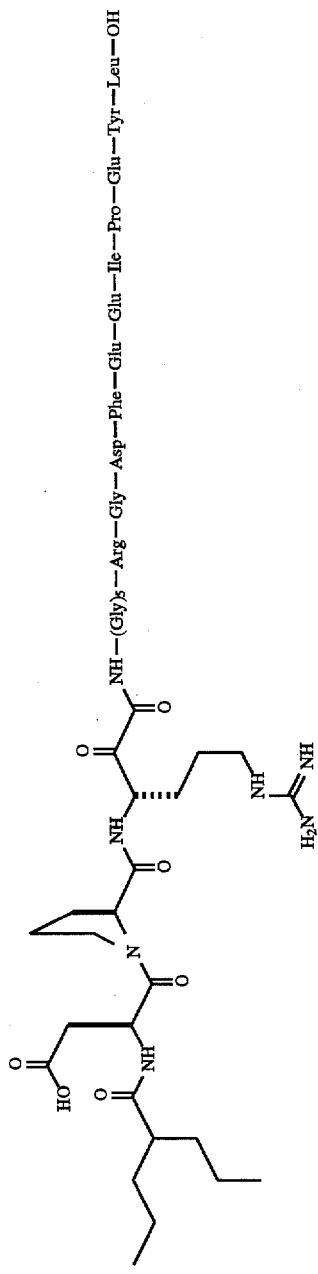

[13] [SEQ. ID. NO. 30]
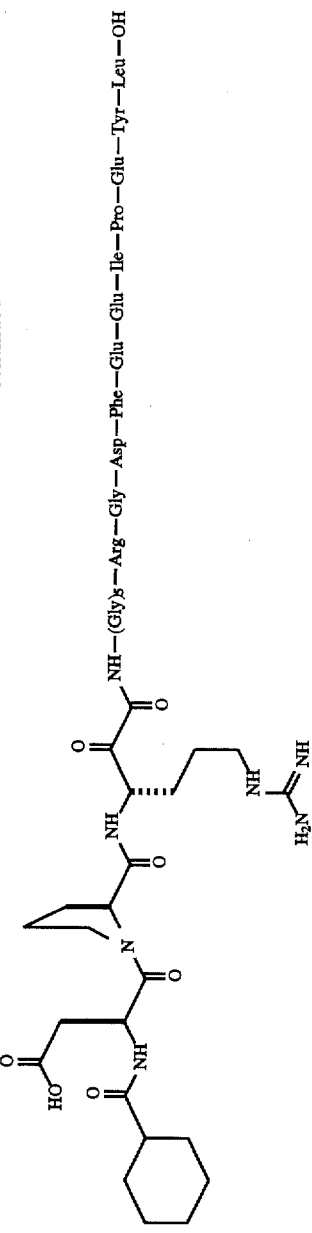
[14] [SEQ. ID. NO. 31]
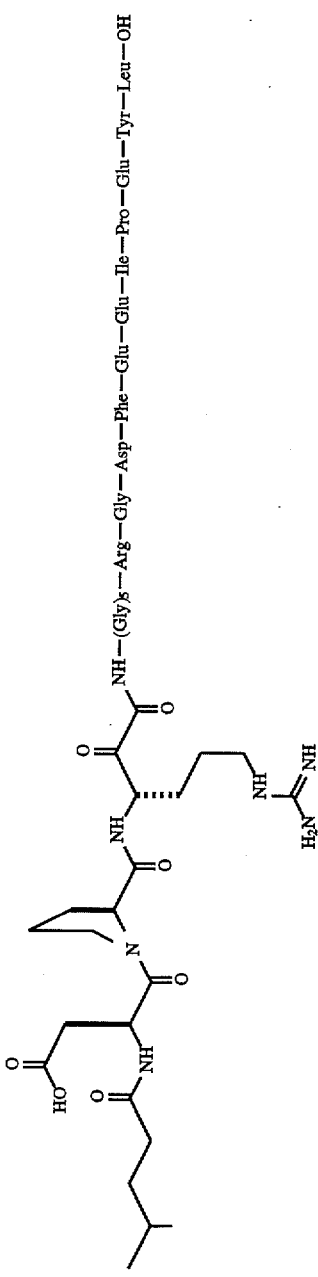
[15] [SEQ. ID. NO. 32]
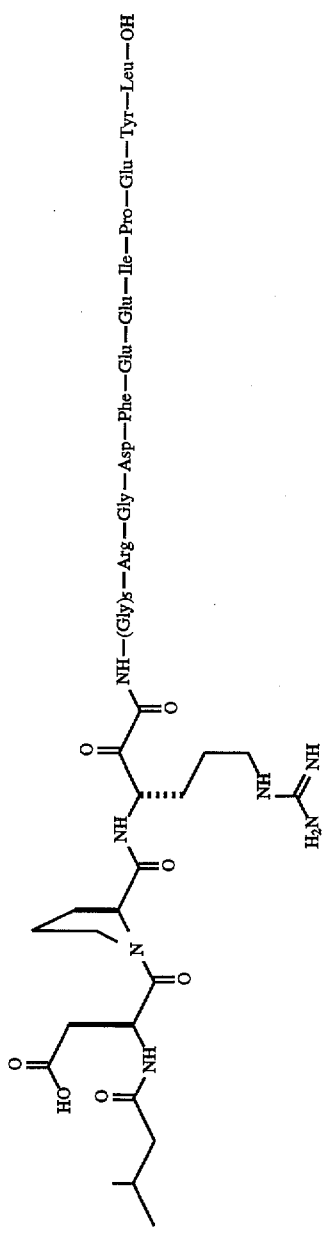

[16] [SEQ. ID. NO. 33]
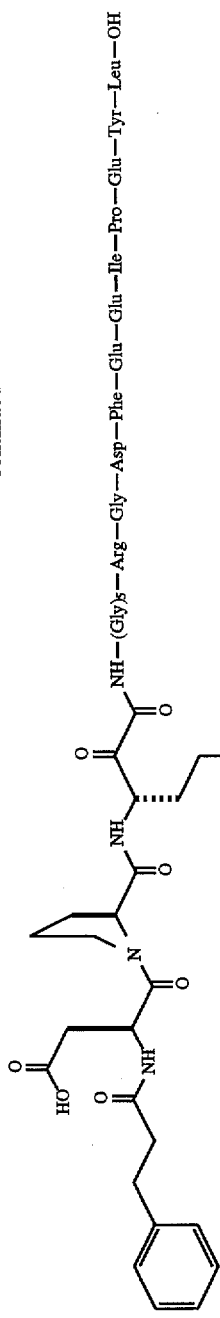
[17] [SEQ. ID. NO. 34]
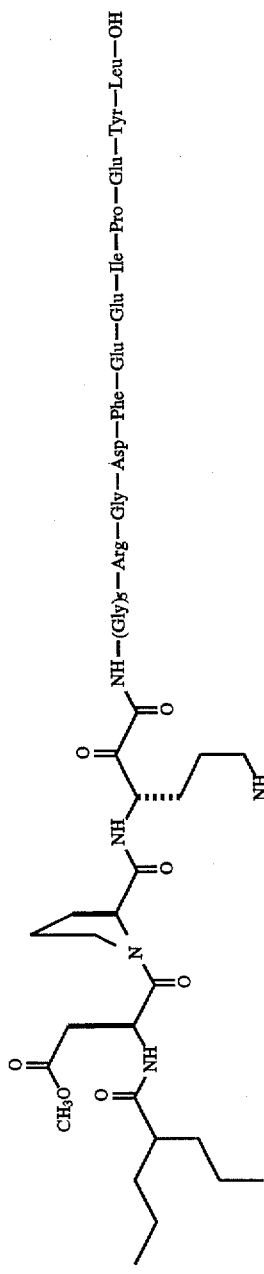
[18] [SEQ. ID. NO. 35]
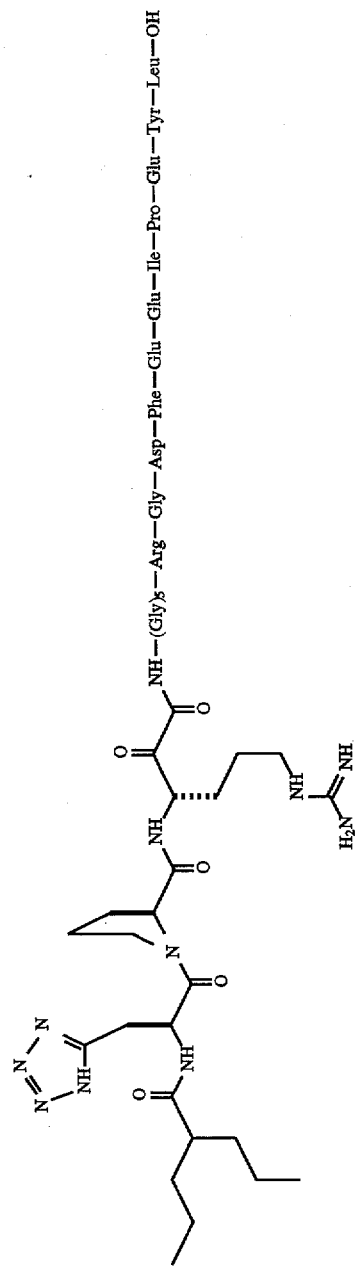

-continued
[19] [SEQ. ID. NO. 36]
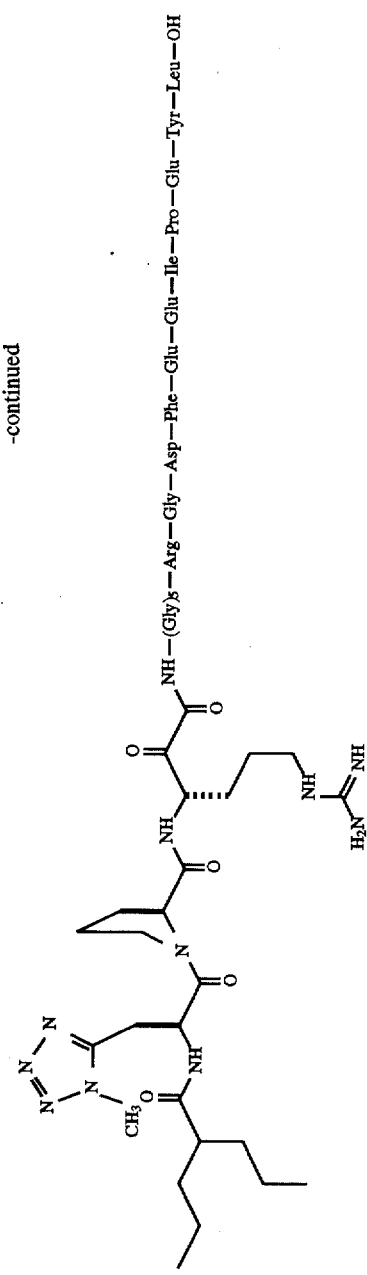
[20] [SEQ. ID. NO. 37]
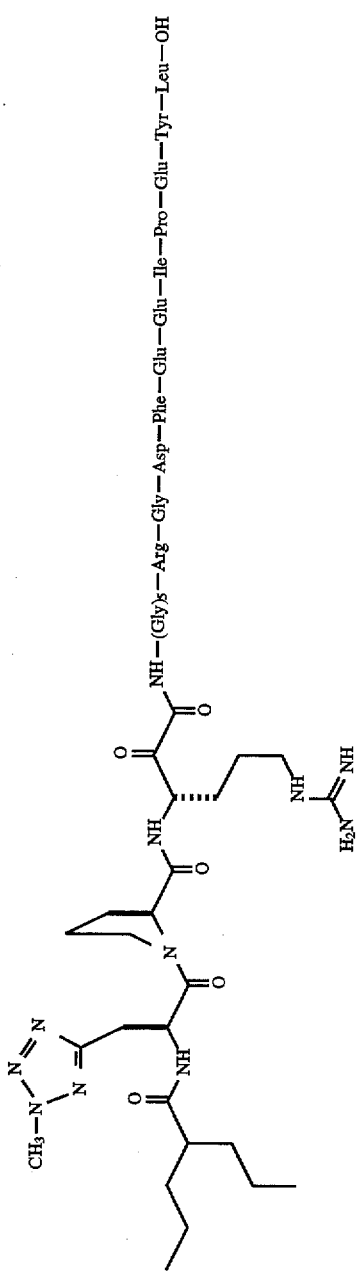
[21] [SEQ. ID. NO. 38]
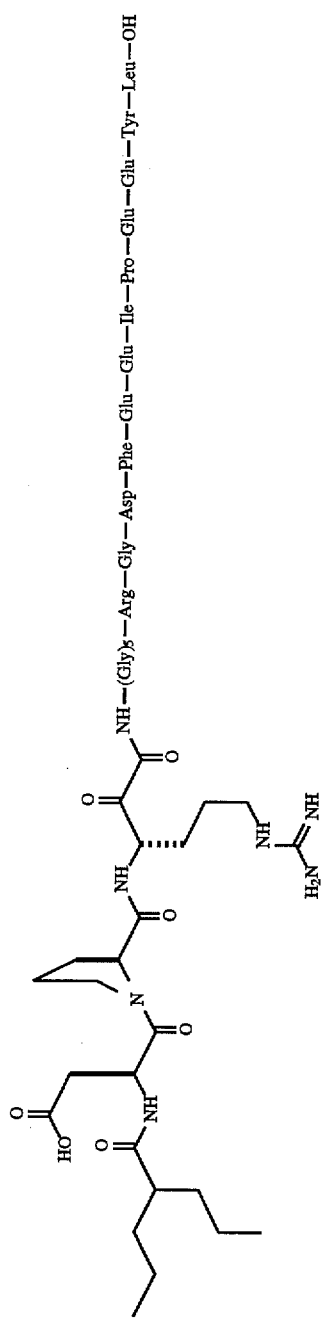

-continued
[22] [SEQ. ID. NO. 39]
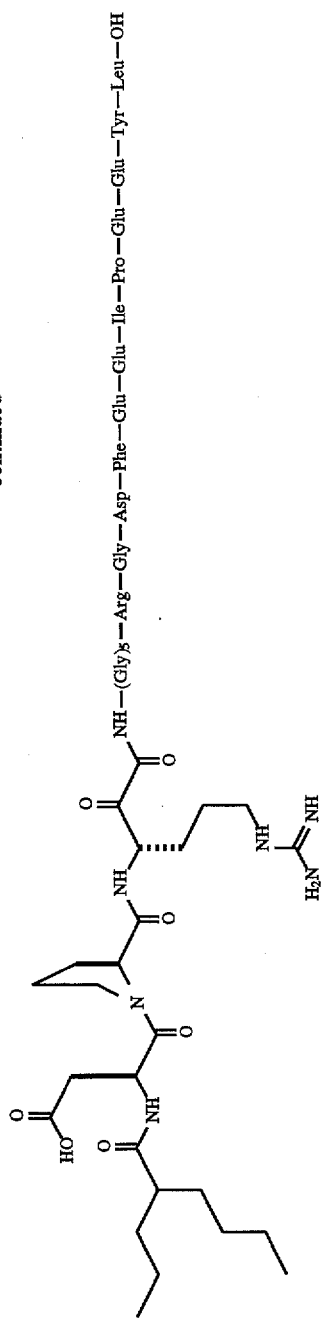
[23] [SEQ. ID. NO. 40]
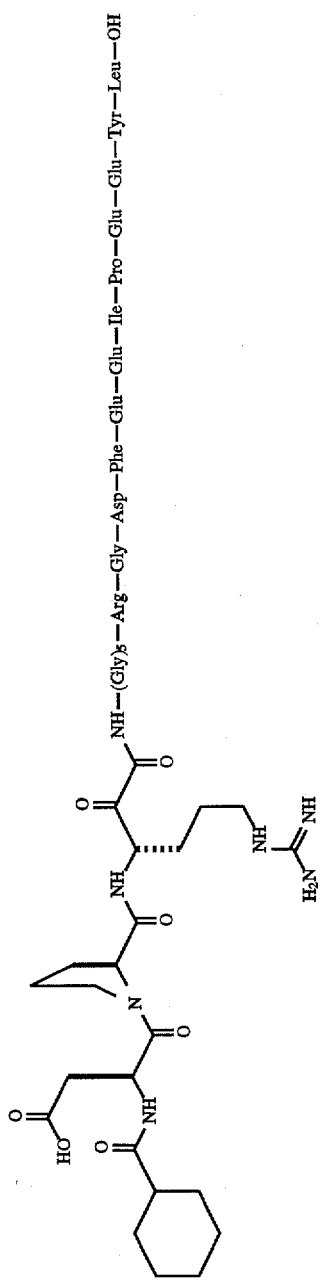
[24] [SEQ. ID. NO. 41]
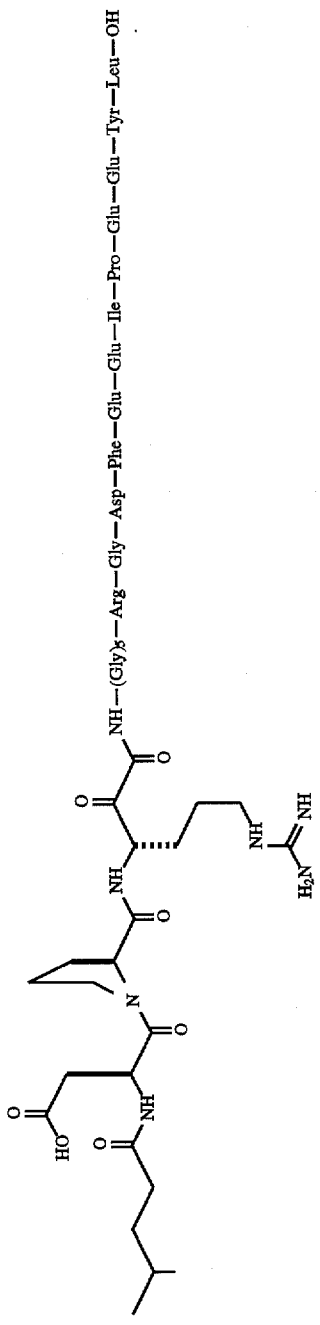

[25] [SEQ. ID. NO. 42]
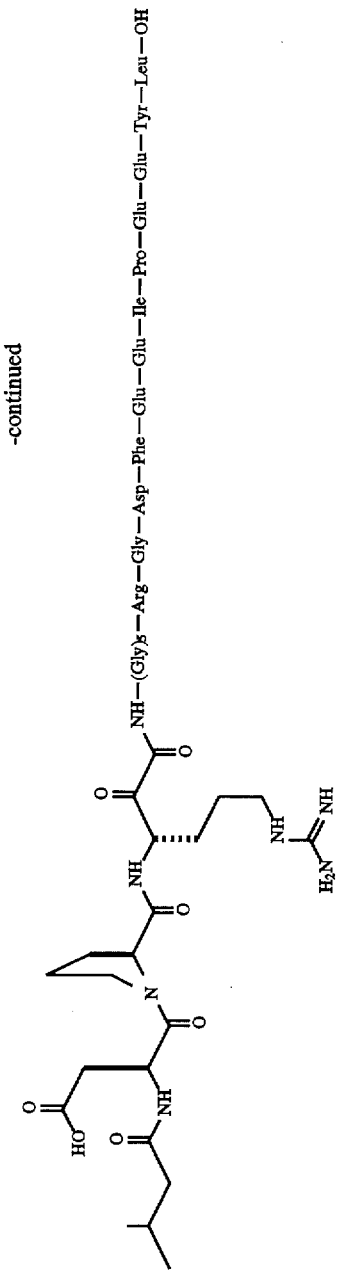
[26] [SEQ. ID. NO. 43]
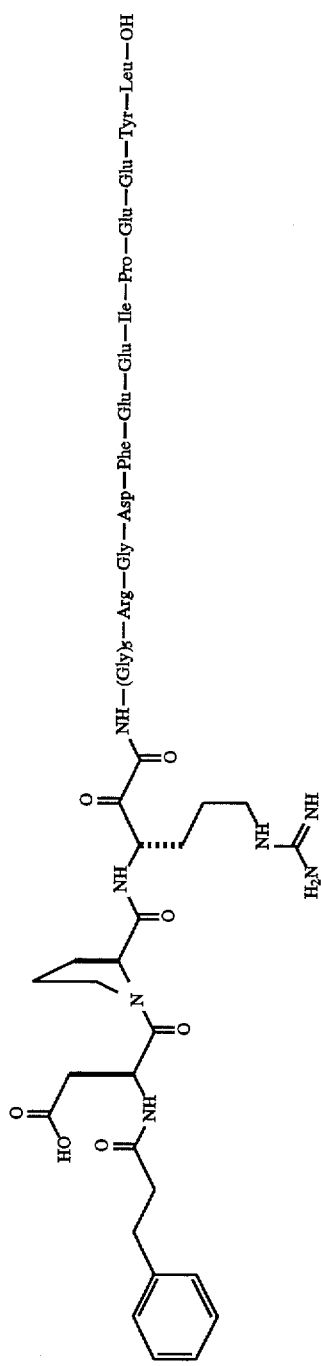
[27] [SEQ. ID. NO. 44]
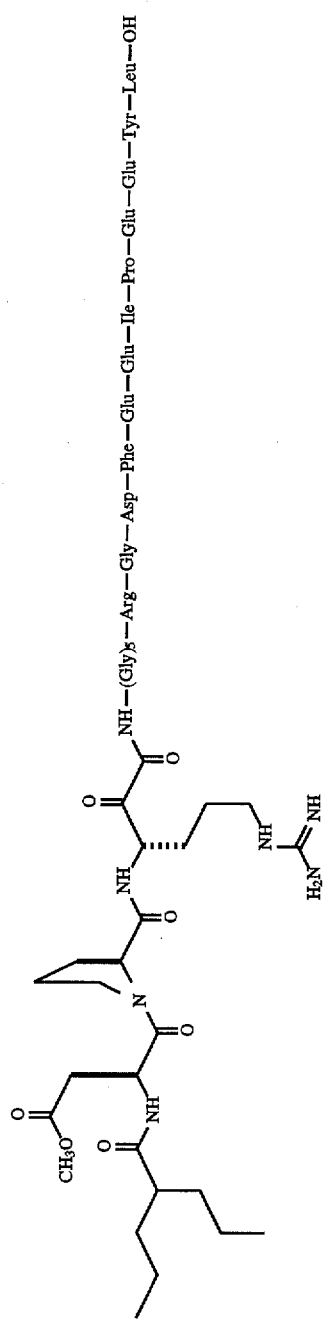

[28] [SEQ. ID. NO. 45]
[29] [SEQ. ID. NO. 46]
[30] [SEQ. ID. NO. 47]
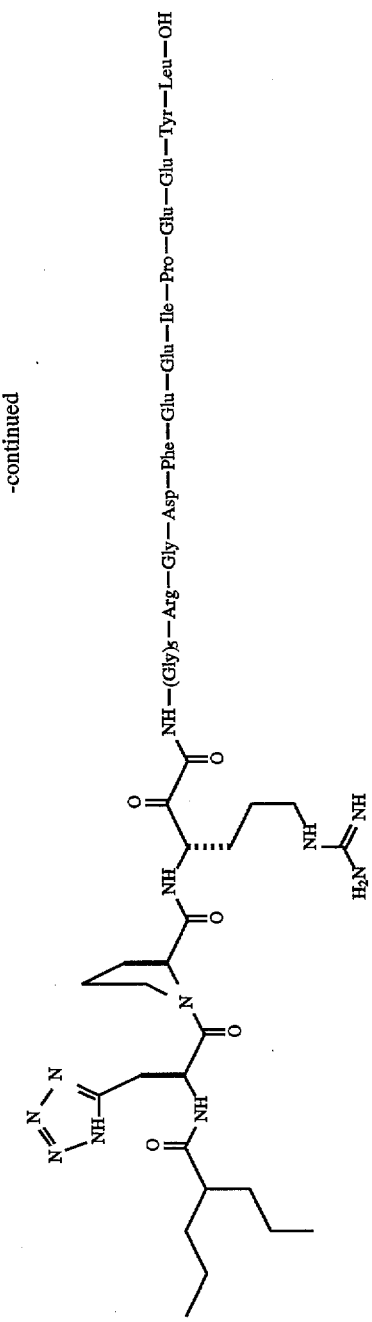
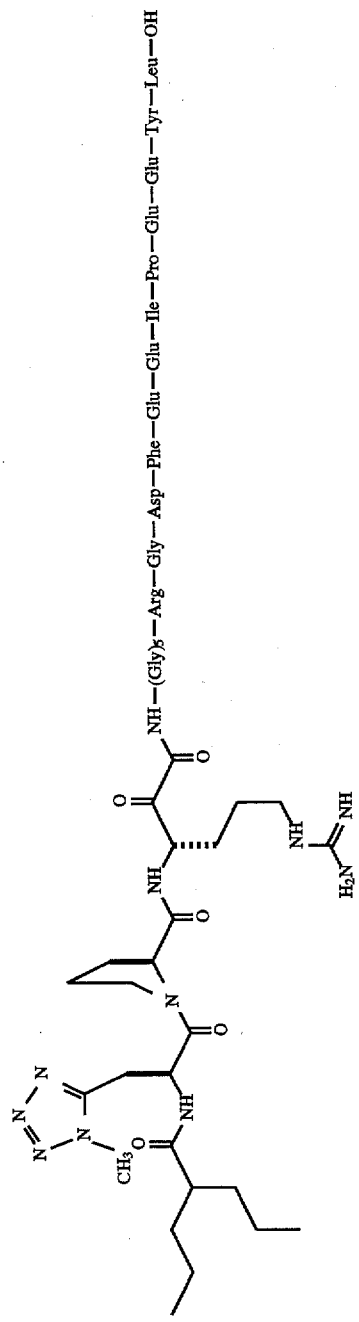
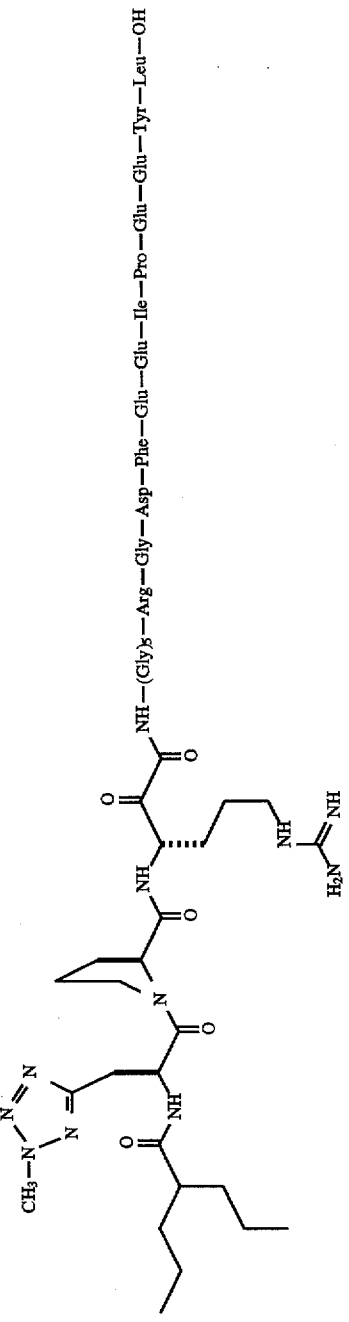

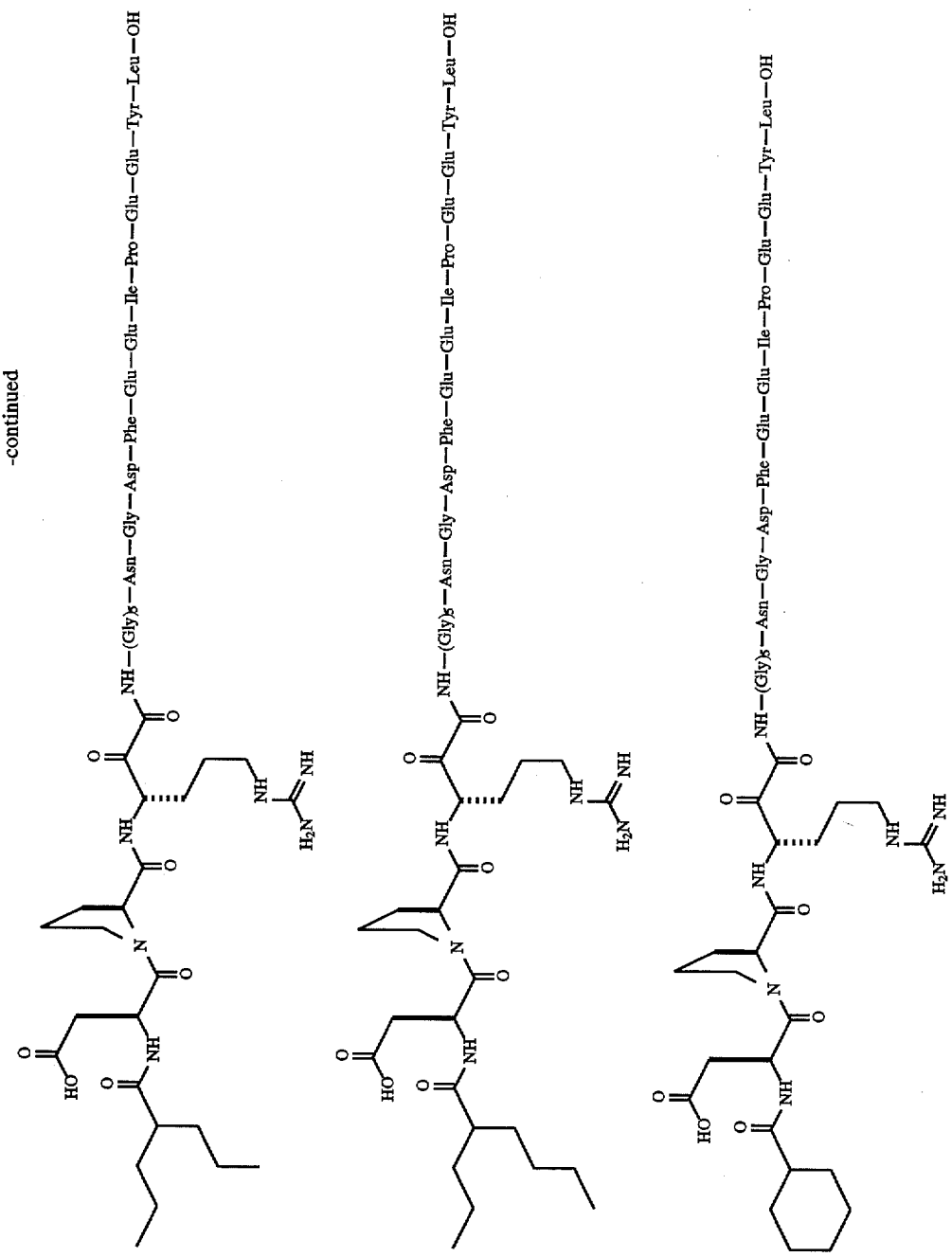

-continued
[34] [SEQ. ID. NO. 51]
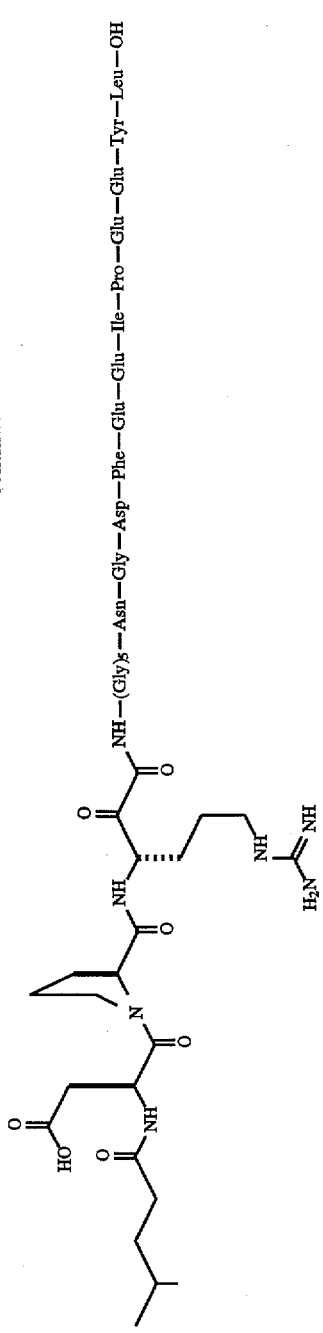
[35] [SEQ. ID. NO. 52]
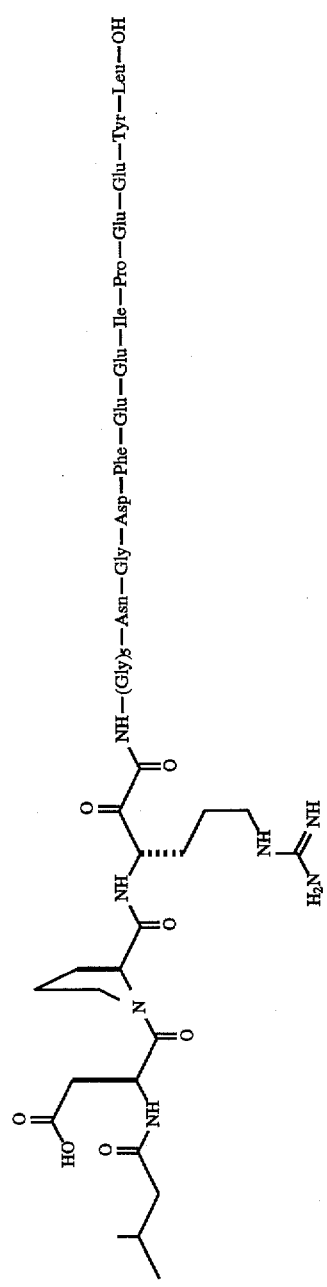
[36] [SEQ. ID. NO. 53]
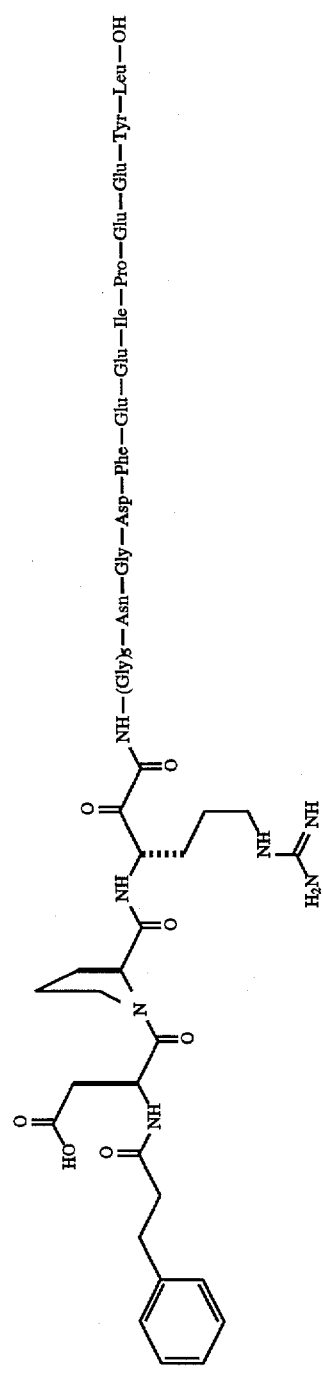

[37] [SEQ. ID. NO. 54]
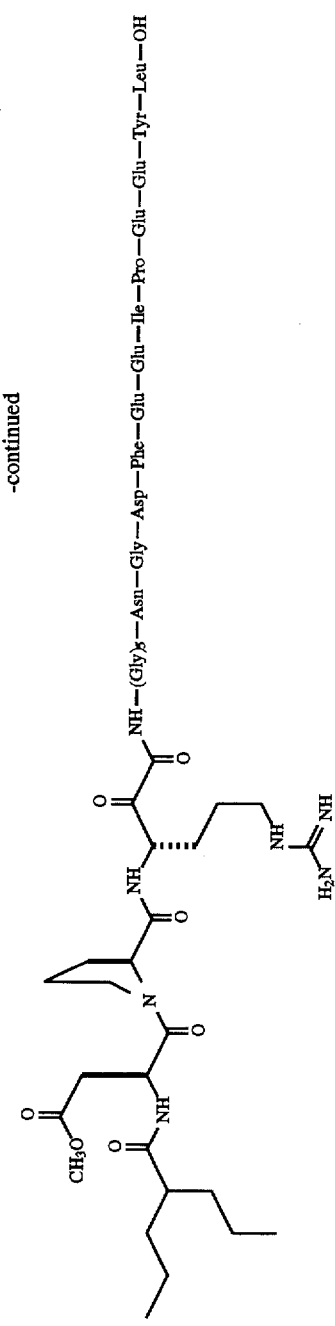
[38] [SEQ. ID. NO. 55]
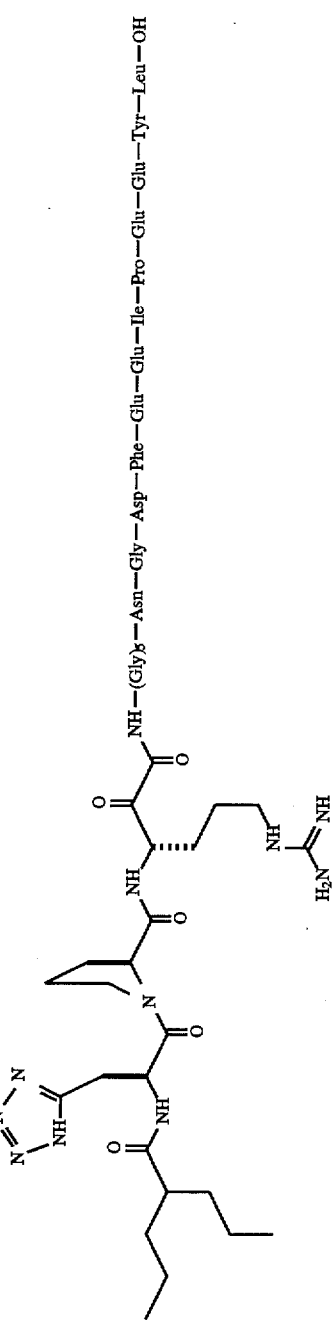
[39] [SEQ. ID. NO. 56]
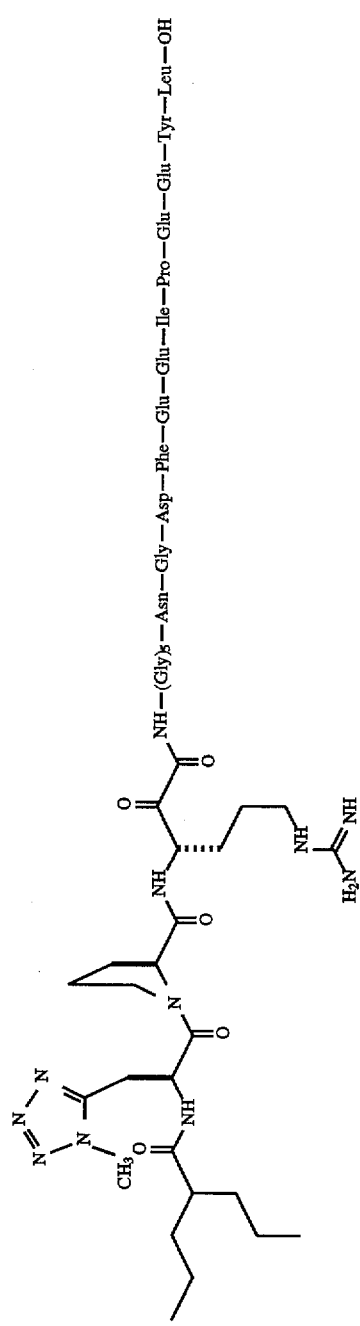

[40] [SEQ. ID. NO. 57]
[41] [SEQ. ID. NO. 58]
[42] [SEQ. ID. NO. 59]
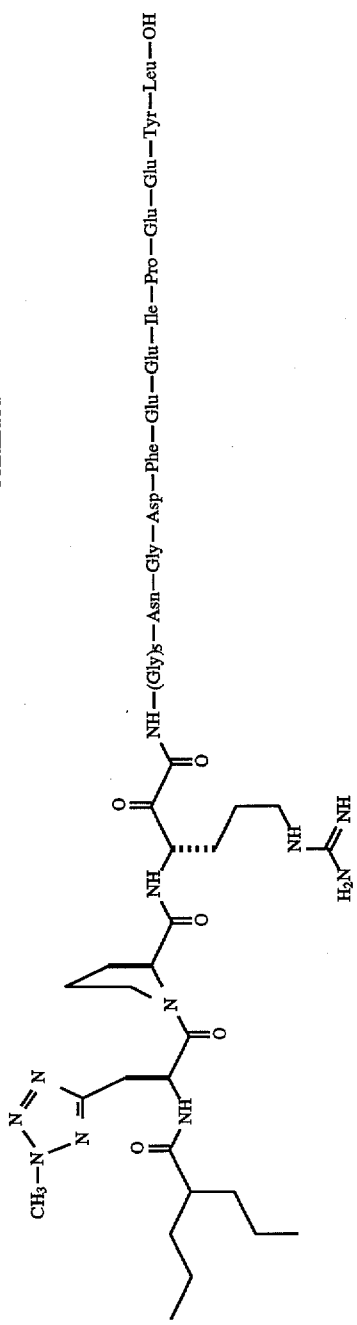
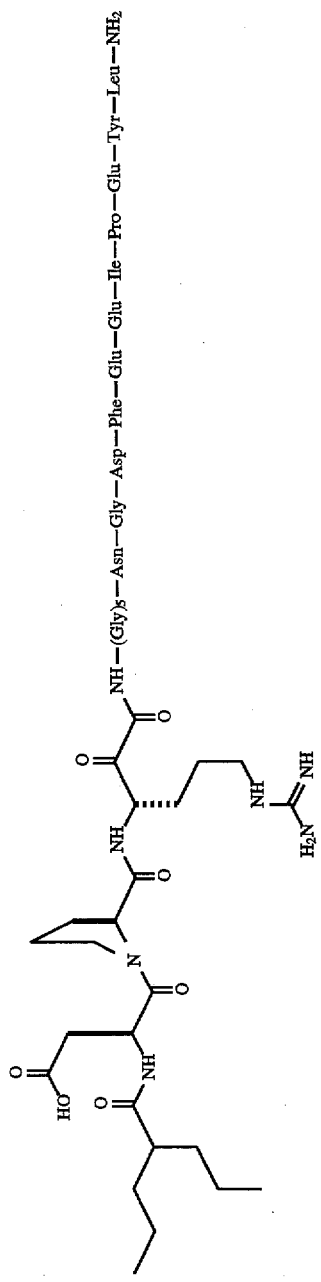
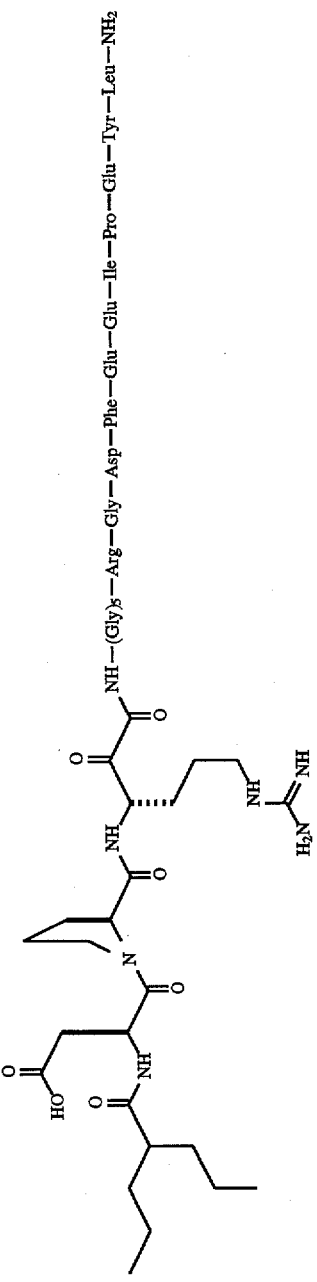

[43] [SEQ. ID. NO. 60]
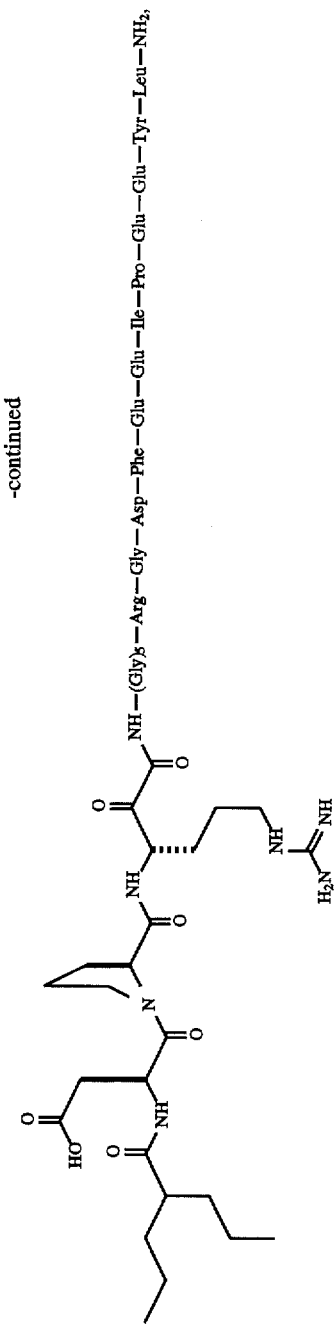
and
[44] [SEQ. ID. NO. 61]
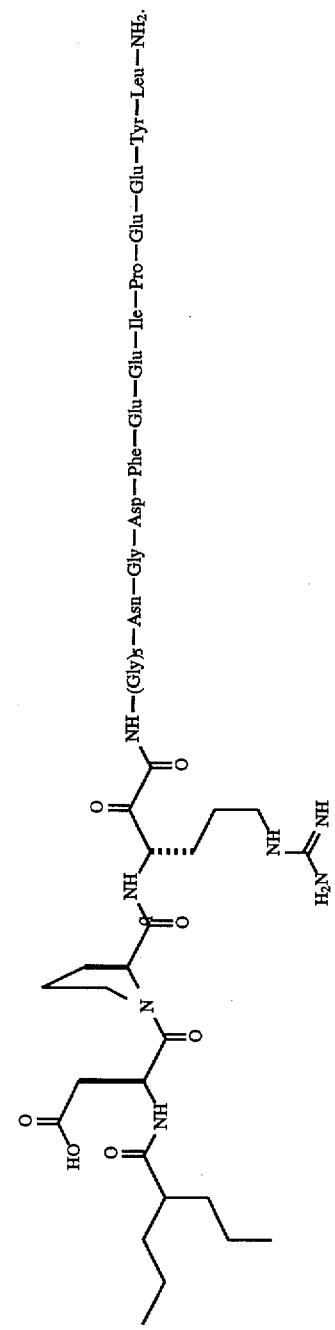

Preferred compounds of the present invention include:
[1] [SEQ. ID. NO. 18]
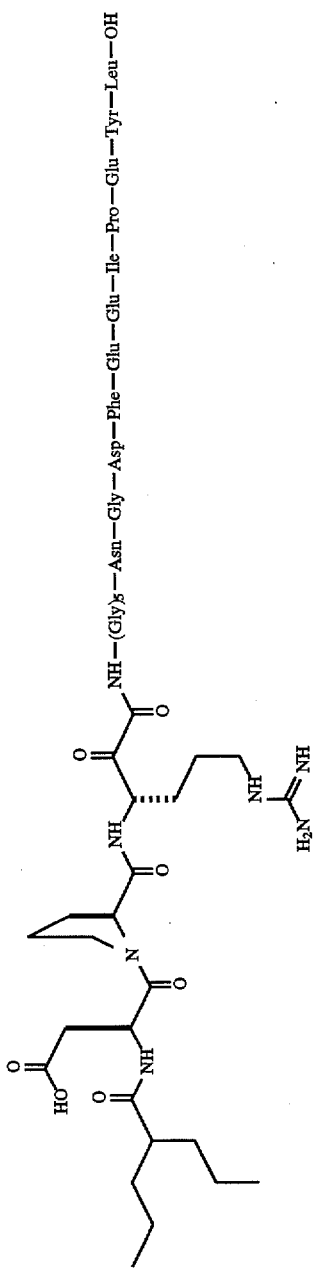
[11] [SEQ. ID. NO. 28]
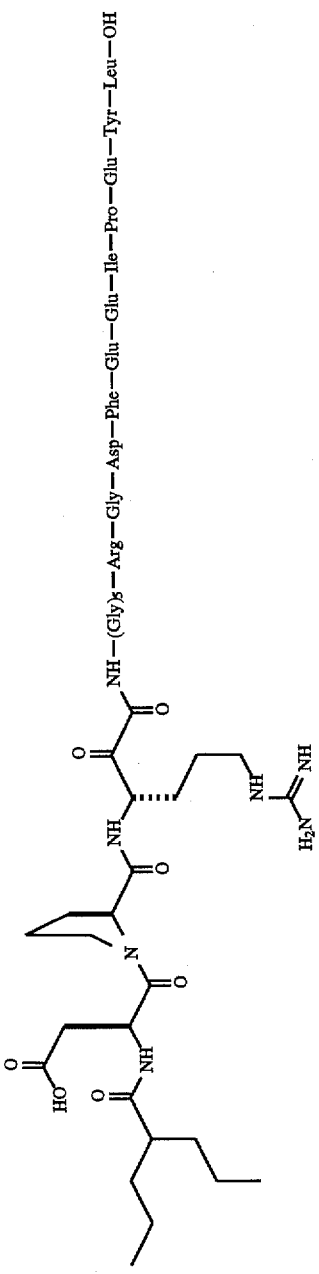
[21] [SEQ. ID. NO. 38]
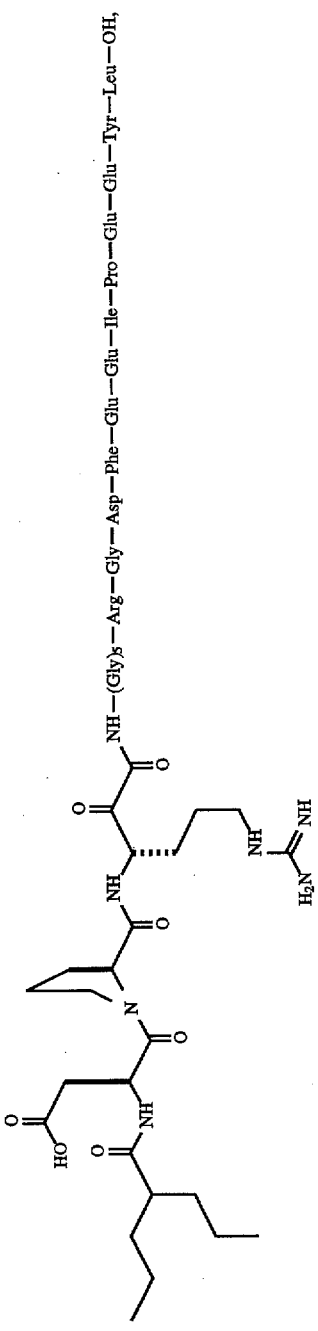
and -continued
[31] [SEQ. ID. NO. 48]
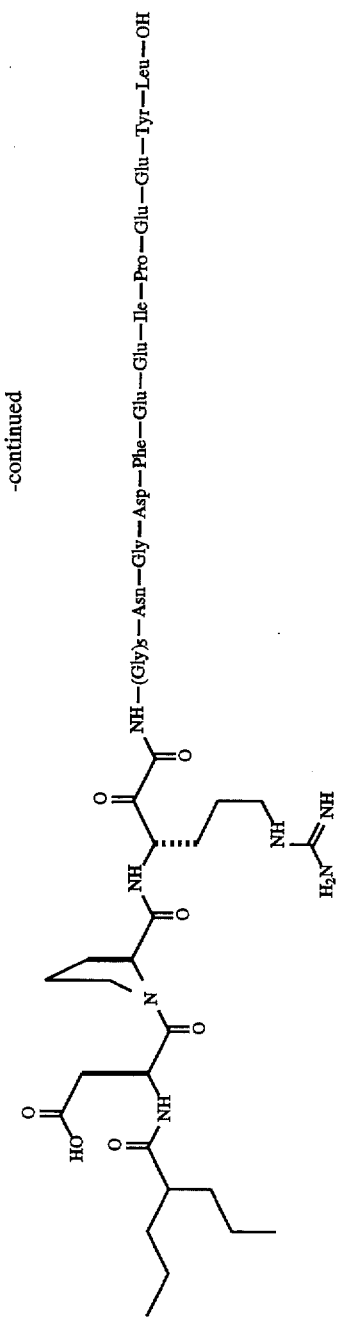

In another aspect, the present invention also provides a class of novel compounds useful for imaging of thrombi in a mammal. Preferred compounds that class include those of formula I, wherein m is 2;

B is -Gly-Gly-Gly-Gly-Gly-Asn-Gly-Asp-Phe- [SEQ. ID. NO. 62] or -Gly-Gly-Gly-Gly-Gly-Arg-Gly-Asp-Phe-; [SEQ. ID. NO. 63]

C is -Gly-Gly-Ile-Pro-Glu-Tyr(3-iodo)-Leu-OH, [SEQ. ID. NO. 64] -Glu-Glu-Ile-Pro-Glu-Tyr(3,5-diiodo)-Leu-OH, [SEQ. ID. NO. 65] -Glu-Glu-Ile-Pro-Glu-Tyr(3-iodo)-Leu-NH$_2$, [SEQ. ID. NO. 66] -Glu-Glu-Ile-Pro-Glu-Tyr(3,5-diiodo)-Leu-NH$_2$, [SEQ. ID. NO. 67] -Glu-Glu-Ile-Pro-Glu-Glu-Tyr(3-iodo)-Leu-OH, [SEQ. ID. NO. 68] -Glu-Glu-Ile-Pro-Glu-Glu-Tyr(3,5-diiodo)-Leu-OH, [SEQ. ID. NO. 69] -Glu-Glu-Ile-Pro-Glu-Glu-Tyr(3-iodo)-Leu-NH$_2$. [SEQ. ID. NO. 70] or -Glu-Glu-Ile-Pro-Glu-Glu-Tyr(3,5-diiodo)-Leu-NH$_2$, [SEQ. ID. NO. 71] wherein at least one of the iodine atoms therein is either I-123, I-125 or I-131;

R$_1$ is cyclohexyl, 4-heptyl, 3-methylpentyl, 2-methylpropyl, 3-octyl or 2-phenylethyl; and A is —CO$_2$H and —CO$_2$CH$_3$. Especially preferred are those compounds wherein B is -Gly-Gly-Gly-Gly-Gly-Asn-Gly-Asp-Phe- [SEQ. ID. NO. 72] or -Gly-Gly-Gly-Gly-Gly-Arg-Gly-Asp-Phe-, [SEQ. ID. NO. 73] and C is -Glu-Glu-Ile-Pro-Glu-Tyr(3-iodo)-Leu-OH, [SEQ. ID. NO. 74] -Glu-Glu-Ile-Pro-Glu-Tyr(3,5-diiodo)-Leu-OH, [SEQ. ID. NO. 75] -Glu-Glu-Ile-Pro-Glu-Glu-Tyr(3-iodo)-Leu-OH, [SEQ. ID. NO. 76] or -Glu-Glu-Ile-Pro-Glu-Glu-Tyr(3,5-diiodo)-Leu-OH; R$^1$ is 4-heptyl; [SEQ. ID. NO. 77] and A is —CO$_2$H.

In another aspect, the present invention provides another class of novel compounds which are useful for in vivo imaging of thrombi in a mammal. These compounds include those having formula II.

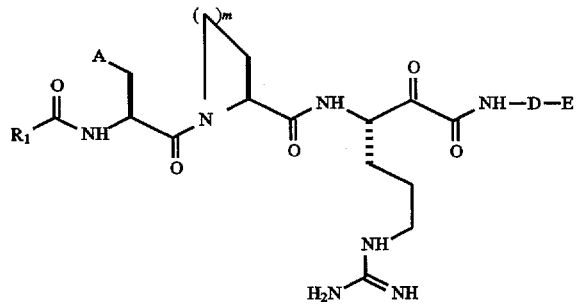

The compounds of formula II include those wherein m is 1, 2, or 3. The preferred compounds will have m equal to 1.

The compounds of formula II also include those wherein E is a peptide represented by the formula: E$_1$-E$_2$-E$_3$-E$_4$-E$_5$-E$_6$-E$_7$-Z, wherein E$_1$ is Glu; E$_2$ is Ala, Glu or Pro; E$_3$ is Ile, Leu or Ser; E$_4$ is Hyp, Leu or Pro; E$_5$ is Asp, Glu, Ala-Asp, Ala-Glu, Asp-Asp, Asp-. Glu, Glu-Asp or Glu-Glu; E$_6$ is Ala, Ile, Tyr(3-iodo), Tyr(3,5-diiodo), Tyr(O—SO$_3$H), Ala-Tyr(3-iodo), Ala-Tyr(3,5-diiodo), or Ala-Tyr(O—SO$_3$H); E$_7$ is Ala, Asp, Cha, Leu or Tyr; and Z is —OH or —NH$_2$. The preferred compounds will have E which is -Glu-Glu-Ile-Pro-Glu-Tyr-Leu-OH, [SEQ. ID. NO. 78] -Glu-Glu-Ile-Pro-Glu-Glu-Tyr-Leu-OH, [SEQ. ID. NO. 79] -Glu-Glu-Ile-Pro-Glu-Tyr-Leu-NH$_2$ [SEQ. ID. NO. 80] or -Glu-Glu-Ile-Pro-Glu-Glu-Tyr-Leu-NH$_2$ [SEQ. ID. NO. 81]. Especially preferred compounds will have E which is -Glu-Glu-Ile-Pro-Glu-Tyr-Leu-OH [SEQ. ID. NO. 82] or -Glu-Glu-Ile-Pro-Glu-Glu-Tyr-Leu-OH. [SEQ. ID. NO. 83]

The compounds of formula II include those wherein D is a peptide represented by D$_1$-D$_2$-D$_3$-D$_4$-D$_5$, wherein D$_1$ is (Gly)$_p$-X-(Gly)$_q$ when D$_2$ is Arg, Asn, Asp or Gln, or D$_1$ is -(Gly)$_{p+q}$-Gly- when D$_2$ is X, wherein p and q are independently selected from the integers, 1 to 7, such that their sum is 4 to 7; and X has the formula:

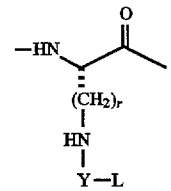

wherein r is an integer selected from 2 to 6, L is a chelating means for binding of a radioactive or paramagnetic atom, and Y is an attaching means for attaching chelating means; D$_3$ is Gly; D$_4$ is Asp; and D$_5$ is Nap, Phe, Tha, Trp or Tyr. The preferred compounds of the present invention will have D which is -Gly-Gly-X-Gly-Gly-Asn-Gly-Asp-Phe-, [SEQ. ID. NO.84] -Gly-Gly-X-Gly-Gly-Arg-Gly-Asp-Phe-, [SEQ. ID. NO. 85] or -Gly-Gly-Gly-Gly-Gly-X-Gly-Asp-Phe-, [SEQ. ID. NO. 86] Especially preferred are the compounds which have r equal to 4, or L-lysine.

In these compounds represented by formula II, the attaching means, Y, includes groups which are capable of covalently bonding with both the e-amino group of L-lysine and the chelating means. For example, Y may be —C(=S)—, —C(=O)—, —C(=NH)—(CH$_2$)$_6$—C(=NH)—, —C(=O)—(CH$_2$)$_6$—C(=O)—,

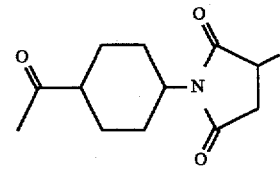

and the like. Especially preferred compounds will have a Y which is —C(=S)— or

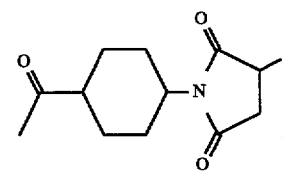

Also, in the compounds represented by formula II, the chelating means, L, includes groups capable of covalently bonding to Y and covalently or noncovalently binding to either a radioactive or paramagnetic atom. The chelating means include those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene group or by up to four separated ethylene units separated by a nitrogen or oxygen or sulfur atom. Preferred as a complexing means is diethylenetriamine-N, N,N',N",N"-pentaacetic acid (DTPA). DTPA is well known in the art as a chelating means for the radioactive atom indium-111 (In-111), technetium-99m (Tc-99m), and the paramagnetic atom gadolinium (Gd). Khaw, et al., Science, 209: 295 (1980); Paik C. H. et al., U.S. Pat. Nos. 4,652,440 (1987); Gries, H. et al., 4,957,939 (1990). Especially preferred for chelating means, L, is 1-(p-aminobenzyl) diethylenetriaminepentaacetic acid. Also included as chelating means are compounds which contain sulfhydryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The compounds of the present invention also include those wherein $R_1$ is an alkyl of about 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of about 1 to about 12 carbon atoms, alkenyloxy of about 3 to about 8 carbon atoms, aryloxy of about 6 to about 14 carbon atoms, or aralkyloxy of about 6 to about 15 carbon atoms. Compounds of formula II include those having an $R_1$ which is cyclohexyl, 4-heptyl, 3-methylpentyl, 2-methylpropyl, 3-octyl or 2-phenylethyl.

Preferred compounds will have an $R_1$ which is 4-heptyl.

The compounds of formula II also include those, wherein A is selected from the group consisting of

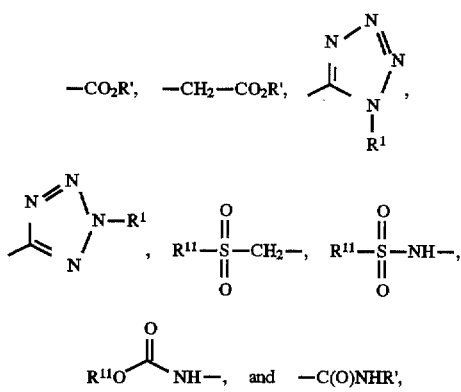

wherein R' is H, alkyl of 1 to about 6 carbon atoms, or aralkyl of about 6 to about 15 carbon atoms and R" is alkyl of 1 to 6 carbon atoms or aralkyl of about 6 to about 15 carbon atoms. The preferred compounds will have an A which is

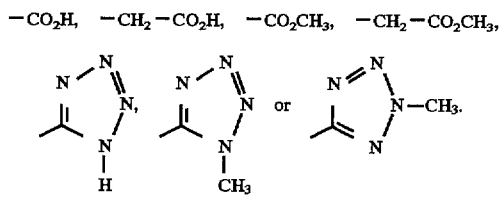

Especially preferred compounds will have an A which is —$CO_2H$.

The preferred compounds of formula I and II also include their pharmaceutically acceptable salts. The term "pharmaceutically acceptable salts" includes salts of compounds derived from the combination of a compound of formula I or II and an organic or inorganic acid. These compounds are useful in both free base and salt form. These salts include acid addition salts, for example, salts of hydrochloric, hydrobromic, acetic acid, and benzene sulfonic acid and the like. In practice, the use of the salt form amounts to use of the base form; both forms are within the scope of the present invention.

B. Preparation

The preferred compounds of the present invention can be synthesized using conventional preparative and recovery methods known to those skilled in the art of peptide synthesis. Solid phase or liquid phase methods, or both can be utilized.

A preferred synthesis route for the straight-chain peptide intermediates, especially the smaller peptides (of shorter chain length, that is, having from about 3 to about 50 amino acid residues) of the invention is the solid phase method. This method is well known in the art and is described in references such as Merrifield, J., Am. Chem. Soc. 85: 2149–2154 (1963); Science 150: 178–185 (1965); and Science 232: 341–347 (1986); Vale et al., Science 213: 1394–1397 (1981); and Marke et al., J. Am. Chem. Soc. 103: 3178 (1981). Other preparative methods which may be employed include the processes of Houghten, Proc. Natl. Acad. Sci(USA) 82: 5132 (1985). Further background information on established solid phase synthesis procedures which can be used for the preparation of the compounds described herein is set forth in the treatise by Stewart and Young, Solid Phase Peptide Synthesis, W. H. Freeman & Co., San Francisco, 1969; in the review chapter by Merrifield, J., Advances in Enzymology, Vol. 32, pp 221–296, Interscience Publishers, New York, (F. F. Nold, E., 1969); and in Erickson and Merrifield, The Proteins, Vol. 2, p 255 et seq., Academic Press, New York, ((Neurath and Hill ed. 1976).

Solid phase peptide synthesis is generally commenced from the C-terminus of the peptide by coupling a protected a-amino acid to a suitable resin, such as Fmoc-amino acid-4-(hydroxymethyl)phenoxymethylcopoly (styrene-1% divinylbenzene) resin (Wang resin), Boc-amino acid-4-(oxymethyl)-phenylacetamidiomethyl copoly (styrene-1% divinylbenzene) resin (PAM resin), hydroxymethylphenoxymethyl polystyrene resin (HMP resin) or a RINK ([dimethoxyphenyl-Fmoc aminomethyl]phenoxy resin) resin. The RINK resin is a modified benzhydrylamine resin that contains ortho and para electron-donating methoxy groups.

In the solid phase method, the compounds of the present invention can be synthesized by sequential coupling of protected amino acid derivatives onto a solid phase using the reagents known in the art. Such reagents are readily available from chemical vendors as Aldrich, Sigma, Nova Biochemicals, Advanced ChemTech, Bachem and the like.

During the solid phase synthesis of the compounds of the present invention, the functional groups of the requisite amino acid derivatives or analogs used are protected by blocking groups to prevent cross reaction during the coupling procedure. As such, they are referred to herein as protected amino acids or amino acid analogs. Examples of suitable blocking groups and their use are described in The Peptides: Analysis, Synthesis, Biology, Academic Press, Vol. 3 (E. Gross & Meienhofer edit. 1981) and Vol. 9 (S. Udenfriend & J. Meienhofer edit. 1987).

A suitably protected amino acid or amino acid analog will have blocking groups on its a-amino group and, if necessary, on its side chain functionality. Examples of suitable blocking groups for the a-amino group include acyl protecting groups, for example, formyl, acetyl, benzoyl, trifluoroacetyl, succinyl and methoxysuccinyl aromatic urethane protecting groups, for example, benzyloxycarbonyl and aliphatic urethane protecting groups, for example, tert-butyloxycarbonyl (Boc), adamantyloxycarbonyl or fluorenylmethyloxycarbonyl (Fmoc) groups. Numerous suitable amino terminal protecting groups are known. See, for example, The Peptides, Vol. 3, pp 3–88. Other suitable protecting groups are known to those skilled in the art. The preferred amino terminal protecting groups include t-butyloxycarbonyl (Boc) and 9-fluorenymethyloxycarbonyl (Fmoc).

The sequential coupling of protected amino acids or amino acid analogs to the solid phase or growing peptide chain on the solid phase comprises converting the free carboxyl group of the protected amino acid or amino acid analog to an "activated" derivative wherein its carboxyl group is rendered more susceptible to reaction with the free N-terminal a-amino group of the target amino acid or peptide having an associated a-keto amide functionality. For example, the free carboxyl of the a-amino protected (N-protected) amino acid can be converted to a mixed anhydride by reaction of a N-protected amino acid with ethyl choloroformate, pivaloyl chloride or like acid chlorides. Alternatively, the carboxyl of the a-amino protected amino acid can be converted to an active ester such as a 2,4,5-trichloropheyl ester, a pentachlorophenol ester, a pentafluorophenyl ester, a p-nitrophenyl ester, a N-hydroxysuccinimide ester, or an ester formed from 1-hydroxybenzotriazole. Another coupling method involves use of a suitable coupling agent such as N,N'-dicyclohexylcarbodiimide or N,N'-diisopropylcarbodiimide. Other appropriate coupling agents are disclosed in *The Peptides: Analysis, Structure, Biology*, Vol. I: "Major Methods of Peptide Bond Formation", Academic Press, New York, E. Gross & J. Meinenhofer edits, 1979).

The preferred method of solid phase coupling uses either t-Boc-protected amino acids or amino acid analogs or Fmoc protected amino acids or amino acid analogs which are coupled to the N-terminus free a-amino of the growing peptide chain attached to the solid phase resin. In this method, the coupling reagents include 1-hydroxybenzotriazole (HOBT) and 2-(1H-benzotriazol-1-yl)-1,1,3,3 tetramethyluronium hexafluorophosphate (HBTU), dicyclohexylcarbodiimide (DCC) or BOP, either alone or in combination with 1-hydroxybenzotriazole (HOBT). Preferred methods as discussed above are described in Example 1.

A preferred method of preparation of the compounds Of the present invention involves the use of the amino acid analog, 6-nitroguanidino-3-(S)-(1,1-dimethylethoxy) methanamido-2-hydroxyhexanoic acid. This intermediate of the present invention is depicted in formula III below:

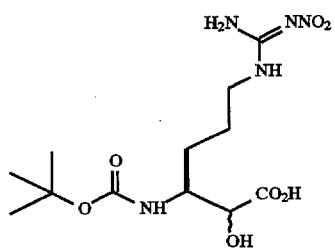

FIG. 1 illustrates the preferred method of synthesis of this intermediate, which is explained in detail in Examples 2 to 7. In FIG. 1, "i" represents potassium cyanide, potassium bicarbonate, water; "ii" represents HCl/water/dioxane; "iii" represents dry HCl/methanol; "iv" represents $Boc_2O/THF/NaHCO_3/H_2O/$; "v" represents lithiumhydroxide/methanol/water; and "vi" represents Dowex-50 acid form.

The coupling of requisite amino acids, amino acid analogs and other groups to the solid phase gives an intermediate of the present invention, the peptide-solid phase as shown in formula IV below:

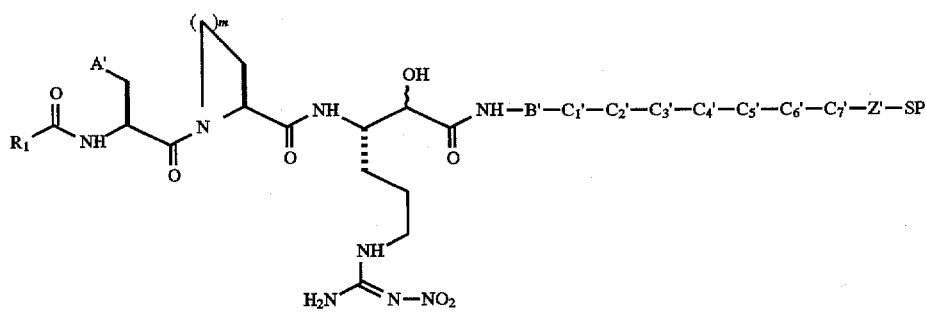

wherein $R_1$ and m are defined as for formula T above; A' is selected from the group consisting of

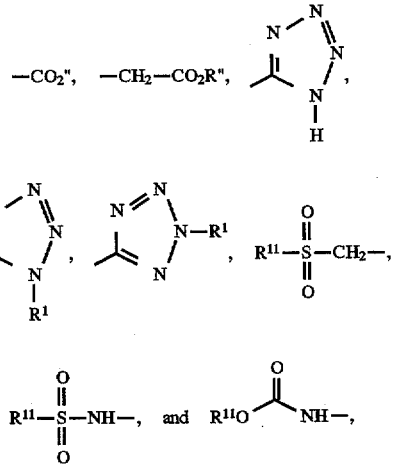

wherein R" is alkyl of 1 to about 6 carbons, or aralkyl of about 6 to about 15 carbon atoms;

B' is a peptide represented by the formula: $B_1'$-$B_2'$-$B_3'$-$B_4'$-$B_5'$, wherein $B_1'$ is peptide of 5 to 8 amino acids whose side chain group is protected, or $B_1'$ is $(Gly)_p$-X-$(Gly)_q$ when $B_2'$ is Arg, Asn, Asp or Gln whose side chain group is protected, or $B_1'$ is -$(Gly)_{p+q}$-Gly- when $B_2'$ is X, wherein p and q are independently selected from the integers, 1 to 7, such that their sum is 4 to 7, and X has the formula:

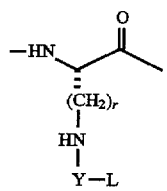

wherein r is an integer selected from 2 to 6, L is a chelating means for binding of a radioactive or paramagnetic atom, and Y is an attaching means for attaching chelating means;

$B_2'$ is Arg, Asn, Asp or Gln whose side chain group is protected;

$B_3'$ is Gly;

$B_4'$ is Asp whose side chain group is protected; and $B_5'$ is Nap, Phe, Tha, Trp or Tyr whose side chain group is protected;

$C_1'$ is Glu whose side chain group is protected;

$C_2'$ is Ala, Glu or Pro whose side chain group is protected;

$C_3'$ is Ile, Leu or Ser whose side chain group is protected;

$C_4'$ is Hyp, Leu or Pro whose side chain group is protected;

$C_5'$ is Asp, Glu, Ala-Asp, Ala-Glu, Asp-Asp, Asp-Glu, Glu-Asp or Glu-Glu whose side chain groups are protected;

$C_6'$ is Ala, Ile, Tyr, Tyr(O-SO$_3$H), Tyr(3-iodo), Tyr(3,5-diiodo), Ala-Tyr, Ala-Tyr(O-SO$_3$H), Ala-Tyr(3-iodo) or Ala-Tyr(3,5-diiodo) whose side chain group or groups are protected;

$C_7'$ is Ala, Asp, Cha, Leu or Tyr whose side chain group is protected;

Z' is —O— or —NH—; and

SP is a solid phase insoluble in solvents and solutions employed in solid phase peptide synthesis.

A "side chain group" of an amino acid refers to its substituent on the a-carbon which characterizes the amino acid. Among these side chain groups, some must be protected to prevent side reactions involving their substituent groups during peptide synthesis, for example, when they are used in the tBoc or Fmoc coupling chemistries. Side chain groups having substituent groups that must be protected to be useful in these peptide synthesis methods include those associated with Arg, Asn, Asp, Cys, Gln, Glu, His, Lys, Orn, Ser, Thr, Trp and Tyr. Typical protecting groups are shown in the Examples provided hereinunder. Other protecting groups are known in the art.

The hydroxy group incorporated into the intermediate represented by formula IV by coupling of the compound of formula III may be oxidized to a keto group by treatment with oxidant to provide yet another intermediate of the present invention represented by formula V below.

wherein, $R_1$, m, A', B', $C_1'$, $C_2'$, $C_3'$, $C_4'$, $C_5'$, $C_6'$, $C_7'$, Z' and SP are as defined for the intermediates represented by formula IV.

Upon completion of the coupling of requisite amino acids, amino acid analogs and other groups to give an intermediate of the present invention, a peptide-solid phase, the hydroxy group incorporated therein by coupling of the compound of formula III may be oxidized to a keto group by treatment with oxidant to provide yet another intermediate of the present invention. In the preferred method of oxidation, a peptide-solid phase is treated with EDAC-HCl and DCA in dry dichloromethane and dry dimethylsulfoxide, the details of which are given in Example 8. The oxidation of a-hydroxy acids using these reagents in a liquid phase system has been described in Edwards et al., J. Am. Chem. Soc., 114: 1854 at 1861 (1992).

After the desired peptide sequence is completed, the intermediate peptide is cleaved from the resin and the protecting groups are removed. Cleavage/deprotection methods would include the treatment of the resin-bound peptide with reagents such as hydrofluoric acid containing anisole or trifluoroacetic acid containing phenol, EDT and thioanisole. The preferred method of cleavage from the resin and deprotection is described in Example 8.

The desired peptide is isolated from the cleavage/deprotection solution by techniques such as filtration, centrifugation or extraction with diethyl ether. The peptide can then be purified by high performance liquid chromatography (HPLC) or other such methods of protein purification.

Exemplars of the preparation of the some of compounds of the present invention are found in Examples 8, 10 through 14, 19 through 22, and 34 through 40.

The compounds of the present invention are distinguished by their ability to inhibit the catalytic activity of thrombin. The compounds of the present invention may be prepared for assay by dissolving them in buffer to give solutions containing concentrations such that assay concentrations range from 0 and 100 mM in one assay. In the assay to determine the inhibitor constant, Ki, for a compound of the present invention, chromogenic synthetic substrate for thrombin is added to a solution containing test compound and thrombin and the catalytic activity of the enzyme is determined spectrophotometrically. A preferred method of determining Ki is shown in Example A.

Preferred compounds of the present invention have a Ki of less than about 0.050 nM, particularly in this thrombin assay or an equivalent assay.

Another aspect of the present invention provides compounds which are which are useful for in vivo imaging of thrombi in a mammal, wherein the compound represented by formulas I or II is covalently labelled with a radioactive atom.

V

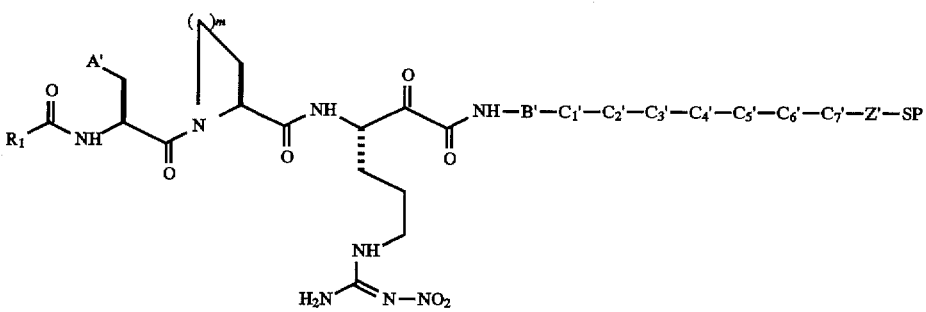

A radioactive iodine isotope such as I-123, I-125, or I-131 may be covalently attached to the tyrosine group of the compounds of formula I using radioactive sodium or potassium iodide and a chemical oxidizing agent, such as sodium hypochlorite, chloramine T, or the like, or by an enzymatic oxidizing system, such as lactoperoxidase, glucose oxidate and glucose, or using Boulton Hunter reagent. An embodiment of these compounds of the present invention and their preparation is disclosed in Example 24.

As described above, the compounds of the present invention as depicted in formula II include those wherein $D_1$ is $(Gly)_p$-X-$(Gly)_q$ when $D_2$ is Arg, Ash, Asp or Gln, or $D_1$ is -$(Gly)_{p+q}$-Gly- when $D_2$ is X, wherein p and q are independently selected from the integers, 1 to 7, such that their sum is 4 to 7, and X has the formula:

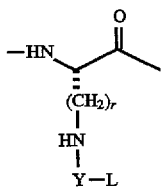

wherein r is an integer selected from 2 to 6, L is a chelating means for binding of a radioactive or paramagnetic atom, and Y is an attaching means for attaching chelating means. These compounds may be prepared using the methods disclosed above and those disclosed in Examples 26 thorugh 31.

Compositions and Their Preparation

A. Pharmaceutical Compositions

The compositions and pharmaceutical compositions comprising the compounds of formula I of the present invention are functional inhibitors of thrombin, and can be used to prevent or treat a pathological condition characterized by thrombus formation.

Pathological conditions characterized by thrombus formation include those involving the arterial and venous vasculature. With respect to the coronary. arterial vasculature, thrombus formation may result from the rupture of an established atherosclerotic plaque. Such thrombosis is the major cause of acute myocardial infarction and unstable angina, as well as also characterizing the reocclusive coronary thrombus formation following either thrombolytic therapy or percutaneous transluminal coronary angioplasty (PTCA).

With respect to the venous vasculature, thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. A systemic form of abnormal activation of coagulation is designated disseminated intravascular coagulopathy and commonly occurs within both vascular systems during septic shock, certain viral infections and cancer; it is a condition wherein there is rapid consumption of coagulation factors and systemic coagulation which results in the formation of life-threatening microvascular thrombi occurring throughout the vasculature leading to widespread organ failure.

Accordingly, the present invention provides pharmaceutical compositions for preventing or treating a pathological condition in a mammal characterized by thrombus formation. These pharmaceutical compositions are comprised of a therapeutically effective amount of compound or compounds of the present invention and a pharmaceutically acceptable carrier. The "therapeutically effective amount" of the composition required as a dose will depend on the route of administration, the type of mammal being treated, and the physical characteristics of the specific mammal under consideration. These factors and their relationship to determining this dose are well known to skilled practitioners in the medical arts. Also, the therapeutically effective amount and method of administration can be tailored to achieve optimal efficacy but will depend on such factors as weight, diet, concurrent medication and other factors which those skilled in the medical arts will recognize. Preferred as a "therapeutically effective amount" for a daily dose of the pharmaceutical composition is between about 1 μg/kg body weight of a mammal to be treated to about 5 mg/kg body weight of a compound or compounds of the present invention.

The pharmaceutical compositions of the present invention containing a therapeutically effective amount of the compounds of the present invention may be formulated with a pharmaceutically acceptable carrier to provide sterile solutions, suspensions for injectable administration; and the like. In particular, injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized. Pharmaceutically acceptable carriers or diluents for therapeutic use are well known in the pharmaceutical art, and are described, for example, in Remington's Pharmaceutical Sciences, Mack Publishing Co. (A. R. Gennaro edit. 1985).

The present invention also encompasses pharmaceutical compositions prepared for storage or administration. These would additionally contain preservatives, stabilizers, and dyes. For example, sodium benzoate, sorbic acid and esters of p-hydroxybenzoic acid may be added as preservatives. Id. at 1449. In addition, antioxidants and suspending agents may be used. Id.

B. Compositions Containing Radioactive Atoms

The present invention also includes compositions which are useful for in vivo imaging of thrombi in a mammal, wherein the compositions are comprised of a compound of formula I or II complexed with a radioactive atom.

Compounds of formula I can be labelled with radioactive iodine as described above.

For the compounds of formula II, suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. It is a gamma emitter, and has a single photon energy of 140 keV, a half-life of about 6 hours, and it is readily available from a Mo-99/Tc-99 generator. Rhenium-186 and -188 also have gamma emission which allows it to be imaged. Preferred compositions contain the radioactive atom, Tc-99m.

Compositions of the present invention are conveniently prepared by complexing a compound of formula II with radioisotopes which are suitable for detection externally.

The gamma emitters, indium-111 and technetium-99m, are preferred as radioactive atoms because they are detectable with a gamma camera and have favorable half-lives in vivo.

The compounds FIG. II can be labelled by any of the many techniques known in the art to provide a composition of the present invention. For example, these compounds can be labelled through a chelating agent such as diethylenetriaminepentaacetic acid (DTPA) or metallothionein, both of which can be covalently attached to the compound of formula II.

In general, the compositions of the present invention containing technetium-99m are prepared by forming an aqueous mixture of technetium-99m and a reducing agent and a water-soluble ligand, and then contacting the mixture with a compound of the present invention represented by formula II. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of formula II having a DTPA chelating means with technetium-99m. This may be accomplished behind a lead shield by combining a predetermined amount (as 5mg to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2–0.22 micron), then is dispensed into 0.9% saline for injection, if desired.

Another embodiment of the compositions of the present invention is prepared by labeling a compound of formula II having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the formula II having a metallothionein attached thereto. After incubating the mixture for a period of time and under conditions which allow for an exchange of the technetium-99m from the glucoheptonate complex to the metallothionein of the compound of formula II, the technetium-labeled composition of the present invention is formed. In particular, an exemplar of this composition and its preparation is disclosed in Example 32.

The source of technetium-99m should preferably be water soluble. Preferred sources are alkali and alkaline earth metal pertechnetate ($TcO_4^-$). Technetium-99m is most preferably obtained in the form of fresh sodium pertechnetate from a sterile technetium-99m generator (as from a conventional Mo-99/Tc-99m generator). However, any other source of physiologically acceptable technetium-99m may be used.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of formula II in this radioisotope's reduced state. For example, stannous chloride ($SnCl_2$) is the reducing agent and can used in range from 1–1,000 mg/mL. Especially preferred concentrations are about 30–500 mg/mL.

Citric acid complexes with technetium-99m quickly to form a stable technetium-99m-citrate complex. Upon contact with a compound of formula II, substantially quantitative transfer of technetium-99m from its citrate complex to the chelating means of the compound of formula II is achieved rapidly and under mild conditions. The amount of citric acid (as sodium citrate) can range from about 0.5 mg/ml up to the amount maximally soluble in the medium. Preferred amounts of citric acid range from 15 to 30 mg/ml.

The amount of compound of formula II having a chelating means can range from 0.001 to about 3 mg/mL, preferably about 0.017 to about 0.15 mg/mL. Finally, technetium-99m in the form of pertechnetate can be used in amounts of preferably about 1–50 mCi. The amount of mCi per mg of compound of the present invention is preferably about 30–150.

The reaction between the compound of formula II and the metal ion-transfer ligand complex is preferably carried out in an aqueous solution at a pH at which the compound of formula II is stable. By "stable", it is meant that the compound remains soluble and retains its inhibitory activity against a-thrombin. Normally, the pH for the reaction will be from about 5 to 9, the preferred pH being about 6–8. The technetium-99m-citrate complex and a compound of formula II are incubated, preferably at a temperature from about 20° C. to about 60° C., most preferably from about 20° C. to about 37° C., for a sufficient amount of time to allow transfer of the metal ion from the citrate complex to the chelating means of the compound of formula II. Generally, less than one hour is sufficient to complete the transfer reaction under these conditions.

Alternative compositions of the present invention include a In-111 labeled compound of the present invention. An embodiment of these compositions and its preparation is disclosed in Example 33. This exemplar teaches conditions for preparation of In-111 complex with a compound of formula II which has thereon a DTPA chelating means.

C. Compositions Containing Paramagnetic Atoms

The present invention also includes compositions of the compounds of the present invention which are useful for in vivo imaging of thrombi in a mammal, comprised of a compound represented by formula II complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium (III) and ytterbium(III). Because of their very strong magnetic moments, gadolinium(III), terbium(III), dysprosium (III), holmium(III), and erbium(III) are preferred. Especially preferred for the paramagnetic atom is gadolinium(III).

The compositions of the present invention may be prepared by combining a compound of formula II with a paramagnetic atom. For example the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of formula II in a similar aqueous medium and stirred. The reaction mixture may be heated moderately until the reaction is completed insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The compositions of the present invention may be isolated by crystallization by adding solvents soluble in water as lower alcohols (methyl, ethyl, isopropyl alcohol), lower ketones (acetone), polar ethers (tetrahydrofuran, dioxane, 1,2-dimethoxyethane) to an aqueous solution containing the compositions of the present invention.

D. Diagnostic Compositions

The present invention also includes diagnostic compositions which are useful for in vivo imaging of thrombi in a mammal, comprising a pharmaceutically acceptable carrier and a diagnostically effective amount of compositions derived from the compounds of formula I or II. Compositions such as those described in paragraphs B and C hereinabove may be conveniently used in these diagnostic compositions.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medical diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition of the present invention be about 5 to 20 mCi, preferably about 10 mCi. Magnetic resonance imaging will require that the dose provided be about 0.001 to 5 mmole/kg, preferably about 0.005 to 0.5 mmole/kg of a compound of formula II complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences*, Mack Publishing Co. (A. R. Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. at 1449. In addition, antioxidants and suspending agents may be used. Id.

Methods of Use

A. Therapeutic Methods

The methods of the present invention offer a significant advantage over the previous methods of preventing and arresting in vivo thrombus formation in mammals known in the art. This advantage is based on the fact that the compounds, composition and pharmaceutical compositions of the present invention are extremely potent inhibitors of thrombin which are not proteolytically degraded by thrombin. Because this provides a long-lasting inhibitory effect on abnormal thrombus formation in vivo, the present invention thereby provides novel methods useful for preventing or treating in a mammal a pathological condition characterized by thrombus formation.

According to one embodiment of the present invention, a method is provided for treating or preventing in a mammal a pathological condition characterized by thrombus formation comprising administering to said mammal a therapeutically acceptable amount of the compound or pharmaceutical composition of the present invention.

In employing the compounds, compositions or pharmaceutical compositions in vivo by this method, administering can be accomplished in a variety of ways, including parenterally, employing a variety of dosage forms. As will be apparent to one skilled in the art, the useful in vivo dosage to be administered and the particular mode of administration will vary depending upon the age, weight and mammalian species treated, the particular compounds employed, and the specific use for which these compounds are employed. Furthermore, the compounds, compositions or pharmaceutical compositions can be administered alone or in combination with one another, or in combination with other therapeutic or diagnostic agents.

The compounds, compositions or pharmaceutical compositions can be administered in vivo, ordinarily in a mammal, preferably in a human, or in vitro.

The determination of the "therapeutically effective amount" or effective dose of the compound, composition or pharmaceutical composition, that is, the dosage levels necessary to achieve the desired result, will be within the ability of one skilled in the medical arts. This dose will depend on the route of administration, the type of mammal being treated, and the physical characteristics of the specific mammal under consideration. These factors and their relationship to determining this dose are well known to skilled practitioners in the medical arts. Also, the therapeutically effect amount and method of administration can be tailored to achieve optimal efficacy but will depend on such factors as weight, diet, concurrent medication and other factors which those skilled in the medical arts will recognize. Preferred as a "therapeutically effective amount" for a daily dose of the pharmaceutical composition is between about 1 mg/kg body weight of a mammal to be treated to about 5 mg/kg body weight of the compound or compounds of the present invention. Typically, administration is commenced at lower dosage levels, with dosage levels being increased until the desired effect is achieved. Once dosage ranges are established, these compositions may be given as a bolus, followed by intraveneous administration at a predetermined rate.

B. Diagnostic Methods.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions or diagnostic compositions of the present invention into a convenient and accessible vein or artery. This includes but is not limited to administration by the antecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by formula II having a chelating means attached thereto may be injected into the mammal, followed at a later time by the radioactive atom thereby forming in vivo at the site of the thrombus the composition comprising the compound of formula II complexed to radioactive atom. Alternatively, a composition comprising the compound of formula II complexed to radioactive atom may be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. In any regard, the dose for in vivo imaging should be sufficient for detecting the presence of the imaging agent at the site of a thrombus in question. Typically, radiologic imaging will require that the dose provided by the diagnostic composition of the present invention be about 5 to 20 mCi, preferably about 10 mCi. Magnetic resonance imaging will require that the dose provided by the diagnostic composition be about 0.001 to 5 mmole/kg, preferably about 0.005 to 0.5 mmole/kg of a compound of formula II complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

To assist in understanding the present invention, the following examples are included which describe the results of a series of experiments. The following examples relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

General Solid-Phase Synthesis Methods

The solid phase syntheses of the compounds of the present invention were performed using an Applied Biosystems Model 430A peptide synthesizer. Either t-Boc or Fmoc chemistry was used to implement coupling of suitably protected amino acids to the resin or growing peptide chain thereon. The resin wash step as used herein involved placing the resin in 5 to 7 mL of a specified solvent, followed by agitation of the mixture for about 1 minute. All steps are conducted at room temperature unless stated otherwise.

t-BOC Coupling Protocol:

1. Starting resin (having thereon 0.5 mmole of covalently attached amino acid) was transferred to a 40 mL reaction vessel.

2. The resin was washed once with dichloromethane.

3. The wash was drained, then 5 to 7 mL 25% trifluoroacetic acid (in dichloromethane) was added and the mixture was agitated for about 3 minutes.

4. The liquid was drained, then 5–7 mL of 50% trifluoroacetic acid (in dichloromethane) was added to the resin and the mixture was agitated for about 16 minutes.

5. The liquid was drained, then the resin was washed five times with dichloromethane.

6. The resin was washed twice with 5% diisopropylethylamine (in N-methylpyrrolidone).

7. The resin was washed six times with N-methylpyrrolidone.

8. 3.3 mL N-methylpyrrolidone was added to 2 mmole of the N-a-t-Boc amino acid, followed by 2 mL of 1M HOBT (in N-methylpyrrolidone). The mixture was intermittently mixed for about 3 minutes, then was transferred to 2 mL of 1M dicyclohexylcarbodiimide (in N-methylpyrrolidone). This mixture was intermittently mixed for about 25 minutes, then resulting dicyclohexylurea was filtered out by transferring the mixture containing the activated N-a-t-Boc amino acid into the reaction vessel containing the resin. The resin-containing solution was then agitated for about 60 minutes.

9. The liquid was drained, then the resin was washed five times with dichloromethane.

10. The coupling cycle (steps 2 to 8) was repeated starting at step 2 until the desired peptide was completed.

Fmoc Coupling Protocol:

1. Starting resin (having thereon 0.25 mmole of covalently attached amino acid) was transferred to a 40 mL reaction vessel.

2. The resin was washed once with N-methylpyrrolidone.

3. The liquid was drained, then 5 to 7 mL 20% piperidine (in N-methylpyrrolidine) was added and the mixture was agitated for about 6 minutes.

4. The liquid was drained, then the resin was washed five times with N-methylpyrrolidone.

5. 2.4 mL N-methylpyrrolidone was added to 1 mmole of the N-a-Fmoc amino acid, followed by 2.2 mL of 0.45M HBTU-HOBT (in dimethylformamide) and then the mixture was intermittently mixed for about 6 minutes. The mixture was transferred to the reaction vessel containing the resin. 0.34 mL of diisopropylethylamine was then added and the solution was agitated for about 30 minutes.

6. The liquid was drained, then the resin was washed five times with N-methylpyrrolidone.

7. The coupling cycle (steps 2 to 6) was repeated starting at step 2 until the desired peptide was completed.

Example 2

Preparation of alpha-N-t-butoxycarbonyl-$N^g$-nitroargininal

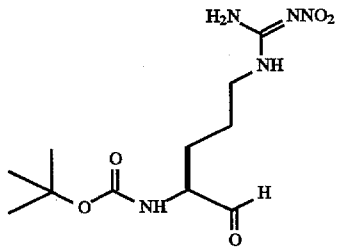

A. Procedure 1:

The following procedure for the synthesis of a-t-butoxycarbonyl-$N^g$-nitro-argininal 2 is an example of a general procedure for the preparation of Boc-amino acid aldehydes, see Patel et al., Biochim. Biophys. Acta, 748, 321–330 (1983).

In 200 mL dry THF, 12.7 g Boc-$N^g$-nitro-arginine (40 mmoles) and 7.0 g carbonyldiimidazole (CDI; 43 mmoles) were added at room temperature and allowed to stir for 30 minutes. The reaction mixture was cooled to −78° C. and 35 mL of a solution of LiAlH$_4$ (1M in THF) were added dropwise over thirty minutes. The reaction was allowed to stir for an additional hour at −78° C. Next, 18 mL of acetone were added and this mixture was quickly added to 400 mL of 1N HCl. The mixture was extracted twice with 100 mL of ethyl acetate. The ethyl acetate washes were combined and then washed two times each with 100 mL water, 100 mL saturated NaHCO$_3$ and 100 mL saturated NaCl. The solution was dried (MgSO$_4$) and concentrated to a foam. The crude weight of the a-t-butoxycarbonyl-$N^g$-nitro-argininal was 6.36 g (21 mmole; yield 52%).

B. Procedure 2:

Alternatively, 2 was synthesized by a modification of the procedure of Fehrentz, J. A. and Castro, B., Synthesis, 676 (1983).

11.4 mL of N-methyl piperidine was slowly added to a stirred suspension of 8.42 g (94 mmole) of N,O-dimethylhydroxylamine in 75 mL dichloromethane which had been cooled to about 0° C. The solution was allowed to stir for 20 minutes which gave the free hydroxylamine, then was kept cold for use in the next step.

In a separate flask, 30.0 g (94 mmole) of Boc-$N^g$-nitroarginine was dissolved by heating in about 1400 mL of tetrahydrofuran, then the mixture was cooled under nitrogen to 0° C. 11.4 mL of N-methylpiperidine and 12.14 mL (94 mmole) of isobutylchloroformate was added and the mixture stirred for 10 minutes. The free hydroxylamine prepared above was added all at once and the reaction mixture was allowed to warm to room temperature, then stirred overnight.

The resulting precipitate was filtered off, then washed with 200 mL of tetrahydrofuran. After concentrating the filtrates to about 150 mL under vacuum, 200 mL of ethyl acetate was added, followed by ice to cool the solution. The cooled ethyl acetate phase was washed with two 75 mL portions of 0.2N hydrochloric acid, two 75 mL portions of 0.5N sodium hydroxide, one portion of 75 mL of brine, then the organic phase was dried over anhydrous magnesium sulfate. Upon concentration in vacuum, 22.7 g (70% yield) of solid Boc-$N^g$-nitroarginine N-methyl-O-methylcarboxamide was recovered. Thin layer chromatographic analysis in 9:1 dichloromethane/methanol (silica gel) showed one spot.

A flask was placed under a nitrogen atmosphere and cooled to −50° C., then charged with 70 mL (70 mmole) of 1N lithium aluminum hydride (in tetrahydrofuran) and 500 mL of dry tetrahydrofuran. 50 mL of a solution containing 66 mmole of Boc-$N^g$-nitroarginine N-methyl-O-methylcarboxamide in dry tetrahydrofuran was slowly added while the temperature of the reaction mixture was maintained at −50° C. After allowing the reaction mixture to warm to 0° C. by removal of the cooling, it was recooled to −30° C., at which temperature, 100 mL (0.2 mole) of 2N potassium bisulfate was added with stirring over about a 10 to 15 minute period. The reaction mixture was then allowed to stir at room temperature for 2 hours. After filtering off the precipitate, the filtrate was concentrated to 100 mL under vacuum. The concentrate was poured into 800 mL ethyl acetate, then was successively washed with two 50 mL portions of 1N hydrochloric acid, two 50 mL portions of saturated sodium bicarbonate, one 50 mL portion of brine. The combined aqueous extracts were extracted with 3–100 mL portions of ethyl acetate. All of the ethyl acetate washes were combined, then was dried over anhydrous magnesium sulfate. The mixture was concentrated under vacuum to yield 18.5 g (95%) of the title compound.

Example 3

Preparation of N-(nitroguanidino-1-(S)-(cyanohydroxymethyl)butyl)-1-(1,1-dimethylethoxy)methanamide

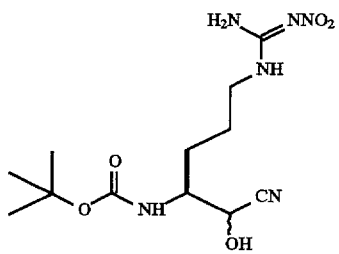

A solution of 25.2 g (83.1 mmoles) of alpha-Boc-N$^g$-nitro-argininal 2 in 680 mL tetrahydrofuran was added to a solution of 136 g (1.36 moles) of potassium bicarbonate and 27.6 g (423 mmoles) of potassium cyanide in 680 mL of water. This two phase mixture was allowed to stir vigorously for thirty minutes. The stirring was discontinued and the phases were separated. The aqueous phase was extracted three times with 500 mL ethyl acetate. The tetrahydrofuran phase was diluted with 1000 mL of ethyl acetate. The organic phases were combined and extracted successively with water and brine. This solution was dried over anhydrous magnesium sulfate and concentrated under vacuum to give 28.1 g of the above-identified product as a white foam. This material can be purified by flash chromatography (0 to 6% methanol in dichloromethane) or carried through the next steps directly. $^1$H NMR (CD$_3$OD) d 1.37 (s, 9H), 1.53 (m, 2H), 1.7 (m, 2H), 3.19 (m, 2H), 3.65 (m, 1H), 4.29 (d, J=7 Hz, 0.35H), 4.48 (d, J=4 Hz, 0.65H).

Example 4

Preparation of 6-nitroguanidino-3-(S)-amino-2-hydroxyhexanoic Acid Hydrochloride Salt

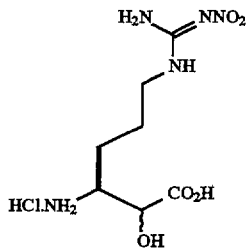

The 26.0 g (~83 mmole) crude cyanohydrin 3 was dissolved in 450 mL dioxane, and 450 mL concentrated aqueous hydrochloric acid was slowly added with stirring. This addition was accompanied by vigorous gas evolution. This solution was heated to reflux and stirred for 15 hours. After this period of time, the reaction was allowed to cool to room temperature and then concentrated under vacuum to a thick brown syrup of 6-nitroguanidino-3-(S)-amino-2-hydroxyhexanoic acid hydrochloride salt. This was used directly in the next step.

Example 5

6-Nitroguanidino-3-(S)-amino-2-hydroxyhexanoic Acid Methyl Ester

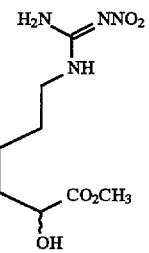

This crude acid 4 was concentrated several times from methanol under vacuum and then dissolved in 750 mL of saturated anhydrous hydrochloric acid in methanol. This suspension was refluxed for three hours, allowed to cool to room temperature and concentrated under vacuum. This gave crude 6-nitroguanidino-3-(S)-amino-2-hydroxyhexanoic acid methyl ester hydrochloride salt as a thick brown syrup. This was used directly in the next step.

Example 6

6-Nitroguanidino-3-(S)-(1,1-dimethylethoxy)methanamido-2-hydroxyhexanoic Acid Methyl Ester

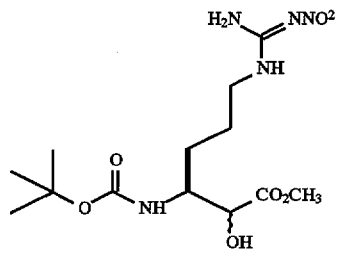

The amino ester 5 from above was dissolved in a mixture of 300 mL of saturated sodium bicarbonate and 300 mL tetrahydrofuran. This mixture was treated with di-t-butyldicarbonate (30 g, 137 mmoles) and allowed to stir vigorously for 16 hours. The resulting mixture was extracted with ethyl acetate (1000 mL). The organic layer was washed successively with water then brine, dried over anhydrous magnesium sulfate and concentrated to a small volume under vacuum. The product was purified by flash chromatography (0 to 10% methanol/dichloromethane) to give 13.5 g (49% yield) of the above-identified product as an off-white foam. $^1$H NMR (CDCl$_3$) d 1.41 and 1.45 (s, 9H), 1.7 (m, 4H), 3.2 (m, 2H); 3.82 and 3.84 (s, 3H), 4.10 (m, 1H), 4.19 (bs, 0.65H), 4.33 (bs, 0.35H), 5.02 (d, J=10 Hz; 1H), 5.17 (d, J=10 Hz, 1H).

Example 7

Preparation of 6-nitroguanidino-3-(S)-(1,1-dimethylethoxy)methanamido-2-hydroxyhexanoic Acid

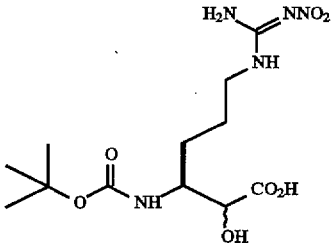

A solution of the compound 6 (5.0 g, 13.8 mmole) in 100 mL of methanol was treated with 17.mL of 1M lithium hydroxide. This solution was allowed to stir overnight and then treated with 20 mL of Dowex-50 resin X8 400 (H$^+$ form) in 50 mL of deionized water. This solution was swirled for 15 minutes then passed through a 4×4 cm. column of the same resin, the column was washed with 1:1 methanol:water and the combined filtrates were concentrated to dryness under vacuum. The residue was dissolved in 100 mL acetonitrile and concentrated to dryness, this process was repeated two more times to give 4.2 g (87 % yield) of the above-identified compound as an off-white foam. $^1$H NMR (CD$_3$OD) d 1.42 and 1.42 (s, 9H), 1.7 (m, 4H), 3.3 (m, 2H), 3.95 (m, 1H), 4.19 (bs, 0.65H), 4.33 (bs, 0.35H), 4.15 (d, J=1 Hz, 0.65H), 4.38 (d, J=4 Hz).

Example 8

Preparation of (3-dimethylaminopropyl)carbodiimide hydrochloride salt (EDAC-HCl), 2 mmole dichloroacetic acid (DCA), 2 mL of dry dichloromethane and.2 mL of dry dimethylsulfoxide; stirring the reaction mixture for 4 hours; then finally washing the resin three times with 5 to 7 mL of dry dichloromethane.

(c) Deprotection and Removal

The peptide resin and a volume of anisole numerically equal to the weight of resin were transferred to a plastic reaction vessel. After purging the vessel and associated lines with nitrogen, the reaction mixture was cooled to −20° C. and 10 mL of hydrofluoric acid (HF) was distilled into the reaction vessel. The mixture was first stirred for 30 minutes at −20° C., then for 120 minutes at 0° to 10° C. After removing the HF by evaporation, 20 mL diethyl ether was

[1] [SEQ. ID. NO. 18]
8

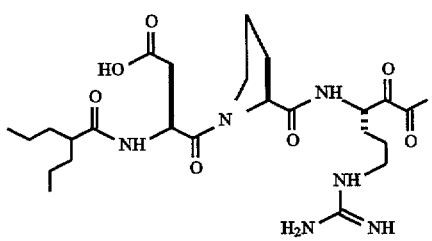

NH—(Gly)$_5$—Asn—Gly—Asp—Phe—Glu—Glu—Ile—Pro—Glu—Tyr—Leu—OH

This compound was prepared using the tBOC Coupling Protocol as described in Example 1, followed by oxidation, deprotection and removal of the peptide from the resin, and HPLC purification.

(a) Coupling

Boc-L-leucine-Pam Resin, the starting resin, was purchased from Advanced ChemTech (Louisville, Ky.).

N-Boc-O-(2-bromobenzyloxycarbonyl)-L-tyrosine was first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and N-Boc-L-aspartic acid-b-cyclohexyl ester. In the final coupling cycle, 2 mmole of 2-propylpentoic acid was coupled in the same manner as described for the N-Boc amino acids.

(b) Oxidation

The peptide resin was transferred to another reaction vessel and washed twice with 5 to 7 mL of dry dichloromethane.

The a-hydroxy group of the resin-bound peptide was oxidized to a keto group by treating the resin to two oxidation cycles. Each oxidation cycle was performed by suspending the resin in a mixture of 5 mL of dry dichloromethane and 5 mL of dry dimethylsulfoxide; deoxygenating the mixture with nitrogen; adding 5 mmole 1-ethyl-3- added, then decanted. The resin was then transferred to an extraction funnel, washed with 3–20 mL portions of diethyl ether, then extracted with 3–50 mL portions of 0.1M ammonium bicarbonate. The extracts were combined and then extracted with 2–25 mL portions of diethyl ether, saving the aqueous phase each time. The aqueous phase was frozen and lyophilized to yield crude product. The resin was further extracted with 50 mL of 40% acetonitrile+0.1% trifluoroacetic acid (in water), the extract stripped of acetonitrile in vacuo, frozen, and then lyophilized to yield a more crude product.

(d) HPLC Purification

The crude product was dissolved in 20% acetonitrile (in water containing 0.1% trifluoroacetic acid) and was put onto a 2.5×300 mm C18 reverse phase column (VYDAC) and the effluent was monitored at 210 nm. A 20 minute gradient of 20% to 35% acetonitrile (in water containing 0.1% trifluoroacetic acid) was run at a flowrate of 1 mL/minute. Title compound was collected at a retention time of 19.0 minutes. Fast atom bombardment mass spectrometry gave observed molecular weight of 2133.8 a.m.u.; calculated molecular weight was 2133.3 a.m.u.

Example 9

Preparation of

[45] [SEQ. ID. NO. 87]
9

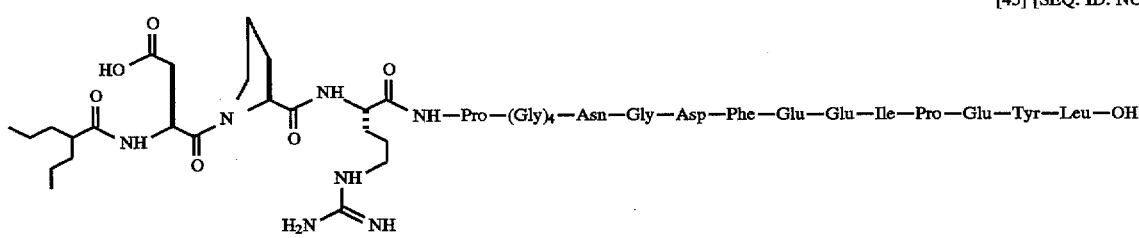

This compound was prepared using the Fmoc Coupling Protocol as described in Example 1, followed by deprotection and removal from the resin, and HPLC purification.

(a) Preparation on Resin

Fmoc-L-leucine-Pam Resin, the starting resin, was purchased from Advanced ChemTech (Louisville, Ky.).

N-Fmoc-O-t-butyl-L-tyrosine was first coupled to the resin, followed by N-Fmoc-L-glutamic acid-g-t-butyl ester, N-Fmoc-L-proline, N-Fmoc-L-isoleucine, N-Fmoc-L-glutamic acid-g-t-butyl ester, N-Fmoc-L-glutamic acid-g-t-butyl ester, N-Fmoc-L-phenylalanine, N-Fmoc-L-aspartic acid-b-t-butyl ester, N-Fmoc-glycine, N-a-Fmoc-N-b-(trityl)-L-asparagine, N-Fmoc-glycine, N-Fmoc-glycine, N-Fmoc-glycine, N-Fmoc-glycine, N-Fmoc-L-proline, N-a-Fmoc-N$^g$-(2,2,5,7,8-pentamethylchroman-6-sulfonyl)-L-arginine, N-Fmoc-L-proline, and N-Boc-L-aspartic acid-b-t-butyl ester. In the final coupling cycle, 2 mmole of 2-propylpentoic acid was coupled in the same manner as described for the N-Fmoc amino acids.

(b) Deprotection and Removal from Resin

Ten mL of trifluoroacetic acid, 0.75 g of phenol, 0.25 mL of ethanedithiol (EDT), 0.5 mL of water, and 0.5 mL of thioanisole were combined to give cleavage mixture. The cleavage mixture was cooled on an ice bath, transferred to 0.30 g of the peptide resin. After stirring the reaction mixture for 2.5 hours at room temperature, the resin was filtered off, washed with 3–15 mL portions of trifluoroacetic acid, and 3–15 mL portions of dichloromethane. The combined filtrates were then concentrated in vacuo to an oil and titurated with 5 mL of diethyl ether to yield a participate. The participate was filtered off, then redissolved in 50 mL of water. The solution was extracted with 3–25 mL portions diethyl ether, then frozen lyophilized to yield crude product.

(c) HPLC Purification

The crude product was dissolved in 15% acetonitrile (in water containing 0.1% trifluoroacetic acid) and was put onto a 2.5×300 mm C18 reverse phase column (VYDAC) and the effluent was monitored at .210 nm. A 20 minute gradient of 15% to 40% acetonitrile (in water containing 0.1% trifluoroacetic acid) was run at a flowrate of 1 mL/minute. Title compound was collected at a retention time of 18.5 minutes. Fast atom bombardment mass spectrometry gave observed molecular weight of 2144.4 a.m.u.; calculated molecular weight was 2145.3 a.m.u.

Example 10

Preparation of

N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and N-Boc-L-aspartic acid-b-cyclohexyl ester. In the final coupling cycle, 2 mmole of 2-propylpentoic acid was coupled in the same manner as described for the N-Boc amino acids.

(b) Oxidation.

The peptide resin was transferred to another reaction vessel and washed twice with 5 to 7 mL of dry dichloromethane.

The a-hydroxy group of the resin-bound peptide was oxidized to a keto group by treating the resin to three oxidation cycles. Each oxidation cycle was performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 4 hours; then finally washing the resin three times with 5 to 7 mL of dry dichloromethane. In the last two oxidation cycles, the oxidation time was 3 hours for each cycle.

(c) Deprotection and Removal.

The peptide resin and a volume of anisole numerically equal to the weight of resin were transferred to a plastic reaction vessel. After purging the vessel and associated lines with nitrogen, the reaction mixture was cooled to −20° C. and 10 mL of hydrofluoric acid (HF) was distilled into the reaction vessel. The mixture was first stirred for 30 minutes at −20° C., then for 120 minutes at 0° to 10° C. After removing the HF by evaporation, 20 mL diethyl ether was added, then decanted. The resin was then transferred to an extraction funnel, washed with 3–20 mL portions of diethyl ether, then extracted with 3–50 mL portions of 20% acetic acid (in water). The extracts were combined and then extracted with 3–25 mL portions of diethyl ether, saving the aqueous phase each time. The aqueous phase was frozen and lyophilized to yield crude product.

(d) HPLC purification.

The crude product was dissolved in 10% acetonitrile (in water containing 0.1% trifluoroacetic acid) and was put onto

[31] [SEQ. ID. NO. 48]

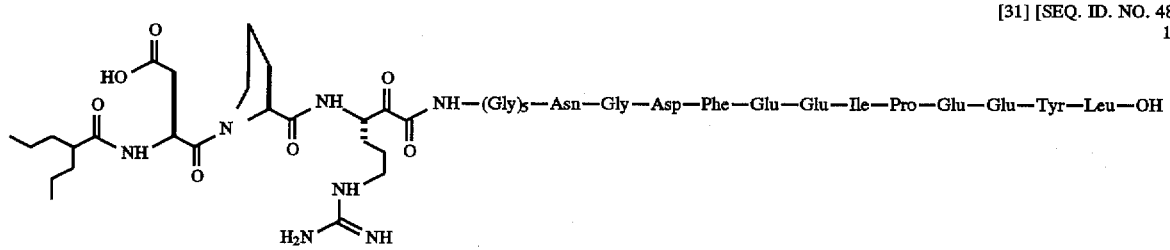

This compound was prepared using the tBOC Coupling Protocol as described in Example 1, followed by oxidation, deprotection and removal of the peptide from the resin, and HPLC purification.

(a) Coupling

Boc-L-leucine-Pam Resin, the starting resin, was purchased from Advanced Chemtech (Louisville, Ky.).

N-Boc-O-(2-bromobenzyloxycarbonyl)-L-tyrosine was first coupled to the resin, followed by N-Boc-L-glutamic acid-g-cyclohexyl ester, N-Boc-L-glutamic acid-g-cyclohexyl ester, N-Boc-L-proline, N-Boc-L-isoleucine, a 2.5×300 mm C18 reverse phase column (VYDAC) and the effluent was monitored at 210 nm. A 20 minute gradient of 10% to 35% acetonitrile (in water containing 0.1% trifluoroacetic acid) was run at a flowrate of 1 mL/minute. Title compound was collected at a retention time of 12.0 minutes. Fast atom bombardment mass spectrometry gave observed molecular weight of 2262.0 a.m.u.; calculated molecular weight was 2262.4 a.m.u.

Example 11

Preparation of

[21] [SEQ. ID. NO. 38]
11

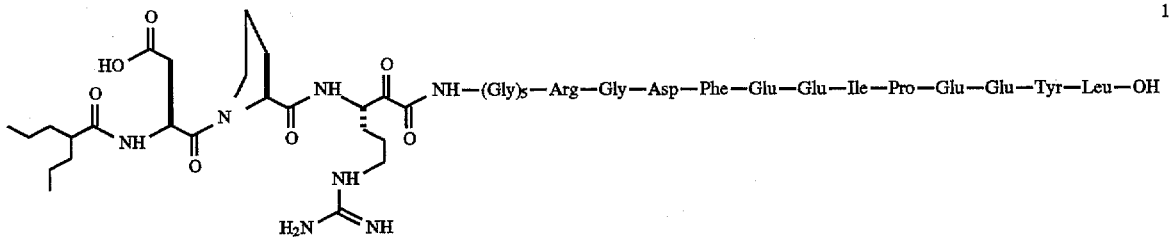

This compound was prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, was purchased from Advanced ChemTech, Louisville, Ky.).

N-Boc-O-(2-bromobenzyloxycarbonyl)-L-tyrosine was first coupled to the resin, followed by N-Boc-L-glutamic acid-g-cyclohexyl ester, N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-a-Boc-$N^g$-tosyl-L-arginine, N-Boc-glycine, N-Boc-glycine, N-Boc-glycine, N-Boc-glycine, N-Boc-glycine, 6-nitroguanidino-3-(S)-(1,1-dimethylethoxy) methanamido-2-hydroxyhexanoic acid 7, N-Boc-L-proline, and N-Boc-L-aspartic acid-b-cyclohexyl ester. In the final coupling cycle, 2 mmole of 2-propylpentoic acid was coupled in the same manner as described for the N-Boc amino acids.

(b) Oxidation.

The peptide resin was transferred to another reaction vessel and washed twice with 5 to 7 mL of dry dichloromethane.

The a-hydroxy group of the resin-bound peptide was oxidized to a keto group by treating the resin to three oxidation cycles. Each oxidation cycle was performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycle, the oxidation time was 2 hours for each cycle. After the oxidation was complete, the resin was washed three times 5 to 7 mL each with dimethylformamide, dichloromethane, methanol and diethylether.

(c) Deprotection and Removal.

The peptide resin and a volume of anisole numerically equal to the weight of resin were transferred to a plastic reaction vessel. After purging the vessel and associated lines with nitrogen, the reaction mixture was cooled to −20° C. and 15 mL of hydrofluoric acid (HF) was distilled into the reaction vessel. The mixture was first stirred for 30 minutes at −20° C., then for 120 minutes at 0° to 10° C. After removing the HF by evaporation, 20 mL diethyl ether was added, then decanted. The resin was then transferred to an extraction funnel, washed with 3–20 mL portions of diethyl ether, then extracted with 3–50 mL portions of 20% acetic acid (in water). The extracts were combined and then extracted with 3–25 mL portions of diethyl ether, saving the aqueous phase each time. The aqueous phase was frozen and lyophilized to yield crude product.

(d) HPLC purification.

The crude product was dissolved in 10% acetonitrile (in water containing 0.1% trifluoroacetic acid) and was put onto a 2.5×300 mm C18 reverse phase column (VYDAC) and the effluent was monitored at 210 nm. A 20 minute gradient of 10% to 35% acetonitrile (in water containing 0.1% trifluoroacetic acid) was run at a flowrate of 1 mL/minute. Title compound was collected at a retention time of 12.0 minutes. Fast atom bombardment mass spectrometry gave observed molecular weight of 2304.6 a.m.u.; calculated molecular weight was 2304.5 a.m.u.

Example 12

Preparation of

[7] [SEQ. ID. NO. 24]
12

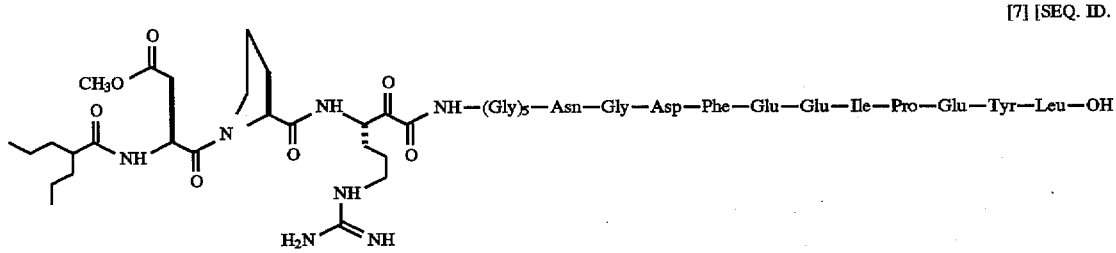

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-Boc-glycine, N-Boc-glycine, N-Boc-glycine, 6-nitroguanidino-3-(S)-(1,1-dimethylethoxy)methanamido-2- hydroxyhexanoic acid 7, N-Boc-L-proline, and N-Boc-L-aspartic acid-b-methyl ester. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycle, the oxidation time is 2 hours for each cycle.

(c) Deprotection and Removal.

The peptide resin and a volume of anisole numerically equal to the weight of resin are transferred to a plastic reaction vessel. After purging the vessel and associated lines with nitrogen, the reaction mixture is cooled to −20° C. and 10 mL of hydrofluoric acid (HF) was distilled into the reaction vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(d) HPLC purification.

The crude product is dissolved in 10% acetonitrile (in water containing 0.1% trifluoroacetic acid) and is put onto a 2.5×300 mm C18 reverse phase column (VYDAC) and the effluent is monitored at 210nm. A 20 minute gradient of 10% to 35% acetonitrile (in water containing 0.1% trifluoroacetic acid) is run at a flowrate of 1 mL/minute. The title compound was collected at a retention time of 19.2 minutes. Fast atom bombardment mass spectrometry gave an observed molecular weight of 2275.4 a.m.u.; the calculated molecular wieght was 2275.0.

Example 13

Preparation of

[37] [SEQ. ID. NO. 54]
13

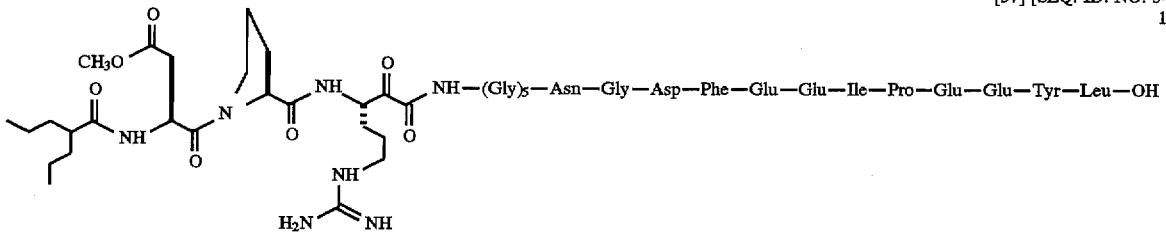

This compound was prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, was purchased from Advanced ChemTech, Louisville, Ky.).

N-Boc-O-(2-bromobenzyloxycarbonyl)-L-tyrosine was first coupled to the resin, followed by N-Boc-L-glutamic acid-g-cyclohexyl ester, N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and N-Boc-L-aspartic acid-b-methyl ester. In the final coupling cycle, 2 mmole of 2-propylpentoic acid was coupled in the same manner as described for the N-Boc amino acids.

(b) Oxidation.

The peptide resin was transferred to another reaction vessel and washed twice with 5 to 7 mL of dry dichloromethane.

The a-hydroxy group of the resin-bound peptide was oxidized to a keto group by treating the resin to three oxidation cycles. Each oxidation cycle was performed by suspending the resin in a mixture of 5 mL of dry dichloromethane and 5 mL of dry dimethylsulfoxide;. deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycles, the oxidation time was 2 hours for each cycle.

(c) Deprotection and Removal.

The peptide resin and a volume of anisole numerically equal to the weight of resin were transferred to a plastic reaction vessel. After purging the vessel and associated lines with nitrogen, the reaction mixture was cooled to −20° C. and 10 mL of hydrofluoric acid (HF) was distilled into the reaction vessel. The mixture was first stirred for 30 minutes at −20° C., then for 90 minutes at 0° to 10° C. After removing the HF by evaporation, 20 mL diethyl ether was added, then was decanted. The resin was then transferred to an extraction funnel, washed with 3–20 mL portions of diethyl ether, then extracted with 3–50 mL portions of 20% acetic acid (in water). The extracts were combined and then extracted with 3–25 mL portions of diethyl ether, saving the aqueous phase each time. The aqueous phase was frozen and lyophilized to yield crude product.

(d) HPLC purification.

The crude product was dissolved in 10% acetonitrile (in water containing 0.1% trifluoroacetic acid) and is put onto a 2.5×300 mm C18 reverse phase column (VYDAC) and the effluent was monitored at 210 nm. A 20 minute gradient of 10% to 35% acetonitrile (in water containing 0.1% trifluoroacetic acid) is run at a flowrate of 1 mL/minute.

The title compound was collected at a retention time of 19.2 minutes. Fast atom bombardment mass spectrometry gave an observed molecular weight of 2275.4 a.m.u.; the calculated molecular weight was 2275.0.

time is 2 hours for each cycle. After the oxidation was complete, the resin was washed three times 5 to 7 mL each with dimethylformamide, dichloromethane, methanol and diethylether.

(c) Deprotection and Removal.

The peptide resin and a volume of anisole numerically equal to the weight of resin are transferred to a plastic reaction vessel. After purging the vessel and associated lines with nitrogen, the reaction mixture is cooled to –20° C. and 15 mL of hydrofluoric acid (HF) is distilled into the reaction vessel. The mixture is first stirred for 30 minutes at –20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(d) HPLC purification.

Example 14

Preparation of

[27] [SEQ. ID. NO. 44]

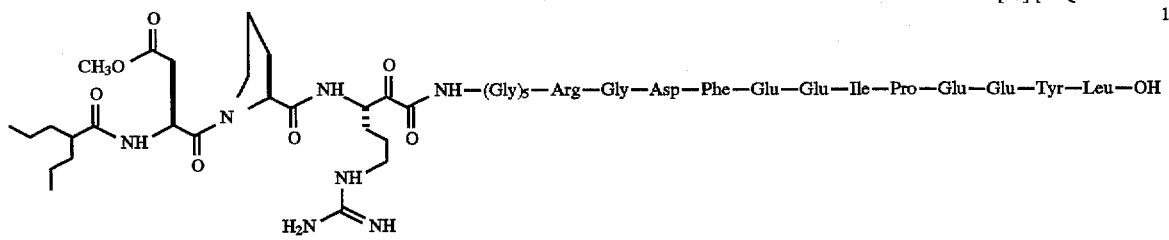

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-a-Boc-N$^g$-tosyl-L-arginine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and N-Boc-L-aspartic acid-b-methyl ester. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycle, the oxidation The crude product is dissolved in 10% acetonitrile (in water containing 0.1% trifluoroacetic acid) and is put onto a 2.5×300 mm C18 reverse phase column (VYDAC) and the effluent is monitored at 210nm. A 20 minute gradient of 10% to 35% acetonitrile (in water containing 0.1% trifluoroacetic acid) is run at a flowrate of 1 mL/minute.

Example 15

Preparation of 3-cyano-2-(1,1-dimethylethoxy) methanamido propionic acid

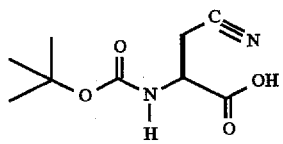

20.0 g (86 mmol, 1 equiv.) of Boc-L-asparagine (from Bachem or Sigma) was dissolved in 120 ml of dry pyridine and 20.0 g (97 mmol, 1.3 equiv.) of dicyclohexylcarbodiimide dissolved in 60 ml of dry pyridine was added dropwise over a period of 30 minutes. The reaction was stirred for 3 hours at 23° C. and filtered through a 2 µm nylon filter. The filtrate was concentrated in vacuo on a rotovap and 100 ml of water was added. The pH was adjusted to 10 with 40% sodium hydroxide (aq.) and the solution filtered through a 2 µm nylon filter once again. The filtrate was passed through a 120 ml bed of Dowex 50×8–400 ion exchange resin and the resin washed with four column volumes of 1:1 methanol:water. The filtrate was concentrated in vacuo to yield 17.5g (95% yield) of product as a white solid. $^1$H-NMR (CD$_3$OD): 4.40 p.p.m (m, 1H); 2.95 p.p.m. (m, 2H); 1.40 p.p.m. (s, 9H).

Example 16

Preparation of 3-tetrazolyl-2-(1,1-dimethylethoxy) methanamido propionic acid

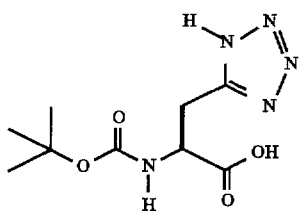

16

17.5 g (82 mmol, 1 equiv.) of 3-cyano-2-(1,1-dimethylethoxy) methanamido-propionic acid 15 was dissolved in 125 mL of tetrahydrofuran and 40.5 g (129 mmol, 1.5 equiv.) was added. The reaction mixture was brought to reflux and held there for 3 days. The reaction mixture was cooled and the volatiles removed in vacuo on the rotovap. The residue was dissolved in 300 mL of 0.5M sodium hydroxide and this aqueous solution was washed with ethyl acetate (4×100 mL). The aqueous layer was passed through a 125 mL bed of Dowex 50×8–400 ion exchange resin and the resin washed with four column volumes of 1:1 methanol:water. The volatiles were removed in vacuo on the rotovap to yield 17.9 g of the product as a white solid (85% yield). $^1$H-NMR (CD$_3$OD): 4.55 p.p.m (m, 1H); 3.40 p.p.m. (m, 2H); 1.40 p.p.m. (s, 9H). This material is suitable for use in solid-phase peptide synthesis.

Example 17

Preparation of 3-(N-2-methyl)tetrazolyl-2-(1,1-dimethylethoxy)methanamidopropionic acid, methyl ester and 3-(N-3-methyl)tetrazolyl-2-(1,1-dimethylethoxy)methan-amidopropionic acid, methyl ester

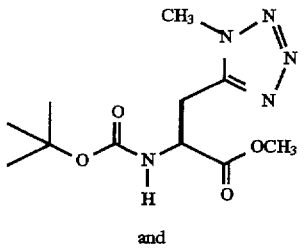

17 and

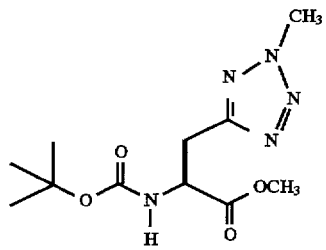

1.5 g (5.8 mmol, 1.0 equiv.) of 3-tetrazolyl-2-(1,1-dimethylethoxy)methan-amidopropionic acid 16 was dissolved in 13 mL of dry dimethylformamide and 3.9 g (12.0 mmol, 2.1 equiv.) of cesium carbonate was added. This was followed by the addition of 930 µL (14.5 mmol, 2.5 equiv.) of methyl iodide via syringe. The reaction mixture was stirred at 23° C. for 3 hours and poured into 50 mL of 0.5M hydrochloric acid. The resulting mixture was extracted with ethyl acetate (3×50 mL). The combined organics were washed with 50 mL 0.5M hydrochloric acid, 50 mL saturated sodium bicarbonate, and 50 mL brine. After drying over sodium sulfate, the organics were decanted and the volatiles removed in vacuo on the rotary evaporator to yield a mixture of the title compounds as a yellow oil. The isomers were separated by chromatography on silica gel (50% ethyl acetate/hexane) with one isomer eluting first (Rf=0.3 vs. Rf=0.15 of the other isomer on silica gel developing in 50% ethyl acetate/hexane). Fractions containing pure product were combined and the volatiles removed on the rotovap to yield 0.60 g of pure product for each of the title compounds. $^1$H-NMR (CDCl$_3$): The second-eluting isomer gave 5.8 p.p.m (d, 1H); 4.75 p.p.m (m, 1H); 4.05 p.p.m (s, 3H); 3.75 p.p.m. (s, 3H); 3.4 p.p.m (m, 2H); 1.5 p.p.m. (s, 9H). The first-eluting isomer gave: 5.75 p.p.m (d, 1H); 4.75 p.p.m (m, 1H); 4.30 p.p.m (s, 3H); 3.75 p.p.m. (s, 3H); 3.65 p.p.m (m, 2H); 1.7 p.p.m. (s, 9H).

Example 18

Preparation of 3-(N-2-methyl)tetrazolyl-2-(1,1-dimethylethoxy) methanamidopropionic acid or 3-(N-3-methyl)tetrazolyl-2(1,1-dimethylethoxy) methanamidopropionic

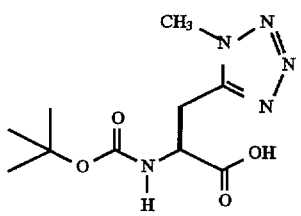

18 or

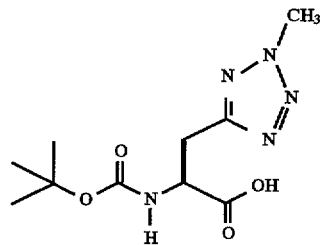

0.5 g (1.75 mmol, 1.0 equiv.) of 3-(N-2-methyl)tetrazolyl-2-(1,1-dimethylethoxy)methanamidopropionic acid methyl ester (or 3-(N-3-methyl)tetrazolyl-2-(1,1-dimethylethoxy) methanamidopropionic acid methyl ester) 17 is dissolved in 12 mL of methanol and 2.3 mL (1.3 equiv.) of 1.0M lithium hydroxide (aq.) is added. The reaction is stirred for 2 hours at 23° C. when starting material can no longer be seen by TLC analysis (1:1 ethyl acetate/hexane). The reaction mixture is passed through a 10 mL bed of Dowex 50×8–400 ion exchange resin and the resin is washed with four column volumes of 1:1 methanol:water. The solvents are removed in vacuo to yield the title product.

Example 19

Preparation of

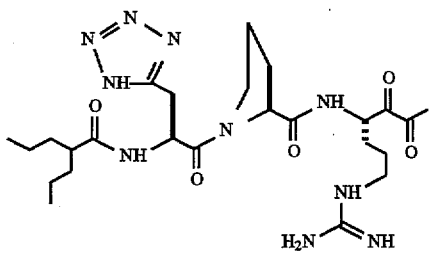

NH—(Gly)₅—Asn—Gly—Asp—Phe—Glu—Glu—Ile—Pro—Glu—Tyr—Leu—OH

[8] [SEQ. ID. NO. 25]
19

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and 3-tetrazolyl-2-(1,1-dimethylethoxy)methanamido propionic acid 16. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to two oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 4 hours; then finally washing the resin three times with 5 to 7 mL of dry dichloromethane.

(c) Deprotection and Removal.

The peptide resin and a volume of anisole numerically equal to the weight of resin are transferred to a plastic reaction vessel. After purging the vessel and associated lines with nitrogen, the reaction mixture is cooled to −20° C. and 10 mL of hydrofluoric acid (HF) is distilled into the reaction vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(d) HPLC purification.

The crude product is dissolved in 10% acetonitrile (in water containing 0.1% trifluoroacetic acid) and is put onto a 2.5×300 mm C18 reverse phase column (VYDAC) and the effluent is monitored at 210 nm. A 20 minute gradient of 10% to 35% acetonitrile (in water containing 0.1% trifluoroacetic acid) is run at a flowrate of 1 mL/minute.

Example 20

Preparation of

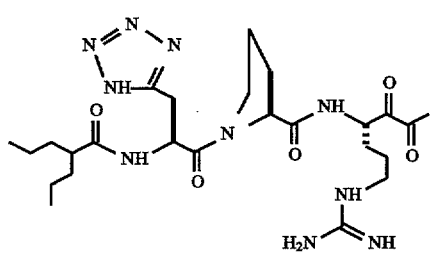

NH—(Gly)₅—Arg—Gly—Asp—Phe—Glu—Glu—Ile—Pro—Glu—Glu—Tyr—Leu—OH

[28] [SEQ. ID. NO. 45]
20

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-a-Boc-Nᵍ-tosyl-L-arginine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and 3-tetrazolyl-2-(1,1-dimethylethoxy)methanamido propionic acid 16. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycle, the oxidation time is 2 hours for each cycle. After the oxidation was complete, the resin was washed three times 5 to 7 mL each with dimethylformamide, dichloromethane, methanol and diethylether.

(c) Deprotection and Removal.

The peptide resin and a volume of anisole numerically equal to the weight of resin are transferred to a plastic reaction vessel. After purging the vessel and associated lines with nitrogen, the reaction mixture is cooled to −20° C. and 15 mL of hydrofluoric acid (HF) is distilled into the reaction vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(d) HPLC purification.

The crude product is dissolved in 10% acetonitrile (in water containing 0.1% trifluoroacetic acid) and is put onto a 2.5×300 mm C18 reverse phase column (VYDAC) and the effluent is monitored at 210 nm. A 20 minute gradient of 10% to 35% acetonitrile (in water containing 0.1% trifluoroacetic acid) is run at a flowrate of 1 mL/minute.

Example 21

Preparation of

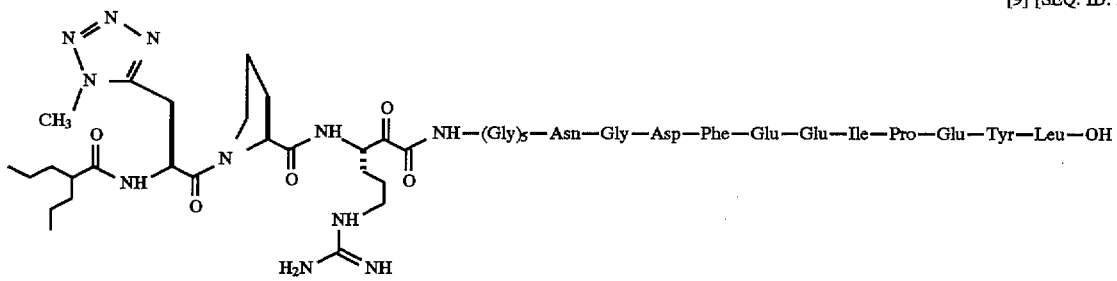

[9] [SEQ. ID. NO. 26]
21

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-Boc-glycine, N-Boc-glycine, N-Boc-glycine, 6-nitroguanidino-3-(S)-(1,1-dimethylethoxy)methanamido-2- hydroxyhexanoic acid 7, N-Boc-L-proline, and 3-(N-2-methyl) tetrazolyl-2-(1,1-dimethylethoxy) methanamidopropionic acid 18. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to two oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 4 hours; then finally washing the resin three times with 5 to 7 mL of dry dichloromethane.

(c) Deprotection and Removal.

The peptide resin and a volume of anisole numerically equal to the weight of resin are transferred to a plastic reaction vessel. After purging the vessel and associated lines with nitrogen, the reaction mixture is cooled to −20° C. and 10 mL of hydrofluoric acid (HF) is distilled into the reaction vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(d) HPLC purification.

The crude product is dissolved in 10% acetonitrile (in water containing 0.1% trifluoroacetic acid) and was put onto a 2.5×300 mm C18 reverse phase column (VYDAC) and the effluent was monitored at 210nm. A 20 minute gradient of 10% to 35% acetonitrile (in water containing 0.1% trifluoroacetic acid) was run at a flowrate of 1 mL/minute.

Example 22

Preparation of 6-nitroguanidino-3-(S)-(1,1-dimethylethoxy) methanamido-2-hydroxyhexanoic acid 7, N-Boc-L-proline, and 3-(N-2-methyl) tetrazolyl-2-(1,1-dimethylethoxy) methanamidopropionic acid 18. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycle, the oxidation time is 2 hours for each cycle. After the oxidation was complete, the resin was washed three times 5 to 7 mL each with dimethylformamide, dichloromethane, methanol and diethylether.

(c) Deprotection and Removal.

The peptide resin and a volume of anisole numerically equal to the weight of resin are transferred to a plastic reaction vessel. After purging the vessel and associated lines with nitrogen, the reaction mixture is cooled to −20° C. and 15 mL of hydrofluoric acid (HF) is distilled into the reaction

[29] [SEQ. ID. NO. 46]
22

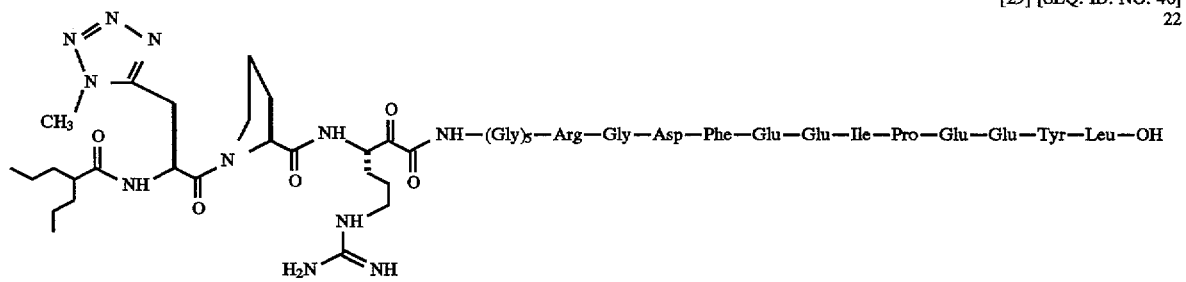

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc -glycine, N-a-Boc-N$^g$-tosyl-L-arginine, N-Boc-glycine, N-Boc-glycine, N-Boc-glycine, N-Boc-glycine, N-Boc-glycine, vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(d) HPLC purification.

The crude product is dissolved in 10% acetonitrile (in water containing 0.1% trifluoroacetic acid) and is put onto a 2.5×300 mm C18 reverse phase column (VYDAC) and the effluent is monitored at 210 nm. A 20 minute gradient of 10% to 35% acetonitrile (in water containing 0.1% trifluoroacetic acid) is run at a flowrate of 1 mL/minute.

Example 33

Preparation of

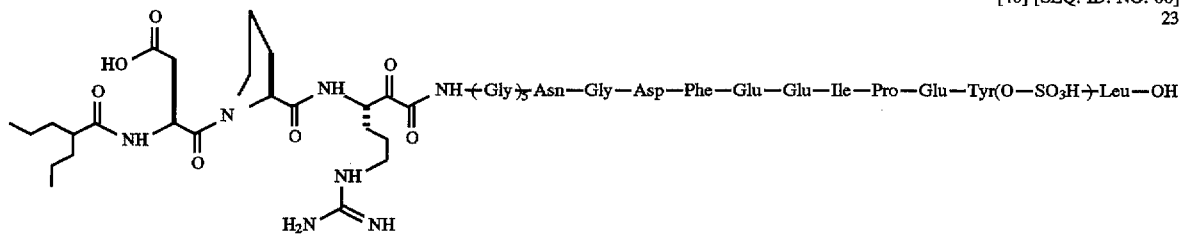

The compound of Example 8 is sulfated at its tyrosine residue using the procedure of Nakahara et al., Anal. Biochem., 154: 194–199 (1986).

1.5 mg ($7 \times 10^{-7}$ mole) of the compound of Example 8 is dissolved in 0.050 mL of dimethylformamide and then was dried under a flow of nitrogen. The compound is redissolved in 0.040 mL of dimethylformamide containing $2 \times 10^{-5}$ mole of sulfuric acid, 0.012 mg ($0.6 \times 10^{-7}$ mole) of N,N'-dicyclohexylcarbodiimide in 0.010 mL of dimethylformamide is added, and the reaction mixture is mixed by swirling. The reaction is allowed sit for about 5 to 10 minutes, then 0.75 mL of deionized water is added. Insoluble reaction products are removed by centrifugation in a microfuge apparatus. The solvent is removed under a flow of nitrogen.

The crude product is dissolved in 10% acetonitrile (in water containing 0.1% trifluoroacetic acid) and is put onto a 2.5×300 mm C18 reverse phase column (VYDAC) and the effluent is monitored at 210 nm. A 20 minute gradient of 0% to 35% acetonitrile (in water containing 0.1% trifluoroacetic acid) is run at a flowrate of 1 mL/minute. Fractions are collected, dried in a speed-vac apparatus and redissoved in deionized water. The column fractions are assayed as disclosed in Example A and selected for their ability to inhibit a-thrombin.

Example 24

Preparation of I-123 labelled

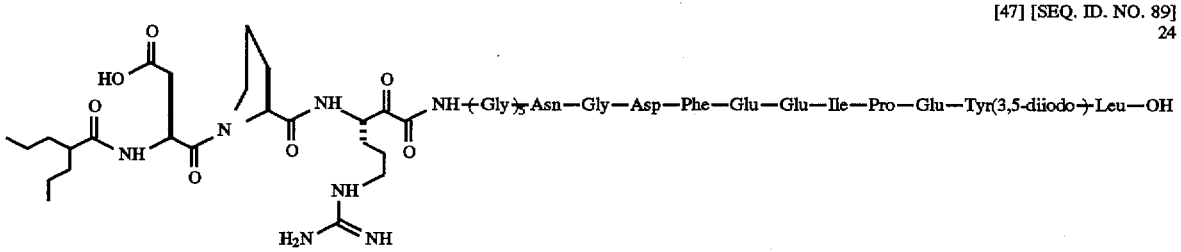

The compound of Example 8 is covalently at its tyrosine with iodine-123.

The compound of Example 8 is reacted with I-123 Bolton Hunter Reagent (New England Nuclear, Boston, Mass.) in 0.1M sodium borate buffer, pH 9.0 so that the title compound would have a specific activity greater than 5 mCi/mg. After the labelling, the I-123 labelled title compound is isolated by desalting the reaction mixture by passage through a Biogel P2 column, which is equilibrated with 0.01M sodium phosphate, pH 7.2, containing 0.15 M sodium chloride.

[46] [SEQ. ID. NO. 88]
23

Example 25

Preparation of Hirulog-1

(D-Phe)-Pro-Arg-Pro-(Gly)$_4$-Asn-Gly-Asp-Phe-Glu-Glu-Ile-Pro-Glu-Glu-Tyr-Leu-OH [48]

25

This compound was prepared using the Fmoc Coupling Protocol as described in Example 1, followed by deprotection and removal from the resin, and HPLC purification.

(a) Preparation on resin.

Fmoc-L-leucine-Pam Resin, the starting resin, was purchased from Advanced ChemTech, Louisville, Ky.).

N-Fmoc-O-t-butyl-L-tyrosine was first coupled to the resin, followed by N-Fmoc-L-glutamic acid-g-t-butyl ester, N-Fmoc-L-proline, N-Fmoc-L-isoleucine, N-Fmoc-L-glutamic acid-g-t-butyl ester, N-Fmoc-L-glutamic acid-g-t-butyl ester, N-Fmoc-L-phenylalanine, N-Fmoc-L-aspartic acid-b- t-butyl ester, N-Fmoc-glycine, N-a-Fmoc-N-b-(trityl)-L-asparagine, N-Fmoc-glycine, N-Fmoc-glycine, N-Fmoc-glycine, N-Fmoc-glycine, N-Fmoc-L-proline, N-a-Fmoc-N$^g$-(2,2,5,7,8-pentamethylchroman-6-sulfonyl)-L-arginine, N-Fmoc-L-proline, and N-Fmoc -D-phenylalanine.

(b) Deprotection and removal from resin.

Ten mL of trifluoroacetic acid, 0.75 g of phenol, 0.25 mL of ethanedithiol (EDT), 0.5 mL of water, and 0.5 mL of thioanisole were combined to give cleavage mixture. The cleavage mixture was cooled on an ice bath, transferred to 0.30 g of the peptide resin. After stirring the reaction mixture for 2.5 hours at room temperature, the resin was filtered off, washed with 3–15 mL portions of trifluoroacetic acid, and 3–15 mL portions of dichloromethane. The combined filtrates were then concentrated in vacuo to an oil and then titurated with 5 mL of diethyl ether to yield a participate. The participate was filtered off, then redissolved in 50 mL of 0.1M ammonium bicarbonate. The solution was extracted with 3–25 mL portions diethyl ether, then frozen lyophilized to yield crude product.

[47] [SEQ. ID. NO. 89]
24

(c) HPLC Purification.

The crude product was dissolved in 15% acetonitrile (in water containing 0.1% trifluoroacetic acid) and was put onto a 2.5×300 mm C18 reverse phase column (VYDAC) and the effluent was monitored at 210 nm. A 20 minute gradient of 15% to 30% acetonitrile (in water containing 0.1% trifluoroacetic acid) was run at a flowrate of 1 mL/minute. Title compound was collected at a retention time of 17.0 minutes. Fast atom bombardment mass spectrometry gave observed molecular weight of 2178.6 a.m.u.; calculated molecular weight was 2179.0 a.m.u.

Example 26

Preparation of

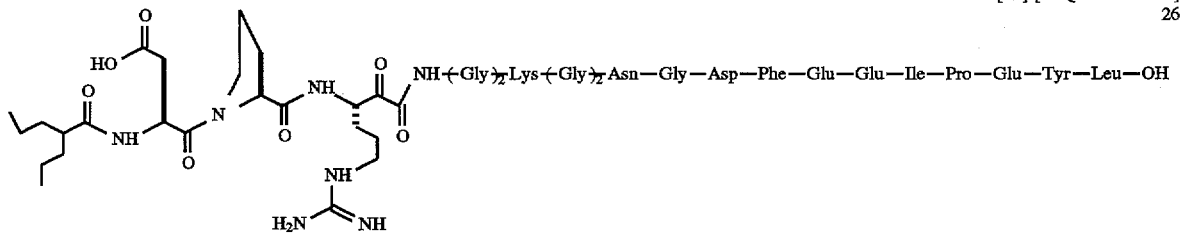

[49] [SEQ. ID. NO. 90]
26

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxcarbonyl)-L-tyrosine is first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-a-Boc-N-e-Cbz-lysine, N-Boc-glycine, N-Boc-glycine, 6-nitroguanidino-3-(S)-(1,1-dimethylethoxy)methanamido-2-hydroxyhexanoic acid 7, N-Boc-L-proline, and N-Boc-L-aspartic acid-b-cyclohexyl ester. In the final coupling cycle, 2 mole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to two oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 4 hours; then finally washing the resin three times with 5 to 7 mL of dry dichloromethane.

(c) Deprotection and Removal.

The peptide resin and a volume of anisole numerically equal to the weight of resin are transferred to a plastic reaction vessel. After purging the vessel and associated lines with nitrogen, the reaction mixture is cooled to −20° C. and 10 mL of hydrofluoric acid (HF) was distilled into the reaction vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 0.1M ammonium bicarbonate. The extracts are combined and then extracted with 2–25 mL portions of diethyl ether, saving the aqueous phase each time. The aqueous phase is frozen and lyophilized to yield crude product. The resin is further extracted with 50 mL of 40% acetonitrile +0.1% trifluoroacetic acid (in water), the extract stripped of acetonitrile in vacuo, frozen, and then lyophilized to yield a more crude product.

(d) HPLC purification.

The crude product is dissolved in 20% acetonitrile (in water containing 0.1% trifluoroacetic acid) and is put onto a 2.5×300 mm C18 reverse phase column (VYDAC) and the effluent is monitored at 210 nm. A 20 minute gradient of 20% to 35% acetonitrile (in water containing 0.1% trifluoroacetic acid) is run at a flowrate of 1 mL/minute.

Example 27

Crosslinking of Peptide from Example 8 to Metallothionein

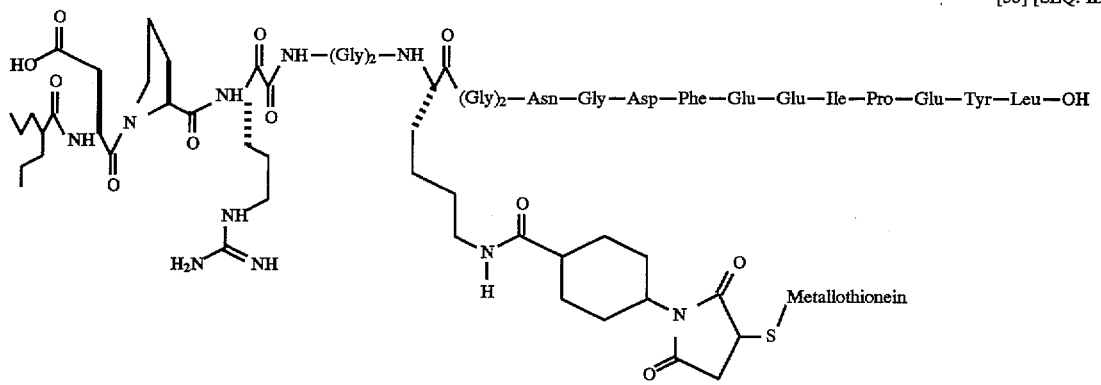

[50] [SEQ. ID. NO. 91]
27

The following procedure used corresponds to that outlined by Brown, et. al., Analytical Biochemistry, 172: 22 (1988). Succinimidyl 4-(N-maleimidomethyl)cyclohexane-1-carboxylate (SMCC, purchased from Pierce Chemical Co. and recrystallized from acetone) is first dissolved in methylsulfoxide (DMSO, 1 mg/ml) and diluted to 50% with water immediately prior to use. The peptide prepared in Example 26 is placed in buffer (1 mg/ml, 10 mM sodium phosphate, 150 mM sodium chloride, pH=7.5) and incubated with a freshly prepared SMCC solution at 4° C. for 16 hours such that the molar ratio of SMCC to peptide is 5:1. The unreacted SMCC is removed on a Sephadex G-15 column and the fractions containing peptide are pooled and lyophilized. A solution of 10 molar equivalents of metallothionein [$Zn_7MT$, pure apo-MT is isolated from rabbit liver as described in Pande, et. al., Biochemistry, 24: 6717 (1985) and converted to the fully metallated $Zn_7MT$ form as described by Morelock & Tolman in Metallothionein (Kagi & Nordberg, eds.), pp. 247–253. Birkhauser, Basel] in 50 mM Tris-HCl, pH=9.0 was added to an equal volume of SMCC-activated peptide at a concentration of 1.5 mg/ml. The mixture was incubated at 4° C. for 16 hours. and the peptide-metallothionein conjugate purified on a Sephadex G-50 column.

Example 28

Preparation of 1-(p-nitrobenzyl)diethylene triaminepentaacetic acid, penta-t-butyl ester

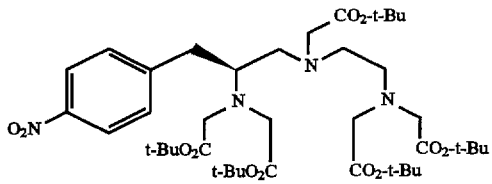

1-(p-nitrobenzyl)diethylenetriamine trihydrochloride is prepared as described by Brechbiel, et. al., Inorg. Chem., 25: 2772 (1986). This material is suspended in dry THF (0.3M) along with 20 equivalents of potassium carbonate. 10 equivalents of t-butyl bromoacetate (available from Aldrich Chemical Co.) was added and the reaction mixture is sonicated under nitrogen at 60° C. for 24 hours or until the reaction is complete as judged by TLC. The salts are filtered off and the volatiles removed in vacuo. Pure product is obtained by chromatography on silica (ethyl acetate/hexane).

Example 29

Preparation of 1-(p-aminobenzyl)diethylene triaminepentaacetic acid, penta-t-butyl ester

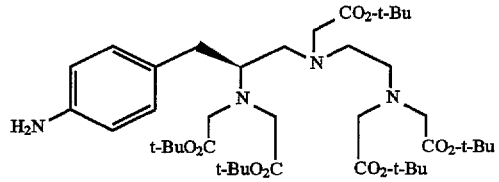

1-(p-nitrobenzyl) diethylenetriaminepentaacetic acid, penta-t-butyl ester is taken up in ethanol (0.1M) and placed in an atmospheric hydrogenation apparatus. The solution is purged with nitrogen and 10% Pd/C is added. The reaction mixture is then purged with hydrogen and stirred rapidly at ambient temperature until a hydrogen atmosphere until starting material is consumed by TLC analysis. The catalyst is filtered off and the volatiles removed in vacuo to yield crude product. This material is used as is for the subsequent reaction. An analytical sample can be obtained by chromatography on silica (ethyl acetate/hexane).

Example 30

Preparation of 1-(p-isothiocyanatobenzyl)diethylene triaminepentaacetic acid, penta-t-butyl ester

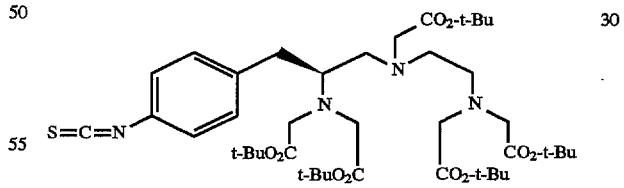

1-(p-aminobenzyl)diethylenetriaminepentaacetic acid, penta-t-butyl ester is taken up in chloroform (0.2M) and placed in a round bottom flask equipped with magnetic stirring. 3 equivalents of diisopropylethylamine is added followed by the addition of 1.2 equivalents of a 0.1M solution of thiophosgene in chloroform. Stirring is continued until the starting material is consumed by TLC analysis. The volatiles are removed in vacuo and pure product obtained by chromatography on silica (ethyl acetate/hexane).

Example 31

Preparation of thrombin-binding peptide which is attached to a diethylenetriaminepentaacetic acid chelator during solid-phase synthesis

[51] [SEQ. ID. NO. 92]
31

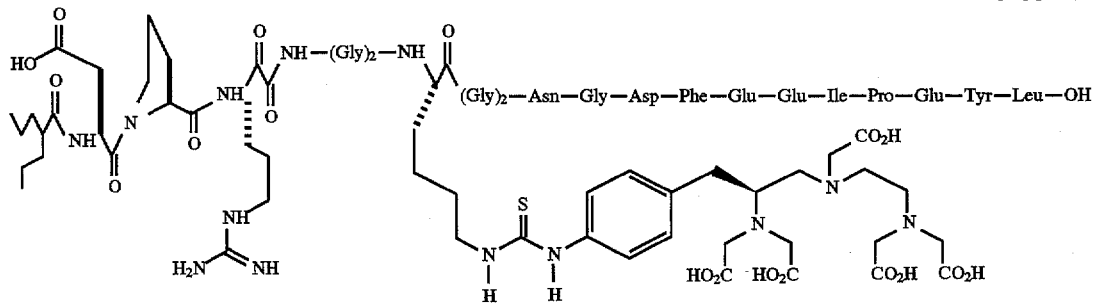

This compound is prepared using the tBOC Coupling Protocol as described in Example 1. The single lysine residue incorporated in the peptide is protected at the epsilon nitrogen as a 9-fluorenylmethyloxycarbamate and is selectively deprotected followed by reaction with 1-(p-isothiocyanatobenzyl) ethylenediaminetetraacetic acid, penta-t-butyl ester. This is followed by oxidation, deprotection of the other protecting groups, removal of the peptide from the resin, and HPLC purification.

(a) Coupling.

Boc-L-leucine-Pam Resin, the starting resin, is purchased from Advanced ChemTech; Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-Boc-asparagine, N-Boc-glycine, N-Boc-glycine, N-a-Boc-N-e-fmoc-lysine, N-Boc-glycine, N-Boc-glycine, 6-nitroguanidino-3-(S)-(1,1-dimethylethoxy) methanamido-2-hydroxyhexanoic acid 7, N-Boc-L-proline, and N-Boc-L-aspartic acid-b-cyclohexyl ester. In the final coupling cycle, 2 mmole of 2-propylpentoic acid is coupled in the same manner as described for the N-Boc amino acids.

(b) Lysine Fmoc-deprotection

1. The resin is washed once with N-dimethylformamide.

2. The liquid is drained, then 5 to 7 mL 20% piperidine (in N-dimethyformamide) is added and the mixture was agitated for 3–5 minutes.

3. The liquid is drained, then the resin is washed five times with N-dimethyformamide.

(c) Coupling to chelating agent 1. 5 equivalents of 1-(p-isothiocyanatobenzyl) ethylenediaminetetraacetic acid, penta-t-butyl ester in DMF is added and the mixture agitated for 2 hours.

2. The liquid is drained, then the resin is washed five times with N-dimethyformamide.

(d) Oxidation.

The peptide resin is transferred to another reaction vessel and washed twice with 5 to 7 mL of dry dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 4 hours; then finally washing the resin three times with 5 to 7 mL of dry dichloromethane. In the last two oxidation cycle, the oxidation time is 3 hours.

(e) Deprotection and Removal.

It is important to realize that after removal of the protecting groups on the chelator, metal free conditions must be observed. That is, all glassware used must be rinsed prior to use with dilute metal-free HCl followed by rinsing with metal-free water to neutrality. All aqueous solutions must be prepared using metal-free water.

The peptide resin and a volume of anisole numerically equal to the weight of resin are transferred to a plastic reaction vessel. After purging the vessel and associated lines with nitrogen, the reaction mixture is cooled to −20° C. and 10 mL of hydrofluoric acid (HF) is distilled into the reaction vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(f) HPLC purification.

The crude product is dissolved in 10% acetonitrile (in water containing 0.1% trifluoroacetic acid) and is put onto a 2.5×300 mm C18 reverse phase column (VYDAC) and the effluent was monitored at 210 nm. A 20 minute gradient of 10% to 30% acetonitrile (in water containing 0.1% trifluoroacetic acid) is run at a flowrate of 1 mL/minute. If possible, the column should be packed in a metal free container and non-metallic lines used.

Example 32

$^{99m}$Tc Labelling of a thrombin-binding peptide which is crosslinked to metallothionein The labelling protocol is similar to that used by Brown, et. al., Analytical Biochemistry, 172: 22 (1988). A $^{99}$Mo/$^{99m}$Tc generator (DuPont) is the source of $^{99m}$TcO$_4$−. When reacted with stannous glucoheptonate (1 mL of $^{99m}$TcO$_4$− added to a Glucoscan kit) (DuPont), the $^{99m}$TcO(GH)$_2$ transchelates to metallothionein and metallothionein-peptide conjugates [Morelock & Tolman in Metallothionein (Kagi & Nordberg, eds.), pp. 247–253. Birkhauser, Basel]. Specifically, 1 volume of the compound of Example 27 is mixed with 1 volume of 0.3M sodium phosphate, pH=6.2, followed by 1 volume of $^{99m}$TcO(glucoheptonate)$_2$. After 2 hours at ambient temperature, the percentage of incorporation of the $^{99m}$Tc into peptide-chelator conjugate was quantitated by silica TLC chromatography in saline. Peptide-bound $^{99m}$Tc remained at the origin while the $^{99m}$TcO(GH)$_2$ moved to the solvent front.

Example 33

$^{111}$In Labelling of a Thrombin-Binding Peptide which is Attached to a Diethylenetriaminepentaacetic Acid Chelator The labelling protocol is similar to that used by Westerberg, et. al., J. Med. Chem. 32: 236 (1989). Carrier-free indium-111 chloride is added to an aliquot of the compound of Example 31 (100 μL at a concentration of 10 mg/mL in 0.05M citrate buffer, pH 6). After a 30 minute incubation at room temperature, the radiochemical yield of indium-111-labeled peptide is determined by incubating an aliquot (50 μL) of the solution with 0.05M DTPA, pH 6 (25 μL) for 10 minutes and then diluting this solution 50-fold with normal saline and spotting 3 μL of the resulting solution onto a TLC plate. Meares, et. al., Anal. Biochem., 142: 68 (1984). Subsequent TLC analysis indicates the amount of indium-111 bound to peptide.

Example 34

Preparation of methionine sulfone. In the final coupling cycle, 2 mmole of 2-propylpentanoic acid is coupled in the same manner as described for the N-Boc amino acids.

(b) Oxidation.

The peptide resin is transferred to another reaction vessel and washed twice with 5 to 7 mL of dry. dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. The oxidation time is 2 hours for each cycle. After the oxidation was complete, the resin was washed three times 5 to 7 mL each with dimethylformamide, dichloromethane, methanol and diethylether.

(c) Deprotection and Removal.

The peptide resin and a volume of anisole numerically equal to the weight of resin are transferred to a plastic reaction vessel. After purging the vessel and associated lines with nitrogen, the reaction mixture is cooled to –20° C. and 15 mL of hydrofluoric acid (HF) is distilled into the reaction vessel. The mixture is first stirred for 30 minutes at –20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of

[52] [SEQ. ID. NO. 93]
34

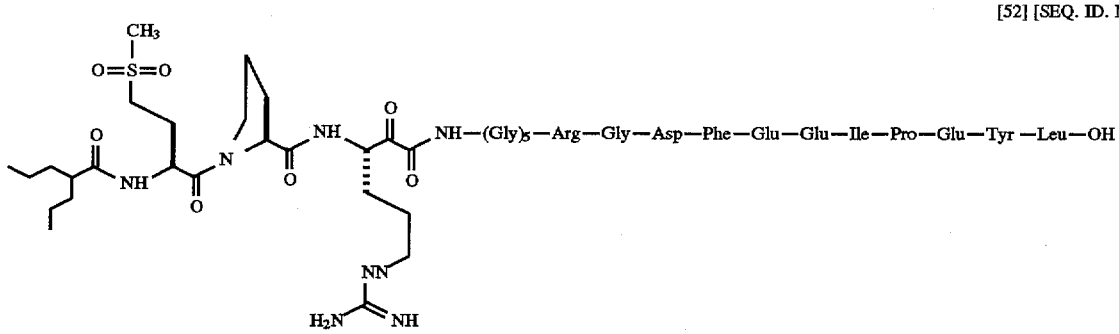

This compound is prepared using the tBOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester, N-Boc-L-phenylalanine, N-Boc-L-aspartic acid-b-cyclohexyl ester, N-Boc-glycine, N-a-Boc-N$^g$-tosyl-L-arginine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and N-Boc-L- diethyl ether, saving the aqueous phase each time. The aqueous phase is frozen and lyophilized to yield crude product.

(d) HPLC purification.

The crude product is dissolved in 10% acetonitrile (in water containing 0.1% trifluoroacetic acid) and is put onto a 2.5×300 mm C18 reverse phase column (VYDAC) and the effluent is monitored at 210nm. A 20 minute gradient of 10% to 35% acetonitrile (in water containing 0.1% trifluoroacetic acid) is run at a flowrate of 1 mL/minute.

Example 35

Preparation of a-Boc-L-serine-b-lactone

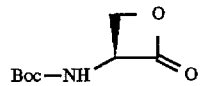

5.44 g (24.4 mmol, 1.0 equiv.) of Boc-L-serine hydrate (crushed) and 6.4 g (24.4 mmol, 1.0 equiv.) of triphenylphosphine (crushed) were dried in Vacuo at room temperature for 48 hours over phosphorous. pentoxide. The triphenylphosphine was taken up in 100 mL of 8:2 anhydrous acetonitrile/dry THF and cooled to −45° C. (acetone/dry ice bath) under nitrogen. 3.84 mL (24.4 mmol, 1.0 equiv.) of diethylazodicarboxylate (DEAD) was added dropwise via syringe over about 15 minutes and the reaction mixture was stirred for an additional 10 minutes at −55° C. A thick slurry of the DEAD-triphenylphosphine adduct resulted. The previously dried Boc-L-serine was taken up in 100 mL of anhydrous acetonitrile and added dropwise via canula to the activated DEAD/triphenylphosphine reagent. The reaction mixture was stirred at −5° C. for 1 hour and warmed to ambient temperature and stirred for an additional 1.5 hours. The volatiles were removed on the rotary evaporator and the resulting crude product was immediately taken up in a minimum amount of methylene chloride and flash chromatographed (30% ethyl acetate/hexane) to yield a white solid (2.53 g, 55 % yield). $^1$H-NMR (CDCl$_3$); 1.47 ppm (s, 9H), 4.42 ppm (t, 1H), 4.46 ppm (t, 1H), 5.11 ppm (quart., 1H), 5.26 (hr. s., 1H). $^{13}$C-NMR (CDCl$_3$); 28.0 ppm, 59.3 ppm, 66.5 ppm, 81.2 ppm, 154.5 ppm, 169.4 ppm.

Example 36

Preparation of a-N-Boc-b-amino-L-alanine

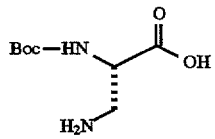

Anhydrous ammonia was bubbled through 400 mL of anhydrous acetonitrile for 25 minutes. To this saturated solution was added dropwise 2.0 g of N-Boc-L-serine-b-lactone 35 in 200 mL of anhydrous acetonitrile over 1 hour. After addition was complete, the reaction mixture was stirred at ambient temperature for an additional 16 hours. The volatiles were removed in vacuo (a liquid nitrogen trap was used to trap the ammonia) to yield a white solid (2.1 g, 96 % yield). It was one spot by TLC (Rf=0.8; 70% propanol/water). $^1$H-NMR (CDCl$_3$); 1.47 ppm (s, 1H), 3.20 ppm (dd, 1H), 3.39 ppm (dd, 1H), 4.16 ppm (br. s, 1H). $^{13}$C-NMR; 28.3 ppm, 41.9 ppm, 53.7 ppm, 82.3 ppm, 158.2 ppm, 175.7 ppm.

Example 37

Preparation of a-N-Boc-b-(methylsulfonylamino)-L-alanine

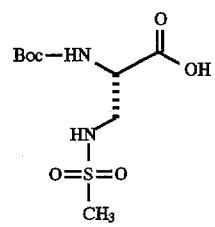

To a solution of a-N-Boc-b-amino-L-alanine 36 (1.92 g, 10 mmol) in 50 mL dry dichloromethane at 0° C., is added triethylamine (2.79 mL, 20 mmol) followed by mesyl chloride (1.55 mL, 20 mmol) dropwise. After the addition, the reaction mixture is warmed to room temperature and allowed to stir for two hours. After this time, the reaction mixture is poured into 50 mL of ethyl acetate and 50 mL of 1M aqueous hydrochloric acid, and the title compound is allowed to partition into the organic phase. The organic phase is separated, dried over anhydrous magnesium sulfate, then reduced to dryness in vacuo to provide the title compound.

Example 38

Preparation of

[53] [SEQ. ID. NO. 94]
8

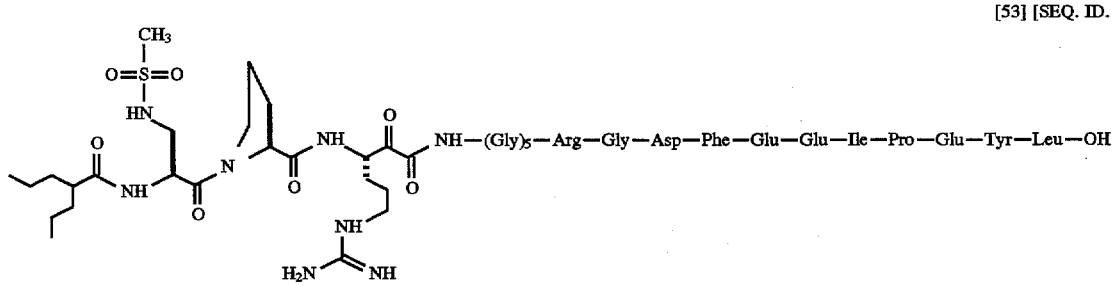

This compound is prepared using the t-BOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L-glutamic acid-g-cyclohexyl ester; N-Boc-L-phenylalanine, N-Boc-L-aspartic acid-b-cyclohexyl ester, N-Boc-glycine, N-a-Boc-N$^g$-tosyl-L-arginine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and a-N-Boc-b-(methylsulfonylamino)-L-alanine 37. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycle, the oxidation time is 2 hours for each cycle. After the oxidation was complete, the resin was washed three times 5 to 7 mL each with dimethylformamide, dichloromethane, methanol and diethylether.

(c) Deprotection and Removal.

The peptide resin and a volume of anisole numerically equal to the weight of resin are transferred to a plastic reaction vessel. After purging the vessel and associated lines with nitrogen, the reaction mixture is cooled to –20° C. and 15 mL of hydrofluoric acid (HF) is distilled into the reaction vessel. The mixture is first stirred for 30 minutes at –20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product.

(d) HPLC purification.

The crude product is dissolved in 10% acetonitrile (in water containing 0.1% trifluoroacetic acid) and is put onto a 2.5×300 mm C18 reverse phase column (VYDAC) and the effluent is monitored at 210 nm. A 20 minute gradient of 10% to 35% acetonitrile (in water containing 0.1% trifluoroacetic acid) is run at a flowrate of 1 mL/minute.

Example 39

Preparation of a-N-Boc-b-(methoxycarbonylamino)-L-alanine

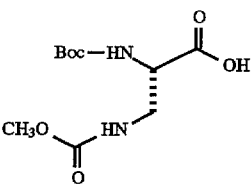

39

To a suspension of a-N-Boc-b-amino-L-alanine 36 (1.92 g, 10 mmol) and solid potassium carbonate (2.76 g, 20 mmol) in 50 mL dry tetrahydrofuran at room temperature, is added methylchloroformate (f.55 mL, 20 mmol) dropwise. The reaction mixture is allowed to stir for twelve hours, then 100 mL of ethyl acetate is added. The reaction mixture is then decanted away from the potassium carbonate, poured into 50 mL of ethyl acetate and 50 mL of 1M aqueous hydrochloric acid, and the title compound is allowed to partition into the organic phase. The organic phase is separated, dried over anhydrous magnesium sulfate, and then reduced to dryness in vacuo to provide the title compound.

Example 40

Preparation of

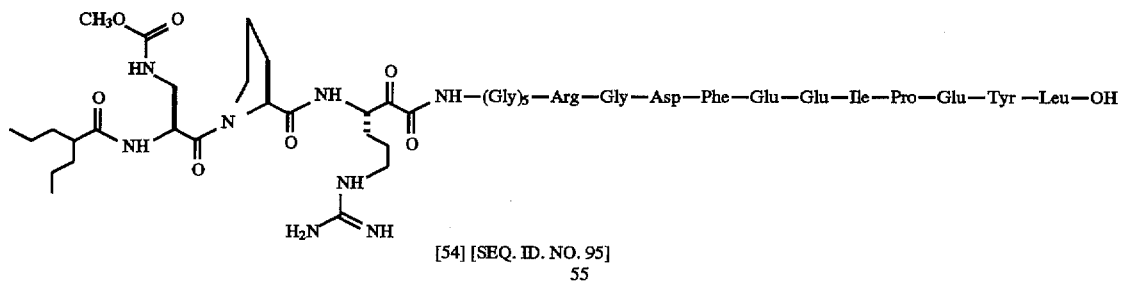

40

[54] [SEQ. ID. NO. 95]

This compound is prepared using the t-BOC Coupling Protocol as described in Example 1, followed by oxidation, deprotection and removal of the peptide from the resin, and HPLC purification.

(a) Coupling.

Boc-L-leucine-Pam Resin, the starting resin, is purchased from Advanced ChemTech, Louisville, Ky.).

N-Boc-O-(2-bromobenzyloxycarbonyl)-L-tyrosine is first coupled to the resin, followed by N-Boc-L-glutamic acid-g-cyclohexyl ester, N-Boc-L-proline, N-Boc-L-isoleucine, N-Boc-L-glutamic acid-g-cyclohexyl ester, N-Boc-L- glutamic acid-g-cyclohexyl ester, N-Boc-L-phenylalanine, N-Boc-L-aspartic acid-b-cyclohexyl ester, N-Boc-glycine, N-a-Boc-$N^g$-tosyl-L-arginine, N-Boc-glycine, N-Boc-glycine, N-Boc-glycine, N-Boc-glycine, N-Boc-glycine, 6-nitroguanidino-3-(S)-(1,1-dimethylethoxy)methanamido-2-hydroxyhexanoic acid 7, N-Boc-L-proline, and a-N-Boc-b-(methoxycarbonylamino)-L-alanine 39. In the final coupling cycle, 2 mmole of 2-propylpentoic acid is coupled in the same manner as described for the N-Boc amino acids.

(b) Oxidation.

The peptide resin is transferred to another reaction vessel and washed twice with 5 to 7 mL of dry dichloromethane.

The a-hydroxy group of the resin-bound peptide is oxidized to a keto group by treating the resin to three oxidation cycles. Each oxidation cycle is performed by suspending the resin in a mixture of 5 mL of dry dichloromethane and 5 mL of dry dimethylsulfoxide; deoxygenating the mixture with nitrogen; adding 5 mmole 1-ethyl-3-(3-dimethylaminopropyl)carbodiimide hydrochloride salt (EDAC-HCl), 2 mmole dichloroacetic acid (DCA), 2 mL of dry dichloromethane and 2 mL of dry dimethylsulfoxide; stirring the reaction mixture for 2 hours; then finally washing the resin three times with 5 to 7 mL of dry dichloromethane. In the last two oxidation cycle, the oxidation time is 2 hours for each cycle. After the oxidation was complete, the resin was washed three times 5 to 7 mL each with dimethylformamide, dichloromethane, methanol and diethylether.

(c) Deprotection and Removal.

The peptide resin and a volume of anisole numerically equal to the weight of resin are transferred to a plastic reaction vessel. After purging the vessel and associated lines with nitrogen, the reaction mixture is cooled to −20° C. and 15 mL of hydrofluoric acid (HF) is distilled into the reaction vessel. The mixture is first stirred for 30 minutes at −20° C., then for 120 minutes at 0° to 10° C. After removing the HF by evaporation, 20 mL diethyl ether is added, then decanted. The resin is then transferred to an extraction funnel, washed with 3–20 mL portions of diethyl ether, then extracted with 3–50 mL portions of 20% acetic acid (in water). The extracts are combined and then extracted with 3–25 mL portions of diethyl ether, saving the aqueous phase each time. The aqueous phase is frozen and lyophilized to yield crude product. (d) HPLC purification.

The crude product is dissolved in 10% acetonitrile (in water containing 0.1% trifluoroacetic acid) and is put onto a 2.5×300 mm C18 reverse phase column (VYDAC) and the effluent is monitored at 210 nm. A 20 minute gradient of 10% to 35% acetonitrile (in water containing 0.1% trifluoroacetic acid) is run at a flowrate of 1 mL/minute.

Example A

Amidolytic Thrombin Assay

The ability of the compounds of the present invention to act as inhibitors of thrombin catalytic activity in comparison to Hirulog-1 (compound 25) was assessed by determining their inhibition constant, Ki.

Enzyme activity was determined using the chromogenic substrate Pefachrome t-PA ($CH_3SO_2$-D-hexahydrotyrosine-glycyl-L-arginine-p-nitroaniline, obtained from Pentapharm Ltd.). The substrate was reconstituted in deionized water prior to use. Purified human a-thrombin was obtained from Enzyme Research Laboratories, Inc. The buffer used for all assays was HBSA (10 mM HEPES, pH 7.5, 150 mM sodium chloride, 0.1% bovine serum albumin)

Ki values were determined for test compounds using the following methodologies:

1) For test compounds exhibiting slow binding or slow-tight binding kinetics (as compounds 8, 10 and 11), Ki values were determined using the relationships developed by Williams and Morrison, Methods in Enzymology, 63: 437 (1979) by determining the apparent first-order rate constant ($k_{obs}$) which describes the rate of equilibration from the initial to the steady state velocity (Vs). The assay was conducted by combining in appropriate wells of a Corning microtiter plate, 50 mL of HBSA, 50 mL of the test compound at a specified concentration diluted in HBSA (or HBSA alone for $V_{o(uninhibited\ velocity)}$ measurement), and 50 mL of the chromogenic substrate diluted in HBSA. At time zero, 50 mL of a-thrombin diluted in HBSA, was added to the wells yielding a final concentration of 0.25 nM in a total volume of 200 mL. Velocities of Pefachrome-tPA substrate hydrolysis which occurred over a 40 minute time period was measured by the change in absorbance at 405 nm using a Thermo Max® Kinetic Microplate Reader. The concentration of substrate in this assay was 400 mM (~10-times Km) and the extent of substrate hydrolysis was less than 5% over the course of this assay. The linear relationship between $k_{obs}$ and inhibitor concentration is indicative of a competitive, one step mechanism and was used to calculate $k_{on}$ and $k_{off}$ which yielded a value for Ki after taking into consideration the concentration and Km (38.5 mM) of the substrate in the assay.

2) A second method was used to measure the intrinsic dissociation constant (Ki*) for compound 8 which is independent of the inhibitory mechanism. In this assay, HBSA (50 mL), a-thrombin (50 μL, 0.25 nM) and inhibitor (50 μL, covering a broad concentration range, 10–1000 pM), were combined in appropriate wells and incubated for 30 minutes at room temperature prior to the addition of substrate Pefachrome-t-PA (50 μL, 260 mM, ~7-times Km). The initial velocity of Pefachrome t-PA hydrolysis was measured by the change in absorbance at 405 nm using a Thermo Max® Kinetic Microplate Reader over a 2 minute period in which less than 5% of the added substrate was utilized. The relationship between the ratio of the inhibited steady-state velocity (Vs) and the uninhibited velocity (Vo) to the concentration of inhibitor [$I_t$], was analyzed using Equation 1 developed by Morrison, J. F., Biochim. Biophys. Acta, 185: 269 (1969) for inhibitors which deplete a significant amount of the total enzyme ($E_t$) over the course of the assay (designated tight binding inhibitors):

$$Vs/Vo=\{([E_t]-[I_t]-Ki^*)+[([I_t]+Ki^*-[E_t])^2+4Ki^*[E_t]]^{1/2}\}/2[E_t] \quad \text{Equation 1}$$

Ki* was determined by fitting Vs/Vo verses [I] using Equation 1 by non-linear regression analysis.

3) The final method for Ki determination was used for test compounds showing rapid, reversible kinetics of inhibition (compound 9 and compound 25 (Hirulog-1)),using the assay protocol described above for slow-binding inhibitors (Method 1). Ki values were determined by non-linear regression analysis of the initial velocities of substrate hydrolysis taken over a 2 minute period following the addition of a-thrombin, at several substrate (15–300 mM) and inhibitor concentrations (Compound 9, 0–300 mM; Hirulog-1 (Compound 25), 0–5 nM) using the relationships developed by Dixon, M., Biochem. J., 129: 197 (1972). The best fit of the data for both compounds was to the equation describing competitive inhibition.

Table I below gives the Ki values for test compounds 8 to 11 in comparison with Hirulog-1 (compound 25).

TABLE I

Inhibitor Constants (Ki)*

| Compound | Ki (nM) | Ki* (nM) |
|---|---|---|
| Compound 8 | 0.0019 | 0.0014 |
| Compound 9 | 46.06 | NA |
| Compound 10 | 0.040 | ND |
| Compound 11 | 0.0078 | ND |
| Compound 25 (Hirulog-1) | 0.437 | NA |

*The data is representative of at least two independent experiments run in triplicate.
NA-not applicable
ND-not performed The good agreement between the values of Ki and Ki* seen for compound 8 indicate that this compound inhibits thrombin in a predominately one-step competitive, tight-binding mechanism. This data also demonstrates the remarkable increase in inhibitory potency that can be achieved singlely through the incorporation of the a-keto-amide transition-state functionality as evidenced by the almost 23,000-fold difference in Ki between compound 8 and 9. In addition this data also demonstrates that compound 8 is 230-fold more potent than the prototypical bifunctional, clearable, thrombin inhibitor, Hirulog-1 (compound 25), as determined by direct comparison under the assay conditions described above even though the calculated Ki for Hirulog-1 (compound 23) is lower than previously reported by Witting, J. I. et al., Biochem. J., 283:737 (1992). Compound 10 differs from compound 8 in having an additional glutamic acid residue at position $C_5$ in group C as described in Formula I within the Detailed Description. Although the sequence of this peptide in compound 10 is identical to that described for compound 25 (Hirulog-1), it resulted in an over 20-fold decrease in the inhibitory potency compared to the parent, compound 8 having only a single glutamic acid at this position. Changing the asparagine residue in compound 10 at position $B_2$ in group B shown in Formula I to arginine, results in an approximately 5-fold increase in inhibitory potency compared to compound 10, indicating that the overall charge density in the region of this compound encompassing groups B and C in Formula I may be important in determining the overall potency of this inhibitor.

Example B

Thrombin-Induced Clotting of Purified Fibrinogen

Compound 8 and Hirulog-1 (compound 25) were compared in an assay designed to measure the inhibition of thrombin using purified fibrinogen as the substrate using a modification of the method described by Witting, J. I. et al., Biochem. J. 283:737 (1992). Compound 8 or Hirulog-1 (compound 25) were pre-incubated with a-thrombin over a broad concentration range at 25° C. in 300 mL of Buffer A (150 mM NaCl, 30 mM $CaCl_2$, 10 mM imidazole, 8.8 mg/mL polyethylene glycol (PEG 6000), pH 7.4) for 0, 30, and 60 minutes prior to the addition 100 mL of purified human fibrinogen (American Diagnostica, Greenwich, Conn.) which had been reconstituted in Buffer B (30 mM NaCl, 10 mM imidazole, pH 7.4) to a concentration of 8 ng/mL. The clotting time of fibrinogen following the addition of the thrombin/inhibitor complex was measured optically using the Coag-A-Mate XC automated coagulometer (General Diagnostics, Organon Technica, Oklahoma City, Okla.).

Figure 2:
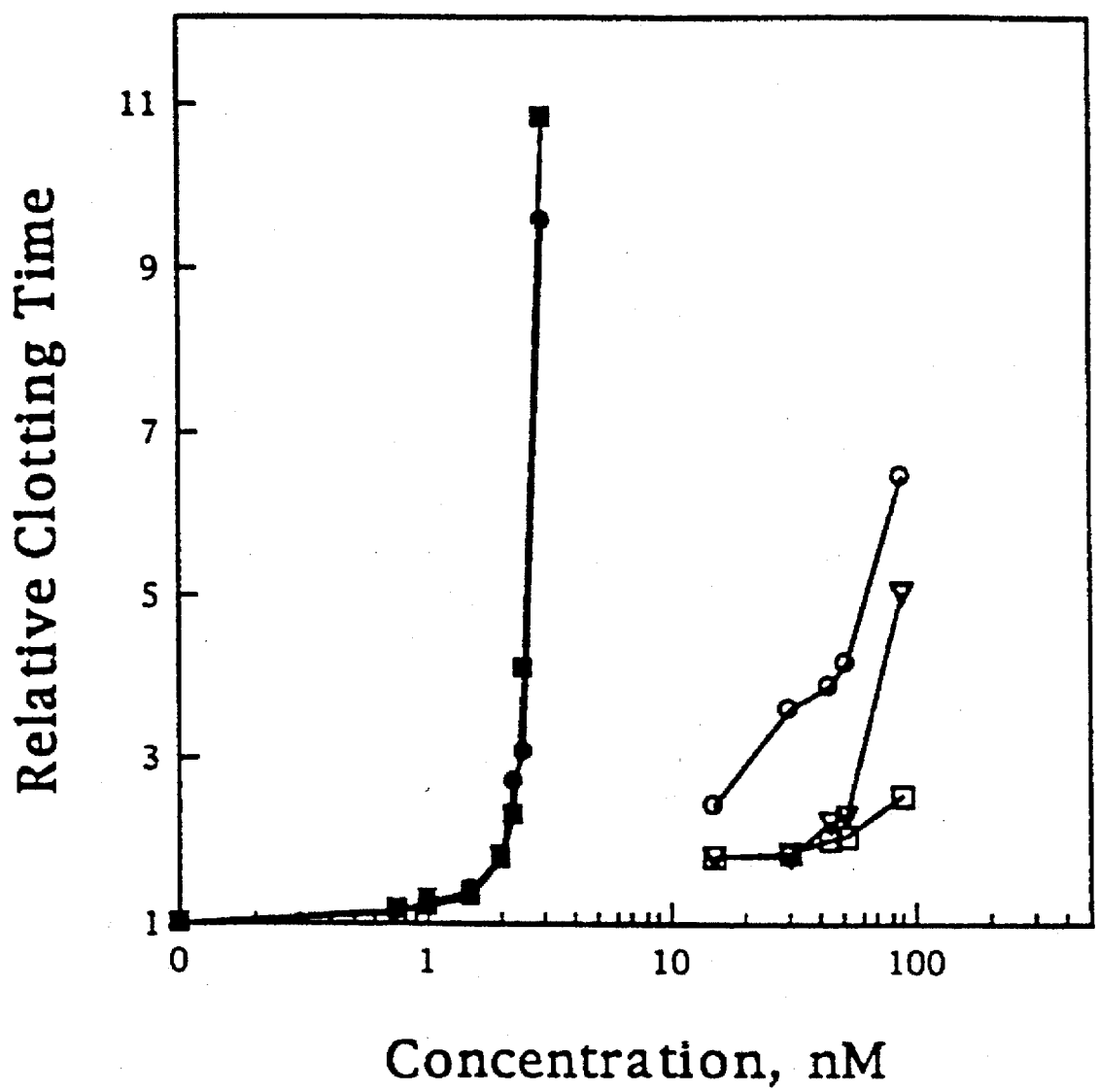
FIG. 2 depicts the comparative inhibitory effects of compound 8 and Hirulog-1 (compound 25) on a-thrombin-mediated fibrin formation using purified human fibrinogen. Inhibition is reflected as an increase in the relative clotting time which is the ratio of the control (uninhibited) clotting time/experimental clotting time. The control clotting time in this assay is 16.2±0.78 sec. Compound 8 (solid symbols) and Hirulog-1 (compound 25; open symbols) were preincubated with a-thrombin for 0 (m,l) 30 (Δ,s), and 60 (o,n) minutes prior to the addition of fibrinogen.

The results of this assay are shown in FIG. 2. In this figure, Compound 8 (solid symbols) and Hirulog-1 (compound 25; open symbols) were preincubated with a-thrombin for 0 (m,1) 30 (Δ,s), and 60 (o,n) minutes prior to the addition of fibrinogen.

The data in FIG. 2 demonstrate that Compound 8 can dose-dependently inhibit the generation of fibrin catalyzed by thrombin as measured by an increase in clotting time relative to the uninhibited control. This inhibition is reflected as an increase in the relative clotting time which is the ratio of the control (uninhibited) clotting time/experimental clotting time. The control clotting time in this assay is 16.2±0.78 sec.

In addition this data demonstrates that compound 8 is significantly more potent than Hirulog-1 (compound 25) in this assay and is not proteolytically inactivated by thrombin upon prolonged incubation (up to 60 minutes) with the enzyme prior to the addition of the fibrinogen substrate. This is in contrast to Hirulog-1 (compound 25) which appears to be sensitive to proteolytic degradation with re-emergence of thrombin activity consistent with the results presented by Witting, J. I. et al., Biochem. J., 283:737 (1992) and Rubens, F. D., et al., Thromb. Haemostas., 69:130–134 (1993).

Example C

Ex Vivo coagulation assay

The ex vivo anticoagulant effects of compound 8 in comparison with Hirulog-1 (compound 25) were determined by measuring the prolongation of the activated partial thromboplastin time (APTT) over a broad concentration range of each added inhibitor, using pooled normal human plasma. Fresh frozen pooled normal human plasma was obtained from George King Biomedical, Overland Park, Kans.. Measurements APTT was made using the Coag-A-Mate RA4 automated coagulometer (General Diagnostics, Organon Technica, Oklahoma City, Okla.) using the Automated APTT reagent (Organon Technica, Durham, N.C.) as the initiator of clotting according to the manufacturers instructions. The assay was conducted by making a series of dilutions of the test compounds in rapidly thawed plasma followed by adding 200 mL to the wells of the assay carousel.

Figure 3:
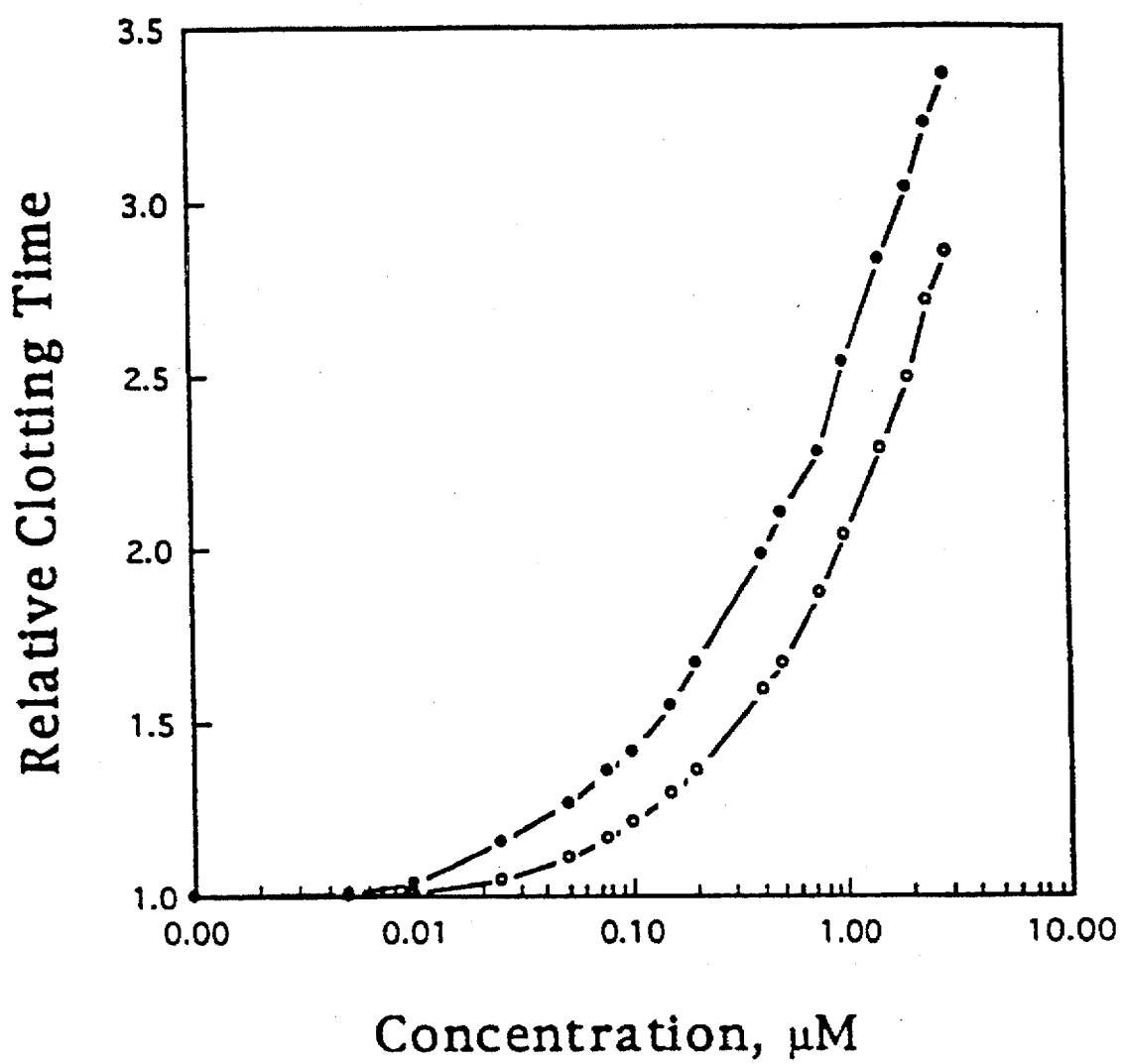
FIG. 3 depicts the comparative effects of compound 8 (open symbols) and Hirulog-1 (compound 25) (closed symbols) on the activated partial thromboplastin time (APTT) of normal citrated human plasma.

FIG. 3 depicts the effect of compound 8 (open symbols) and Hirulog-1 (compound 25) (closed symbols) on the activated partial thromboplastin time (APTT) of normal citrated human plasma.

As shown in this figure, both compounds prolonged the APTT in a dose dependent manner.

Example D

EX Vivo Platelet Aggregation Assay Thrombin-Induced Aggregation in Washed Human Platelets The ability of compound 8 and Hirulog-1 (compound 25) to inhibit thrombin-induced platelet aggregation were determined using washed human platelets. Washed human platelets were prepared from freshly isolated venous blood obtained from normal, healthy volunteers who had not taken any medication which might affect platelet function, according to the procedure of Connolly, T. M. et al., J. Biol. Chem., 267: 6893. (1992). Inhibitors, were added in a volume of 20 mL to 350 mL of prewarmed washed platelets in a siliconized glass cuvette (Chronolog Corp., Hayertown, Pa.) followed by 10 mL of 0.25M $CaCl_2$. The rate and extent of aggregation were measured for 5–15 minutes by the change in light transmission in a stirred cuvette, following the addition of 20 mL of a-thrombin (final concentration 2 nM), using a Chronolog Whole Blood Aggregometer equipped with the Aggro/Link data acquisition system (Chronolog Corp., Hayertown, Pa.). The extent of inhibition was determined by measuring the change in the amplitude (extent) of the aggregation response compared to the control (uninhibited) response over the 1 minute period following the addition of thrombin. The inhibitory effect of the test compounds was measured over a broad concentration range and is reported as the concentration required to inhibit aggregation by 50% ($IC_{50}$).

TABLE II

Effect of Compounds 8 and Hirulog-1 (compound 25) on thrombin-induced platelet aggregation using washed human platelets.

| Compound | $IC_{50}$ (nM)* |
|---|---|
| Compound 8 | 25 ± 8 |
| Hirulog-1 (compound 25) | 16 ± 3 |

*represents the mean ± standard deviation from three independent determinations.

Figure 4A:
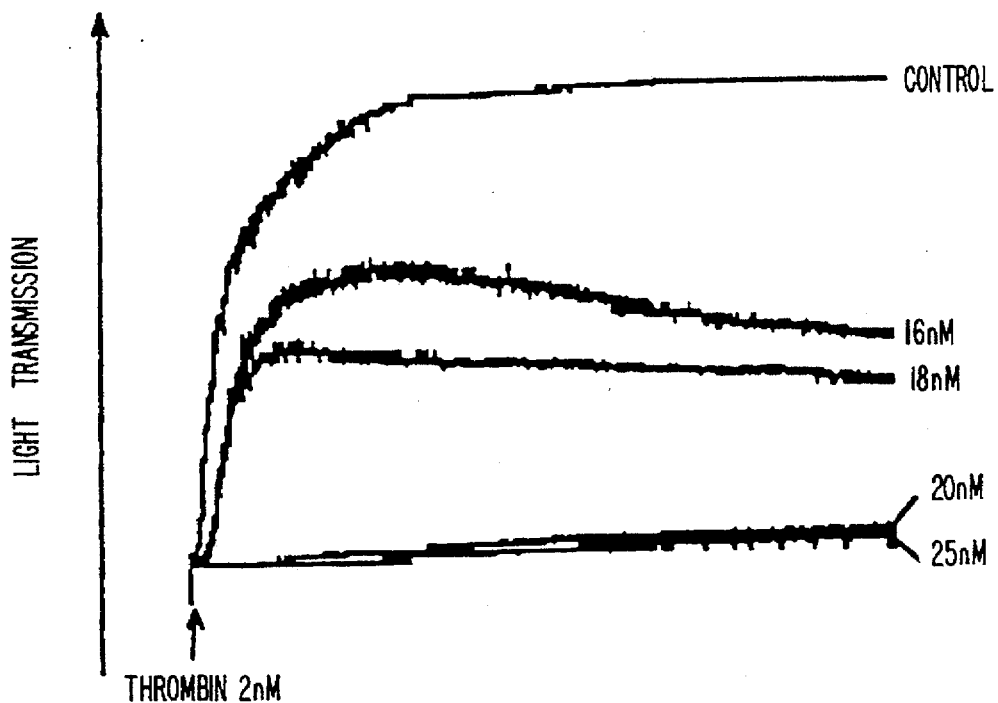
FIG. 4(A–B) depicts the effect of increasing concentrations of compound 8 (panel A) and Hirulog-1 (compound 25) on the aggregation of washed human platelets induced by the addition of thrombin.
Figure 4B:
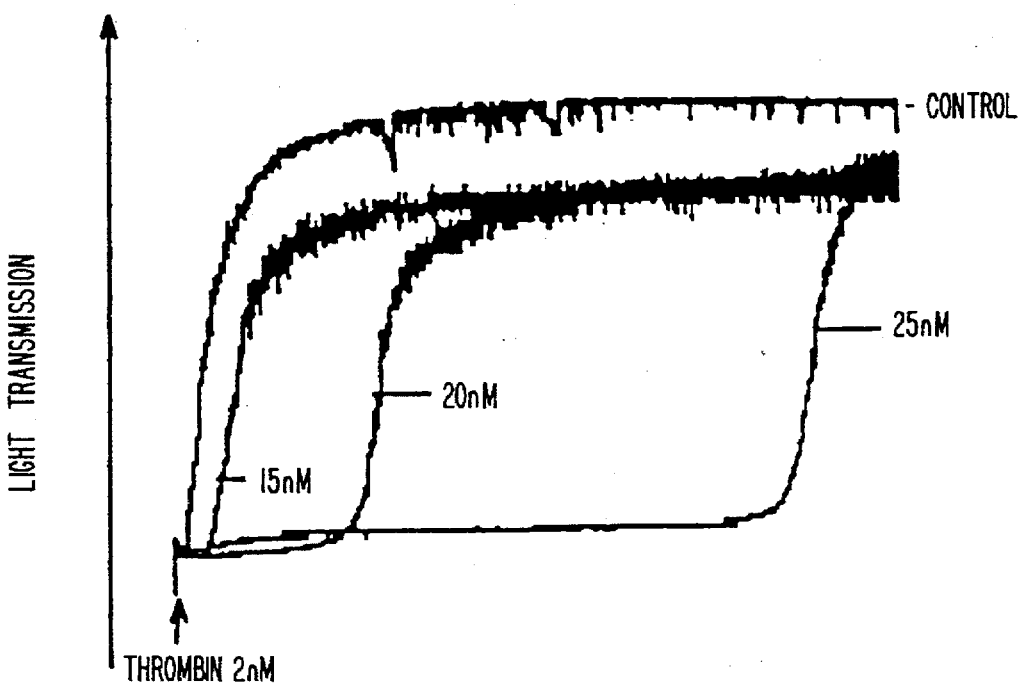

This data indicates that compound 8 and Hirulog-1 (compound 25) equally inhibit thrombin-induced platelet aggregation in vitro when the extent of aggregation is measured for the initial 1 minute following thrombin addition. However, as shown in FIG. 4A, the maximal inhibition of aggregation with compound 8 obtained at a concentration of 20 nM was stable with no recovery of aggregation over the 15 minute course of the assay. This was in contrast to Hirulog-1 (compound 25) which did not cause sustained inhibition of the aggregation response at the same or higher concentrations of inhibitor (FIG. 4B). The functional differences between compound 8 and Hirulog-1 (compound 25) in the platelet aggregation assay is similar to the effects of these two inhibitors in the purified fibrin formation assay shown in FIG. 2 and can be attributed to the susceptibility of Hirulog-1 (compound 25) to proteolytic inactivation by thrombin which does not occur with compound 8 due to the presence of the proteolytically stable transition state functionality.

Example E

Experimental Models of Thrombosis in Rats

The antithrombotic properties of compound 8 and Hirulog-1 (compound 25) were evaluated using the following established in vivo experimental models of acute thrombosis.

1. Venous Stasis in Rats.

This is one of the most commonly used models in the evaluation of antithrombotic compounds. Hladovec, *J. Thromb. Res.*, 43:539–544 (1986) In this model a localized clot made up of primarily fibrin is formed in a segment of the inferior vena cava (IVC) in which an artificial stasis is induced by ligature following the systemic infusion of thromboplastin used as the thrombogenic stimulus. Talbot, M. D., et. al., Thromb. Haemostas., 61: 77–80 (1989) The antithrombotic effect of the compound 8 and Hirulog-1 (compound 25), was determined by measuring the final clot weight recovered from the isolated segment of the IVC as the primary end point in the model following systemic, intravenous administration of each compound at several dosing regimens.

Male Harlan Sprague Dawley rats (420–450 g) were acclimated at least 72 hours prior to use. The animals were fasted for 12 hours prior to surgery with free access to water. The animals were anesthetized with a sodium pentobarbital (Nembutal) given intraperitoneally at a dose of 50 mg/kg body weight and placed on a isothermal pad to maintain body temperature. The level of anesthesia was monitored every 15 minutes by: neuro-response to a tail pinch, respiration and body core temperature. The desired depth of surgical anesthesia was maintained by administering subsequent doses (5 mg/kg) intravenously. The left femoral artery was catheterized with polyethylene tubing (PE50) using standard procedures for blood pressure monitoring and blood sampling. The left and right femoral veins were catheterized with PE50 tubing for delivery of anesthetic and test compounds respectively.

Following anesthesia the animals were randomized in either a control (saline infusion) or treatment group (Compound 8 or Hirulog-1 (compound 25)) with at least 4 animals per group per dose. The compounds or saline were administered via the femoral catheter as a bolus infusion of 100 mg/kg followed by a continuous intravenous infusion for a period of 30 minutes of 10, 20 or 40 mg/kg/min for compound 8 and 40, 60 or 80 mg/kg/min for Hirulog-1 (compound 25). Blood pressure, heart rate, core temperature and respiration were monitored continuously.

The abdomen of the animals is opened by making a vertical midline incision followed by isolation of the IVC using dissection. The segment extends from below the renal to above the iliac vessels (about 2 cm in length). The peripheral blood vessels are tied off and a ligature is loosely placed at the distal and proximal ends of the isolated segment. Rabbit brain thromboplastin (RBT)(Sigma Chemical Co., St. Louis Mo.) is prepared by resuspending the contents of the vial with 2 mL of sterile saline pre-warmed to 37° C. At the end of the 30 minute infusion period, RBT is systemically administered as a bolus injection (1.5 mL/kg) via the femoral catheter. Stasis is induced within the isolated IVC segment by securing the proximal and distal ligature 10 sec following the administration of the RBT. Following a 30 minute period of stasis the tied off IVC segment is removed and the contents weighed. Clot formation was defined as %clot: [Weight of the isolated clot/(Weight of the intact segment-the weight of the empty segment)] ×100. This method was used to correct for slight differences in segment size and fluid content.

Following termination of the experiment the animal was euthanized with a 120 mg/kg dose of Nembutal.

The efficacy of the compound 8 compared to Hirulog-1 (compound 25) in this in vivo model is shown in Table III below.

TABLE III

Efficacy of the Compound 8 and Hirulog-1 (compound 25) in the Rat Venous Stasis Model.

| Treatment Group | % Clot* |
|---|---|
| Control | 25.18 ± 0.86 (n = 6) |
| Compound 8 | |
| Group 1 | 22.03 ± 3.6 (n = 4) |
| Group 2 | 8.25 ± 5.1* (n = 4) |
| Group 3 | 0** (n = 4) |
| Hirulog-1 (compound 25) | |
| Group 1 | 25.75 ± 3.71 (n = 4) |
| Group 2 | 26.50 ± 3.59 (n = 4) |
| Group 3 | 25.75 ± 0.41 (n = 4) |

TABLE III-continued

Efficacy of the Compound 8 and Hirulog-1 (compound 25) in the Rat Venous Stasis Model.

| Treatment Group | % Clot[a] |
| --- | --- |
| Control-no treatment | |
| Group 1-0.1 mg/kg i.v. bolus + 10 (compound 8) or 40 (Hirulog-1 (compound 25)) mg/kg/min i.v. infusion | |
| Group 2-0.1 mg/kg i.v. bolus + 20 (compound 8) or 60 (Hirulog-1 (compound 25)) mg/kg/min i.v. infusion | |
| Group 3-0.1 mg/kg i.v. bolus + 40 (compound 8) or 80 (Hirulog-1 (compound 25)) mg/kg/min i.v. infusion | |

[a]% Clot is defined as: [Isolated clot/(Intact segment − Empty segment)] × 100. Numbers represent the mean ± S.E.M.
*p ≦ 0.05 vs Control by one-way ANOVA followed by Newman-Kuels Test.
**p ≦ 0.01 vs Control by one-way ANOVA followed by Newman-Kuels Test.

This data demonstrates that compound 8 is very efficacious in dose-dependently preventing venous thrombus formation induced by stasis and thromboplastin in this rat model of venous thrombosis compared to Hirulog-1 (compound 25) which did not have any effect of thrombus formation in this setting. The lack of efficacy observed for Hirulog-1 (compound 25) in this model is presumably a result of the proteolytic inactivation of this inhibitor by thrombin generated within the isolated IVC segment during the 30 minutes of induced stasis. This is in contrast to compound 8 which is not proteolytically inactivated by thrombin under these conditions and thus serves as an effective antithrombotic agent in this model. This in vivo data correlates well with the results obtained with these two compounds in vitro in the purified fibrin formation and in ex vivo thrombin-induced platelet aggregation assays described above.

2. Rat model of FeCl$_3$-induced platelet-dependent arterial thrombosis.

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60: 269–280. (1990). In this model a platelet-rich, occlusive thrombus is formed in a segment of the rat carotid artery treated with a fresh solution of FeCl$_3$ absorbed to a piece of filter paper. The FeCl$_3$ is thought to diffuse into the treated segment of artery and causes de-endothelialization resulting in thrombus formation. The effect of a test compound on the incidence of occlusive thrombus formation following the application of the FeCl$_3$ is monitored by ultrasonic flowtometry and is used as the primary end point. The use of flowtometry is a modification of the original procedure in which thermal detection of clot formation was employed. Kurz, K. D., Main, B. W., and Sandusky, G. E., Thromb. Res., 60: 269–280 (1990).

Male Harlan Sprague Dawley rats (420–450 g) were acclimated at least 72 hours prior to use and fasted for 12 hours prior to surgery with free access to water. The animals were prepared, anesthetized with Nembutal with catheters for blood pressure monitoring, drug and anesthesia delivery being implanted as described above. The left carotid artery was exposed and isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline infusion) or treatment group with test compounds (compound 8 or Hirulog-1 (compound 25)) with at least 3 animals per group per dose. The test compounds were administered as described above after placement of the flow probe and stabilization of the preparation for a period of 60 minutes prior to the thrombogenic stimulus. At t=0, a 3 mm diameter piece of filter paper (Whatman #3) soaked with 10 mL of a 35% solution of fresh FeCl$_3$ (in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point. Following the 60 minute observation period the flow probe was removed and the area cleared of all excess fluid. The distal and proximal sutures were tied off and arterial clamps placed on the far proximal and distal ends of the segment. The isolated segment was cut out, blotted dry on filter paper and weighed. The segment was re-weighed following removal of the clot and the difference recorded as total % clot (see above). Weights were recorded on only those segments which had detectable thrombus. Following the procedure the animals were euthanized as described above.

The efficacy of the compound 8 and Hirulog-1 (compound 25) in this in vivo model is shown in Table IV below.

TABLE IV

Efficacy of Compound 8 and Hirulog-1 (compound 25) in the FeCl$_3$ Model of Thrombosis in Rats.

| Treatment Group[a] | Incidence of Occlusion[b] | % Clot[c] |
| --- | --- | --- |
| Control | 6/6 | 70.9 ± 1.21 (n = 6) |
| Compound 8 | | |
| Group 1 | 5/6 | 66.14 ± 3.83 (n = 5) |
| Group 2 | 4/6 | 42.28 ± 12.6 (n = 4) |
| Group 3 | 3/6 | 46.13 ± 6.75 (n = 3) |
| Group 4 | 0/5* | 0 |
| Hirulog-1 (compound 25) | | |
| Group 1 | 3/3 | 70.1 ± 5.5 (n = 3) |
| Group 2 | 5/6 | 59.42 ± 4.34 (n = 5) |
| Group 3 | 5/6 | 45.3 ± 11.63 (n = 5) |
| Group 4 | 0/6** | 0 |

[a]Control-no treatment (saline infusion)
Group 1-0.1 mg/kg i.v. bolus + 5 mg/kg/min i.v. infusion
Group 2-0.1 mg/kg i.v. bolus + 10 mg/kg/min i.v. infusion
Group 3-0.1 mg/kg i.v. bolus + 20 mg/kg/min i.v. infusion
Group 4-0.1 mg/kg i.v. bolus + 40 mg/kg/min i.v. infusion
[b]occlusion is defined as the establishment of zero blood flow through the treated segment of the carotid artery.
[c]% Clot is defined as: [Isolated clot/(Intact segment − Empty segment)] × 100. Numbers represent the mean ± S.E.M. in the designated number of animals.
*p ≦ 0.01 vs Control by Chi-Square Analysis
**p ≦ 0.005 vs Control by Chi-Square Analysis These in vivo data demonstrated the antithrombotic efficacy of the Compound 8 compared to Hirulog-1 (compound 25) in a rodent model of platelet-dependent arterial thrombosis.

Example F

Inhibition of Clot-Associated Thrombin

The association of catalytically active thrombin with fibrin rich clot is believed to render this pool of thrombin activity resistant to the actions of certain anticoagulants such as heparin which require an interaction with the serpin antithrombin III for activity. Weitz, J. I. et.al., J. Clin.

Invest., 86: 385–391 (1990). This resistance to inhibition is believed to be among the reasons why heparin anticoagulants are not particularly effective either in the prevention or treatment of arterial thrombosis (Hirsh, J. N. Engl. J. Med. 324: 1565–1574 (1991).

Recombinant Hirudin (rHIR) (CGP 39393).was supplied by Ciba-Geigy, Horsham, UK. D-Phe-Pro-ArgCH$_2$Cl was obtained Calbiochem.

The relative inhibition of fluid-phase and clot-associated thrombin activity by compound 8 was compared to Hirulog-1 (compound 25) and rHIR, using the methodologies of Weitz, J. I. et.al. J. Clin. Invest., 86: 385–391 (1990).

1. Inhibition of Fluid-phase Thrombin.

Human a-thrombin (2 U/ml) was incubated with citrated plasma for 60 minutes at 37° C. in the absence or presence of varying concentrations of each of the inhibitors. At timed intervals, 100 µl aliquots were removed and the reaction was terminated by the addition of D-Phe-Pro-ArgCH$_2$Cl (5 µM, final concentration). Unreacted fibrinogen was then precipitated with ethanol, and the ethanol supernatants were assayed for fibrinopeptide A (FPA). Thrombin addition to plasma results in rapid FPA generation which reaches a plateau in minutes as the thrombin is complexed and inactivated by fluid-phase antiproteases.(e.g. antithrombin III).

Figure 5A:
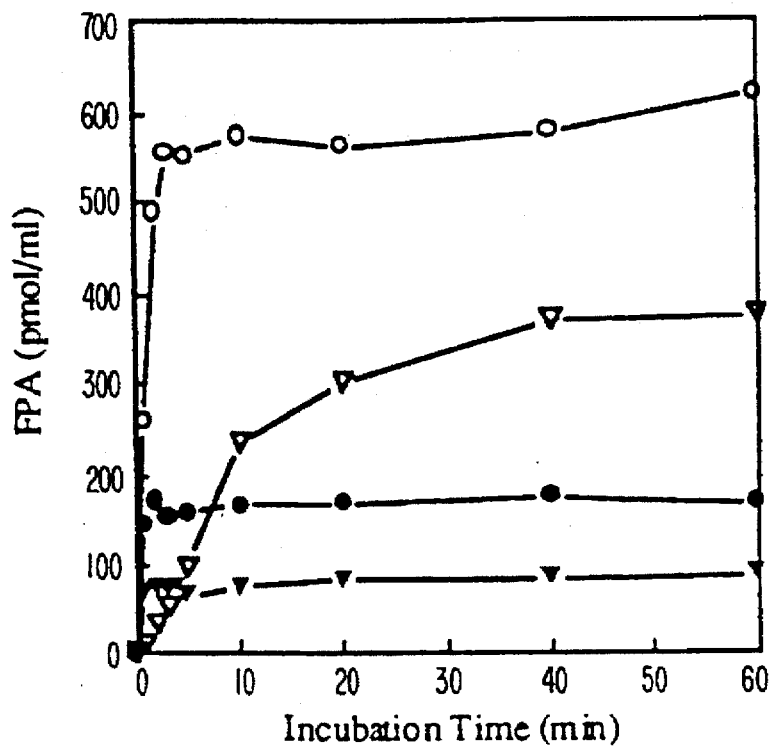
FIG. 5(A–B) depicts the comparative inhibitory effects of compound 8, Hirulog-1 and rHIR on fluid-phase (panel A) and clot-bound (panel B) a-thrombin-mediated FPA generation in citrated human plasma. The generation of FPA in the control (no inhibitor) group (o) was compared to compound 8 at a final concentration of 18.75 nM (1), Hirulog-1 at a final concentration of 500 nM (—) and rHIR at a final concentration of 4 nM(t).

FIG. 5A shows the effect of compound 8, Hirulog-1 and rHIR on the fluid-phase a-thrombin-mediated FPA generation in citrated human plasma. In this figure, the control (no inhibitor) group (o) was compared to compound 8 at a final concentration of 18.75 nM (1), Hirulog-1 at a final concentration of 500 nM (–) and rHIR at a final concentration of 4 nM(t).

As indicated in FIG. 5A, all three inhibitors block thrombin-mediated FPA release. However, compound 8 and rHIR produce stable inhibition of FPA generation throughout the incubation period. In contrast, Hirulog-1 (compound 25) produces only transient inhibition of thrombin-induced FPA generation. These findings are consistent with the data shown above in Example B for in vitro fibrin formation and further supports the concept that once Hirulog-1 undergoes proteolytic degradation within the Hirulog-1-thrombin complex, it can no longer fully inhibit thrombin activity.

2. Inhibition of Clot-Bound Thrombin.

Plasma clots were formed around wire hooks by the addition of CaCl$_2$ (final concentration, 25 mM) to 500 µl aliquots of citrated plasma. After aging the clots for 60 minutes at 37° C. with constant agitation, the clots were washed 10 times with 2 ml aliquots of 0.1M NaCl buffered with 0.05M Tris-HCL, pH 7.4 over an 18 hour period. The washed clots were then incubated in 1 ml aliquots of citrated plasma for 60 minutes at 37° C. in the absence or presence of the various inhibitors. At timed intervals, 100 µl aliquots were removed and the reaction was terminated by the addition of the irreversible serine protease inhibitor, D-phenylalanyl-prolinyl-argininyl-CH$_2$Cl.

Unreacted fibrinogen was precipitated with ethanol, and the ethanol supernatants were then assayed for FPA.

Figure 5B:
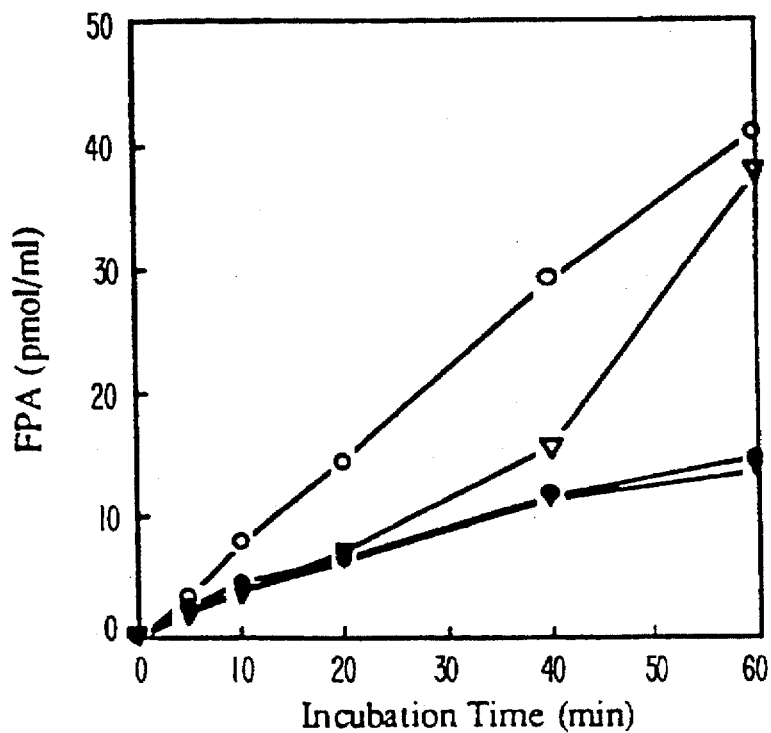

FIG. 5B shows the effect of compound 8, Hirulog-1 and rHIR on the clot-bound a-thrombin-mediated FPA generation in citrated human plasma. In this figure, the control (no inhibitor) group (o) was compared to compound 8 at a final concentration of 18.75 nM (1), Hirulog-1 at a final concentration of 500nM (–) and rHIR at a final concentration of 4 nM(t).

As previously demonstrated by Weitz, J. I. et.al. J. Clin. Invest., 86: 385–391 (1990) and shown in FIG. 5B, the incubation of a washed plasma clot in citrated plasma results in progressive, time-dependent FPA generation. Both compound 8 and rHIR were shown to stably inhibit clot-induced FPA generation. In contrast, Hirulog-1 only transiently inhibited FPA generation produced by the clot even at a ~27-fold molar excess over the concentration of compound 8 (FIG. 5, panels A and B).

Figure 6:
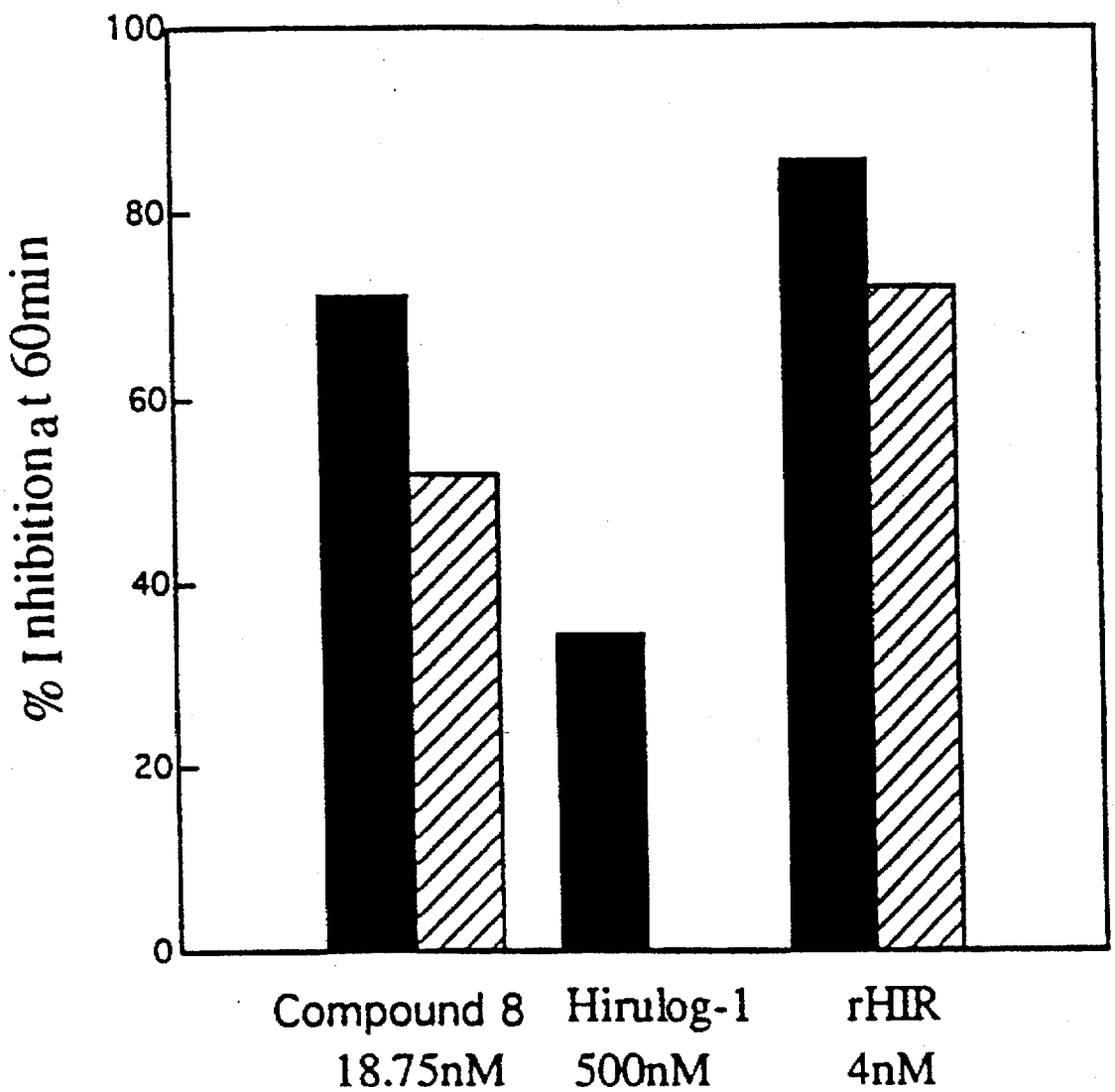
FIG. 6 depicts the comparative inhibitory effects of compound 8, Hirulog-1 and rHIR on fluid-phase (▪) and clot-bound (▨) a-thrombin-mediated FPA generation in citrated human plasma following a 60 minute incubation period.

Based on the data illustrated in FIGS. 5A and 5B, the inhibitory effects of the thrombin inhibitors against fluid-phase and clot-bound thrombin were compared based on the percent inhibition of free thrombin and clot-induced FPA generation produced by each inhibitor at 60 minutes incubation. FIG. 6 depicts the comparative inhibitory effects of compound 8, Hirulog-1 and rHIR on fluid-phase (■) and clot-bound (▨) a-thrombin-mediated FPA generation in citrated human plasma following a 60 minute incubation period. As illustrated in this figure, compound 8 and rHIR produce similar inhibition of both fluid-phase and clot-bound thrombin activity. In contrast, Hirulog-1 at a ~27-fold molar excess over compound 8 had less inhibitory activity against clot-bound thrombin than it does against the free, fluid-phase enzyme following this incubation period.

The results presented above clearly demonstrate that compound 8 can access and inhibit thrombin activity both free in plasma and more importantly bound to a fibrin-rich clot. The inhibitory profile of compound 8 is similar to that of rHIR in that the inhibition of these two pools of thrombin activity were stable for the 60 minute incubation period. This was in sharp contrast to Hirulog-1 which only showed transient inhibitory activity even at significantly higher molar concentrations.

Example G

Experimental Models of Thrombosis in Rabbits

The antithrombotic properties of compound 8 and Hirulog-1 (compound 25) were evaluated using the following established in vivo experimental rabbit models of acute thrombosis.

1. Rabbit Study of Venous Thrombus Growth.

To determine the duration of antithrombotic efficacy with Compound 8 following the termination of therapy, this inhibitor was compared to several other well-known antithrombotic agents in a rabbit model of venous thrombus growth described by Levi, M.et al., J. Thrombosis Haemostas., 66: 218–221 (1991). In this model, a thrombin-induced clot is formed in the jugular vein of an anesthetized rabbit. Following the restoration of flow, the test compound is administered by intravenously bolus followed by infusion along with radiolabeled ($^{125}$I) autologous fibrinogen. The infusion of test compound is continued for 120 minutes. Following this time, the extent of fibrin accretion is determined by comparing the amount of radiolabel incorporated into the clot versus circulating in the peripheral blood. At this time, the infusion of the test compound is stopped and the experiment continued for another 60 minutes. At 180 minutes, the extent of fibrin accretion is determined for the contralateral vessel. The data is expressed as "%Thrombus Growth" which is defined as (radioactivity in thrombus/ radioactivity in blood)×100.

In this protocol, TAP(recombinant tick anticoagulant protein, a selective inhibitor of factor Xa described by Neeper, M. P. et. al., J. Biol. Chem. 265:17746–17752 (1990)); recombinant Hirudin (rHIR) (CGP 39393) supplied by Ciba-Geigy, Horsham, UK.; and Hirulog-1. were separately administered intravenously as an initial bolus (0.5 mg/kg) followed by a continuous infusion (0.5 μg/kg/min) for 120 minutes. Compound 8 was administered in two dosing regimens referred to as "Cmp8H" (1.0 mg/kg bolus +0.5 μg/kg/minute) and as "Cmp8M" (0.5mg/kg bolus +0.5μg/kg/minute). LMWH (low molecular weight heparin, Fraxiparin, Sanofi, Paris, France) was administered as an initial bolus of 40 anti-Xa U/mg followed by a 0.33 anti-Xa U/kg/min infusion.

Figure 7:
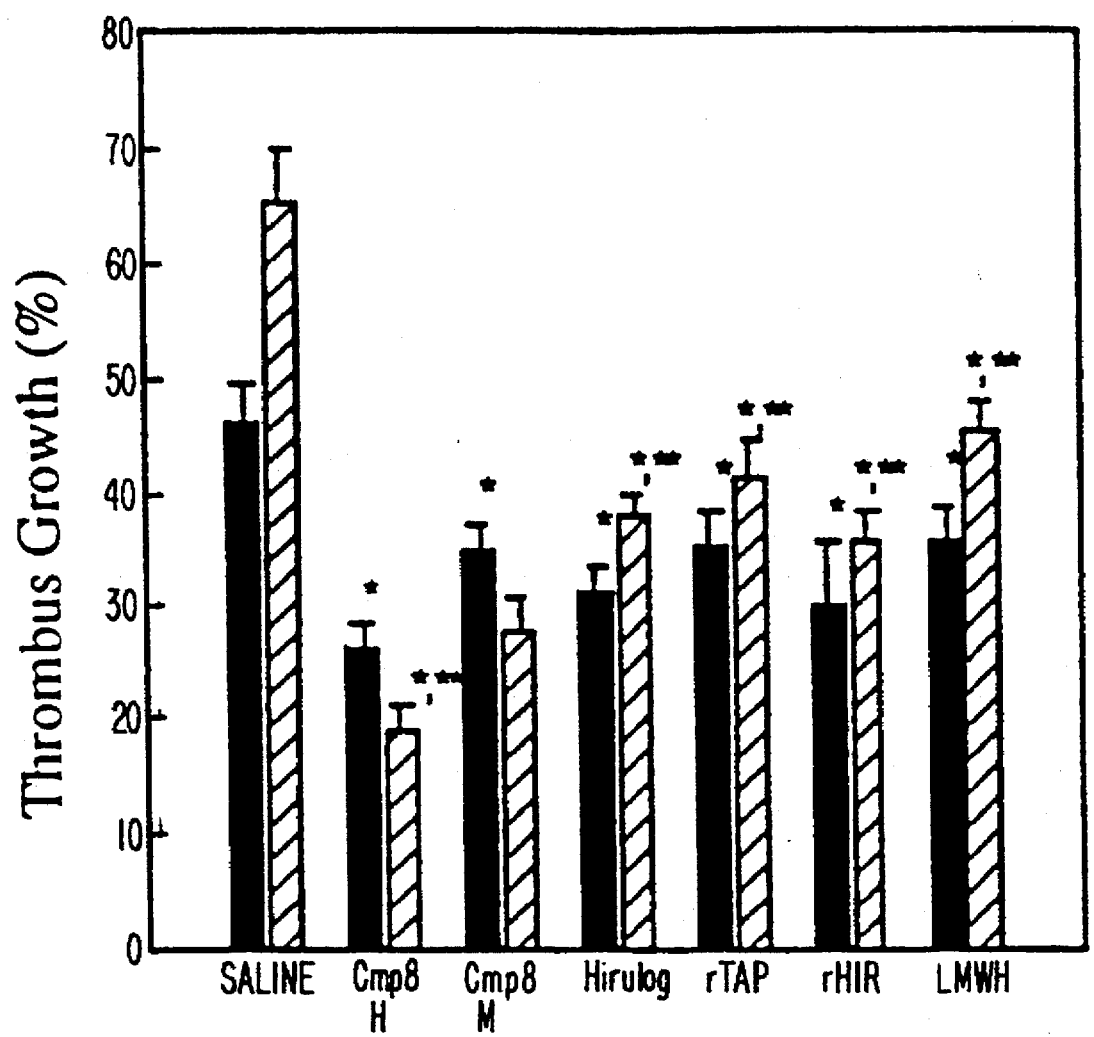
FIG. 7 depicts the comparative inhibitory effects of compound 8 and other antithrombotic agents in a rabbit model of venous fibrin growth. Thrombus growth was assesed following the 120 minutes infusion period (▪) and 60 minutes after the termination of the infusion at 180 minutes (▨). * p≤0.05 vs. time matched saline group, ** p≤0.001 versus time matched Compound 8-M group. Results are presented as the Mean±SEM.

FIG. 7 shows the comparative inhibitory effects of compound 8 and other antithrombotic agents in this rabbit model of venous fibrin growth. In this figure, thrombus growth was assessed following the 120 minute infusion period (▬) and 60 minutes after the termination of the infusion at 180 minutes (▨). "*" indicates a $p \leq 0.05$ vs. time matched saline group, "**" indicates a $p \leq 0.001$ versus time matched Compound 8-M group. Results are presented as the Mean±SEM.

The data in this figure clearly demonstrate a clear reduction in thrombus size following termination of the compound 8 infusion period compared to the other antithrombotic agents. The data suggest that compound 8 is stably inhibiting preformed, fibrin-bound thrombin associated with the clot which results in reduced fibrin accretion. In the face of ongoing fibrinolysis, a reduction in clot size was observed.

2. Rabbit jugular vein thrombosis/fibrinolysis model.

In this series of experiments, the effects of compound 8 on enhancing the extent of endogenous fibrinolysis was compared to that of rHIR.

New Zealand white rabbits of approximately 2.5 kg were anesthetized with 9 mg Ketamin (Aescoket, Boxtel, the Netherlands) and 0.5 ml Rompun 2% (Bayer, Leverkusen, Germany) I.M. To maintain anesthesia, repeated intramuscular injections of Ketamin were given when appropriate. The carotid artery and the jugular veins were exposed through a medial incision in the neck. The carotid artery was cleared and a cannula (Baby Feeding Tube, 1.6 mm f) was introduced for the administration of the study medication and blood sampling. The jugular veins were cleared over a distance of 2 cm and all side branches were ligated. The veins were clamped both proximally and distally.

Radiolabeled thrombi were produced in the jugular veins of the rabbit and the extent of fibrinolysis was determined by measuring the decrease in initial radioactivity of the preformed thrombi. Homologous rabbit blood was mixed with $^{125}$I-labeled fibrinogen (final radioactivity approximately 25 μCi per ml). An aliquot of 150 μl 1 of this mixture was then aspirated in a 1 ml syringe containing 25 μl thrombin (Human Thrombin T7009, Sigma Chemical Company, St. Louis, USA, 150 IU/ml) and 45 μl CaCl$_2$ (0.25M) and quickly injected into the isolated venous segment. After 30 minutes of aging, the clamps were removed and the infusion of study medication started. The extent of endogenous fibrinolysis was assessed by measuring the remaining radioactivity of the thrombus at the end of the study as compared with the initial radioactivity and was expressed as a percentage of the initial thrombus volume. Both compound 8 and rHIR were administered as described in the previous study as an initial bolus (0.5mg/kg bolus) followed by a continuous infusion for 120 min (0.5 μg/kg/min).

Figure 8:
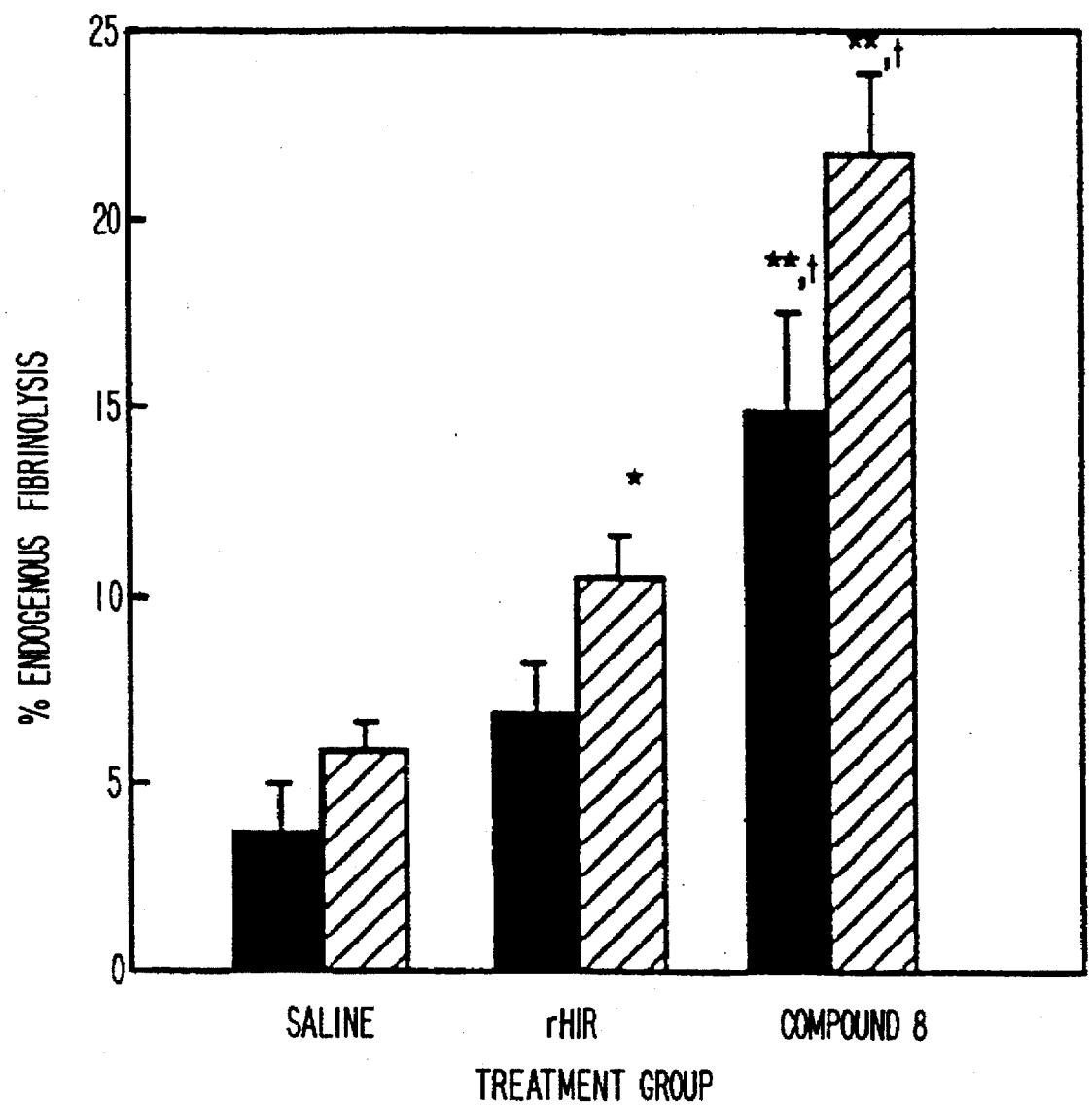
FIG. 8 depicts the effect of Compound 8 compared to rHIR on endogenous fibrinolysis of a preformed venous clot in a rabbit model of venous thrombosis. The extent of endogenous fibrinolysis was assessed following the 120 minutes infusion period (▪) and 60 minutes after the termination of the infusion at 180 min (▨). * p≤0.05 versus. time matched saline group, ** p≤0.001 versus time matched saline group, †p≤0.001 versus time matched rHIR group. Results are presented as the Mean±SEM.

FIG. 8 shows the effect of Compound 8 compared to rHIR on endogenous fibrinolysis of a preformed venous clot in a rabbit model of venous thrombosis. The extent of endogenous fibrinolysis was assessed following the 120 minutes infusion period (▬) and 60 minutes after the termination of the infusion at 180 min (▨). "*" indicates a $p \leq 0.05$ versus time matched saline group, "**" indicates a $p \leq 0.001$ versus time matched saline group, "t" indicates a $p \leq 0.001$ versus time matched rHIR group. Results are presented as the Mean±SEM.

The data illustrated in FIG. 8 show that compound 8 can induce a greater degree of endogenous fibrinolysis resulting in a reduced clot size when compared to rHIR at the doses used. These results may explain the difference between these two agents in the thrombus growth experiments presented above in the rabbit model with respect to the size of the clot at the 180 minute time point. The stable inhibition of venous clot extension resulting in a reduction in clot size seen in this model may have important clinical implications for the treatment of established deep vein thrombosis (DVT). It is known that in most DVT patients there is an overall reduction in clot size which occurs over the course of continuous anticoagulant therapy with heparin or Coumadin. Hirsh, J., N. Engl. J. Med., 324:1565–1574 (1991).

The potential of treating these patients for a short time with an agent such as compound 8 and obtaining long term antithrombotic efficacy resulting in a reduction in clot size could be a major advantage in reducing the period in which these patients are exposed to anticoagulant therapy.

Example H

Experimental Models of Thrombosis in Baboons

1. Evaluation of Compound 8 in a baboon model of arterial thrombosis.

The similarity of the coagulation responses between baboons and humans makes them an ideal experimental subject to study the effects of new antithrombotic agents on the thrombotic process. Harker, L. A. et al., Circulation, 83: Suppl IV IV-41–IV-55 (1991)). We therefore determined the the antithrombotic dose-duration response and corresponding hemostatic and hemorrhagic effects of compound 8 in a baboon model of heparin-resistant arterial thrombosis in a system which measures the formation of a platelet-rich thrombus on an exteriorized arterio-venous shunt as described by Harker, L. A. et al., Id.

The antithrombotic doses of compound 8 were initially established using small amounts of reagent by infusing the drug into the boundary layer of rapidly flowing blood immediately proximal to a highly thrombogenic segment of Dacron vascular graft incorporated into an exteriorized chronic femoral arteriovenous (AV) shunt using a fusion device. The antithrombotic dose-response of compound 8 was then evaluated for drug administered by continuous intravenous infusion while concurrently assessing the corresponding antihemostatic effects. Subsequently, the duration of compound 8 therapy required to produce lasting antithrombotic effects were determined for vascular graft thrombosis by infusing a large fully antithrombotic dose of compound 8 for progressively longer periods of time, and following the accumulation of thrombus thereafter.

a. Dose-response studies using the boundary layer infusion device.

Initially, the dose-response between blood levels of compound 8 and the interruption of platelet-rich arterial type thrombus formation on highly thrombogenic segments of Dacron vascular graft interposed in exteriorized chronic femoral AV shunts was determined in a group of 4–5 animals using a proximal boundary layer infusion device. Drug was infused circumferentially through the pores of Goretex graft into the boundary layer interfacing blood flowing at 100 ml/min and the thrombogenic surface of 2 cm-long segments of Dacron vascular graft placed immediately distal to the infusion device (see below). The studies were begun by infusing 0.1 ml/min of 500 nM compound 8 to achieve boundary layer concentrations of 100 nM at the thrombogenic segment interface. Appropriate iteration of dosing established the concentration of drug required to reduce thrombus formation by half ($IC_{50}$). With this approach the concentration of drug required to produce antithrombotic effects in vivo were established using less than 1/100 the amount of drug needed if systemic administration of the drug was employed. This approach minimizes the amount of drug needed for preliminary dose response and obviates possible toxicities.

b. Systemic antithrombotic and antihemostatic comparison for Compound 8.

A high-flow device which simulates arterial-type blood flow that generally exceeds 200 ml/min (shear rates of about 600–700 $sec^{-1}$) was used to evaluate the antithrombotic effects of compound 8. Platelet-rich thrombus formation was induced by three different thrombogenic segments inserted as extension pieces into chronic arteriovenous (AV) access shunts in baboons as described by Kelly A. B. et al. in Blood, 77: 1006–1012 (1991) and Proc. Natl. Acad. Sci. USA, 89:6040–6044 (1992). Systemic administration is needed in order to coincidentally evaluate both antithrombotic benefits and hemostatic safety. Hemostatic function was also evaluated, including the template bleeding time to assess platelet hemostatic function, and the standard coagulation tests.

The thrombogenic surface used in this study was a Dacron vascular graft as described by Kelly A. B. et al.,Id., incorporated into the exteriorized shunt. This thrombogenic surface was selected for study because it induces thrombus that is thrombin-mediated and platelet-dependent as well as highly reproducible and resistant to both aspirin and heparin in a clinically relevant manner. Based on the results in the boundary layer device (used to determine appropriate doses), compound 8 was continuously infused intravenously at rates required to produce high, intermediate and low antithrombotic effects.

Figure 9:
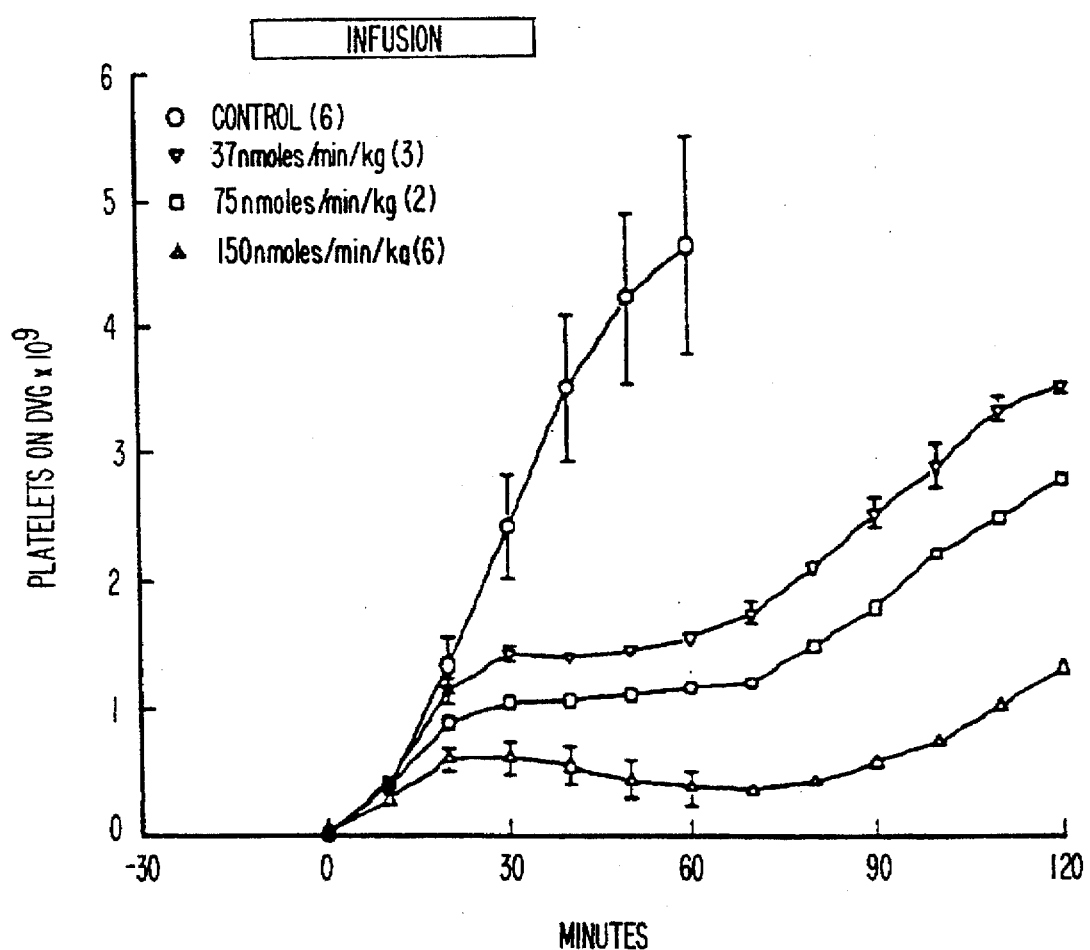
FIG. 9 depicts the effect of compound 8 following systemic administration to conscious baboons on platelet deposition in the dacron vascular graft segment. The results are presented as the Mean±SD with the corresponding replicates shown next to the treatment group in the figure.

FIG. 9 shows the effect of compound 8 following systemic administration (infusion) over a 60 minute period to a conscious baboon on platelet deposition in the dacron vascular graft segment. The results are presented as the Mean±SD with the corresponding replicates shown next to the treatment group in the figure. The control group(m) had 6 replicates, the group administered with 37 nmoles/minute/kg (−) had 3 replicates, the group administered with 75 nmoles/minute/kg (o) had 2 replicates and the group administered with 150 nmoles/minute/kg (Δ) had 6 replicates. The various hemostatic parameters were also determined as shown in Table V.

TABLE V

Effects of Compound 8 on Blood markers of Thrombosis.

| Parameter | Control | Treatment Group | | |
|---|---|---|---|---|
| | | 37 nmol/kg/min | 75 nmol/kg/min | 150 nmol/kg/min |
| Platelet deposition ($\times 10^9$) | 4.65 ± 0.85 | 1.57 ± 0.03 | 1.17 ± 0.03 | 0.39 ± 0.14 |
| Compound 8 levels (μg/mL) | 0 | 13.5 ± 1.2 | 23.5 ± 7.8 | 62.8 ± 14.2 |
| Forearm | 4.5 ± 0 | 4 ± 0 | 9.8 ± 3.9 | 10.9 ± 3.1 |

TABLE V-continued

Effects of Compound 8 on Blood markers of Thrombosis.

| Parameter | Control | Treatment Group | | |
|---|---|---|---|---|
| | | 37 nmol/kg/min | 75 nmol/kg/min | 150 nmol/kg/min |
| Bleeding Time (min) Fibrinogen (mg/mL) | 2.62 ± 0.35 | 2.41 ± 0.45 | 2.45 ± 0.45 | 3.16 ± 0.78 |
| APTT (sec) | 33 ± 1 | >300 | >300 | >300 |
| Platelet Count ($\times 10^3$) | 432 ± 28 | 428 ± 35 | 420 ± 0 | 415 ± 56 |
| PF-4[a] (ng/mL) | | | | |
| Pre-dosing | 2.7 ± 1.5 | 2.6 | 2.8 | 1.3 |
| 60 min | 58.4 ± 13.3 | 1.5 | 1.9 | 1.0 |
| bTG[a] (ng/mL) | | | | |
| Pre-dosing | 2.5 ± 2.9 | 2.1 | 2.6 | 2.1 |
| 60 min | 45.7 ± 19.3 | 1.7 | 1.3 | 0.5 |
| FPA[a] (nM) | | | | |
| Pre-dosing | 3.5 ± 1.1 | 3.0 ± 0.9 | 3.3 ± 1.7 | 1.7 |
| 60 min | 26.8 ± 17.1 | 1.45 ± 0.6 | 0.75 ± 0.07 | 0.7 ± 0.4 |
| TAT[a] (ng/mL) | | | | |
| Pre-dosing | 7.5 ± 2.9 | 5.9 ± 2.2 | 6.5 ± 2.2 | 8.4 ± 4.2 |
| 60 min | 53.3 ± 26 | 2.6 ± 0.5 | 2.2 ± 1.3 | 2.0 ± 0.8 |

[a]PF-4 refers to platelet factor 4; bTG refers to b-thromboglobulin; FPA refers to fibrinopeptide A; and TAT refers to thrombin-antithrombin complexes.

Interestingly as seen in Table V, there was no increase in forearm template bleeding time associated with the $ED_{50}$ dose of compound 8 compared to a control time of 4 minutes. $ED_{50}$ refers to the dose which gives a 50% inhibition of platelet deposition.

The observed data is in stark contrast to several other antithrombin-III independent antithrombin agents which have been evaluated in this model, including recombinant hirudin described by Kelly A B et al., Blood, 77: 1006–1012 (1991)); the irreversible antithrombin peptide, D-phenylalanyl-L-prolyl-L-arginyl chloromethylketone (D-FPR-CMK) described by Hanson S. R. and Harker L. A., Proc Natl Acad Sci., 85:3184–3188, (1988); the competitive antithrombin peptide,. D-phenylalanyl-prolinyl-boroarginine, (D-FPboroR); the bifunctional antithrombin peptide, Hirulog-1; the carboxy-terminal dodecapeptide of hirudin as described by Kelly AB et al., Proc. Natl. Acad. Sci. USA, 89: 6040–6044 (1992); and arginine-based (argatroban) synthetic direct antithrombins as described by Harker L. A. et al., "Novel antithrombotic agents", Hemostasis and Thrombosis: Basic Principles and Clinical Practice, 3rd Ed. Philadelphia, J. P. Lippincott (Edits. Colman R. W. et al. 1992). All of these direct antithrombins interrupt platelet and fibrin deposition and thrombotic occlusion in a dose-dependent manner that is complete at the highest doses for all thrombogenic surfaces tested as shown in Table VI.

TABLE VI

Comparative Antithrombotic Effects of Compound 8 to Other Direct Antithrombins.

| Agent | Antithrombotic Effects | Antihemostatic Effects | |
|---|---|---|---|
| | $ED_{50}$ (nmol/kg/min) | Bleeding Time (min) | APTT (sec) |
| Control | — | 4 | 32 |
| Compound 8 | 35 | 4 | >300 |
| Hirulog-1 | 125 | 21 | >300 |
| r-Hirudin | 5 | 12 | 130 |
| Argatroban | >800 | >30 | >300 |
| dF-P-R-al | 250 | 14 | 145 |
| dF-P-boroR | 25 | 12 | 95 |
| dF-P-R-CMK | 25 | 12 | 95 |

$ED_{50}$-Dose which gives a 50% inhibition of platelet deposition c. Duration of Compound 8 therapy for lasting antithrombotic effects.

To assess the duration of the antithrombotic effect of compound 8 following a limited infusion period, compound 8 was infused intravenously at the highest, fully antithrombotic systemic dose (as determined above) for 3 hours in animals bearing 4 segments of Dacron vascular graft in exteriorized chronic AV femoral shunts. Thrombus formation was assessed by gamma camera imaging. After discontinuing the infusion, subsequent accumulation of thrombus on the segments was measured for 2 of the segments throughout the following 3 hours, and again at 24 hours. The other 2 segments were transferred to the shunts of labeled shunt-bearing recipient animals to exclude the possibility that the thrombogenic response of blood was altered by the prior experimental procedures.

Figure 10:
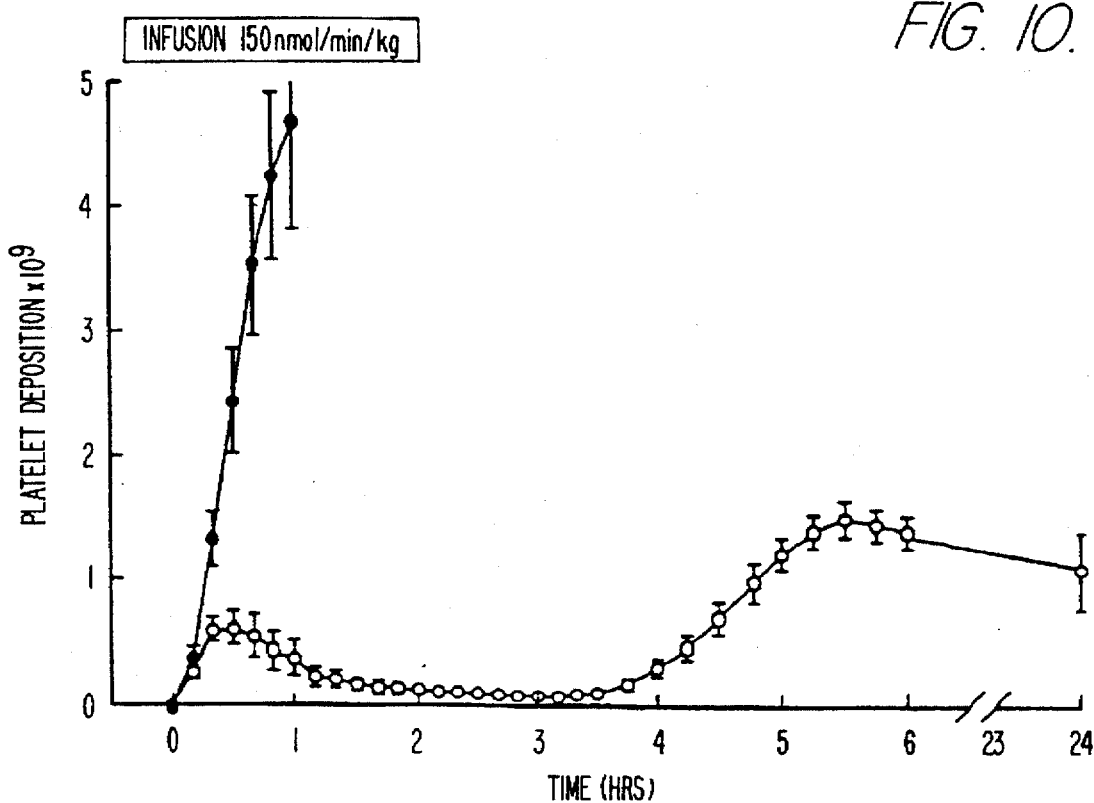
FIG. 10 depicts the effect of a limited (3 hours), high-dose infusion of compound 8 (m) compared to saline (1)on 24 hour platelet deposition and patency. The results are presented as the Mean±SD (n=6).
Figure 11:
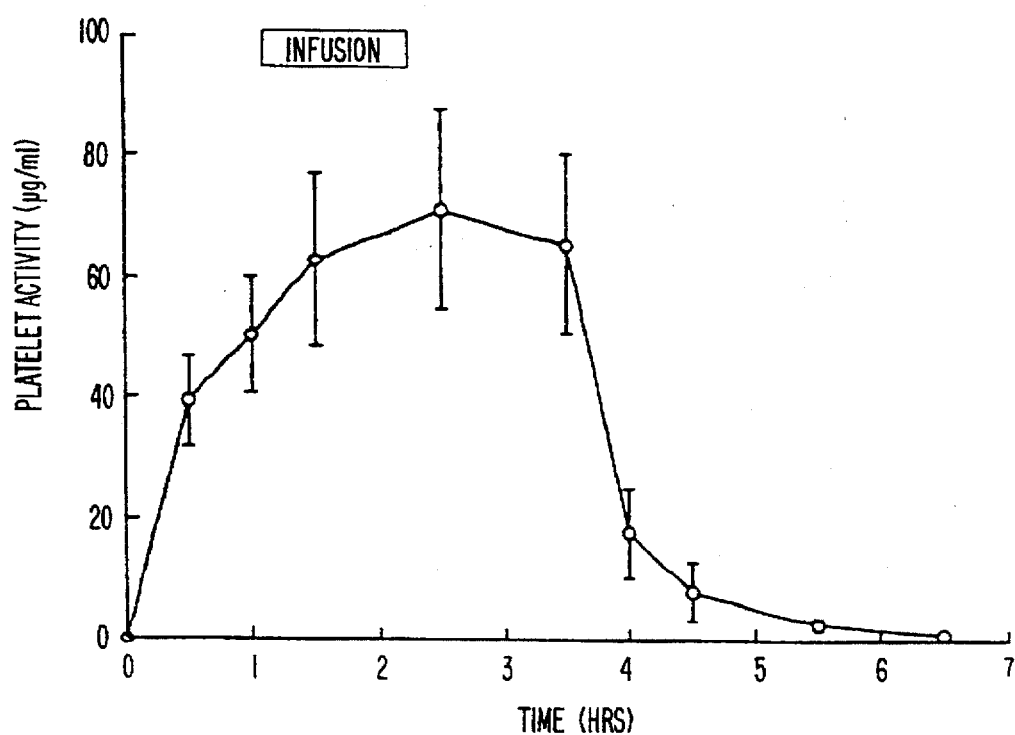
FIG. 11 depicts the plasma levels of compound 8 corresponding to the treatment groups shown in FIG. 10. The results are presented as the Mean±SD (n=6).

FIG. 10 illustrates the results from a limited duration, high dose systemic infusion of compound 8 with the corresponding plasma levels shown in FIG. 11. The infusion was over 3 hour period at a rate of 150 nmole/min/kg. In FIG. 10, the effect of this high-dose infusion of compound 8 (m) and of saline (l) on 24 hour platelet deposition and patency is shown. The results are presented as the Mean±SD (n=6). FIG. 11 illustrates the plasma levels of compound 8 corresponding to the treatment groups shown in FIG. 10 for the 3 hour infusion period. The results are presented as the Mean±SD (n=6).

These data demonstrate that a limited (3 hours) high dose infusion of compound 8 results in an inhibition of platelet deposition for the duration of the experiment which was 24 hours. In addition, the graft segments remained patent with no reduction in blood flow.

The results from this animal model demonstrate a dose-dependent reduction in platelet thrombus formation with a favorable antihemostatic profile compared to other antithrombin agents investigated in the same setting. The high degree of similarity between the baboon and human hemostatic systems suggests that similar antithrombotic efficacy in humans would be expected with this compound as well.

We claim:

1. A compound having the formula:

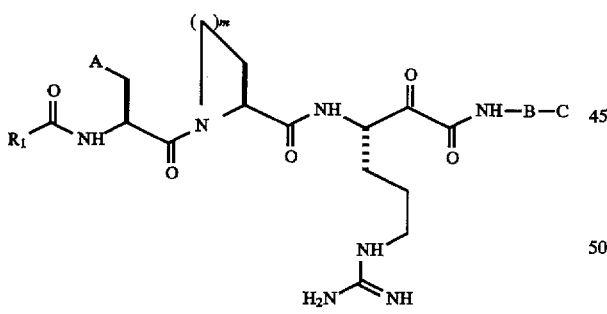

wherein $R_1$ is alkyl of 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of 1 to about 12 carbon atoms, alkenyloxy of about 3 to about 8 carbon atoms, aryloxy of about 6 to about 14 carbon atoms, or aralkyloxy of about 6 to about 15 carbon atoms;

A is selected from the group consisting of

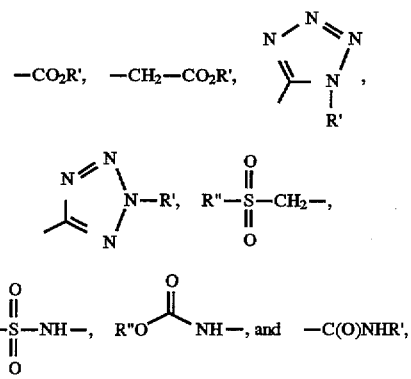

wherein R' is H, alkyl of 1 to about 6 carbon atoms, or aralkyl of about 6 to about 15 carbon atoms and R" is alkyl of 1 to about 6 carbon atoms or alkyl of about 6 to about 15 carbon atoms;

m is 1, 2 or 3;

B is selected from the group consisting of -Gly-Gly-Gly-Gly-Gly-Asn-Gly-Asp-Phe-, and -Gly-Gly-Gly-Gly-Gly-Arg-Gly-Asp-Phe-;

C is selected from the group consisting of -Glu-Glu-Ile-Pro-Glu-Tyr-Leu-OH, -Glu-Glu-Ile-Pro-Glu-Glu-Tyr-Leu-OH, -Glu-Glu-Ile-Pro-Glu-Tyr(3-iodo)-Leu-OH, -Glu-Glu-Ile-Pro-Glu-Tyr(3,5-diiodo)-Leu-OH, -Glu-Glu-Ile-Pro-Glu-Glu-Tyr(3-iodo)-Leu-OH, -Glu-Glu- Ile-Pro-Glu-Glu-Tyr(3,5-diiodo)-Leu-OH, -Glu-Glu-Ile-Pro-Glu-Tyr-Leu-NH$_2$, -Glu-Glu-Ile-Pro-Glu-Glu-Tyr-Leu-NH$_2$, -Glu-Glu-Ile-Pro-Glu-Tyr(3-iodo)-Leu-NH$_2$, -Glu-Glu-Ile-Pro-Glu-Tyr(3,5-diiodo)-Leu-NH$_2$, -Glu-Glu-Ile-Pro-Glu-Glu-Tyr(3-iodo)-Leu-NH$_2$, and -Glu-Glu-Ile-Pro-Glu-Glu-Tyr(3,5-diiodo)-Leu-NH$_2$; or pharmaceutically acceptable salt thereof.

2. A compound of claim 1, wherein m is 2.

3. A compound of claim 2 wherein B is -Gly-Gly-Gly-Gly-Gly-Asn-Gly-Asp-Phe- and C is -Glu-Glu-Ile-Pro-Glu-Tyr-Leu-OH.

4. A compound of claim 2 wherein B is -Gly-Gly-Gly-Gly-Gly-Asn-Gly-Asp-Phe- and C is -Glu-Glu-Ile-Pro-Glu-Glu-Tyr-Leu-OH.

5. A compound of claim 2 wherein B is -Gly-Gly-Gly-Gly-Gly-Arg-Gly-Asp-Phe- and C is -Glu-Glu-Ile-Pro-Glu-Tyr-Leu-OH.

6. A compound of claim 2 wherein B is -Gly-Gly-Gly-Gly-Gly-Arg-Gly-Asp-Phe- and C is -Glu-Glu-Ile-Pro-Glu-Glu-Tyr-Leu-OH.

7. A compound of claim 3, 4, 5 or 6, wherein $R_1$ is alkyl of 1 to about 10 carbon atoms or aralkyl of about 7 to about 12 carbon atoms.

8. A compound of claim 7, wherein $R_1$ is selected from the group consisting of cyclohexyl, 4-heptyl, 3-methylpentyl, 2-methylpropyl, 3-octyl and 2-phenylethyl.

9. A compound of claim 8, wherein $R_1$ is 4-heptyl.

10. A compound of claim 9, wherein A is selected from the group consisting of

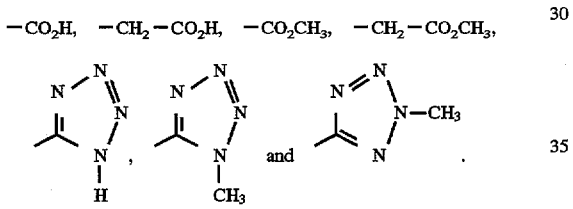

11. A compound of claim 1 having the formula:

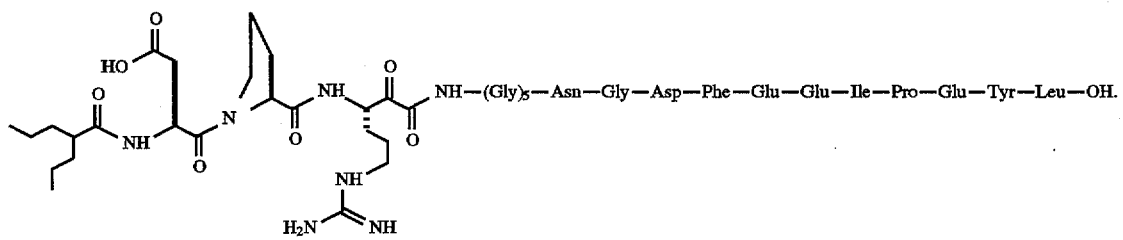

[1]

12. A compound of claim 1 having the formula:

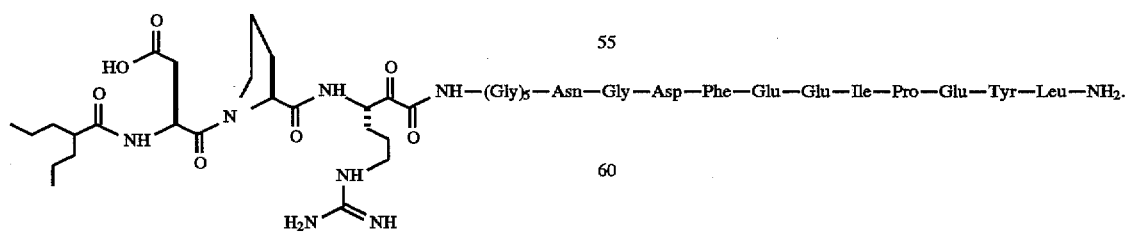

[41]

13. A compound of claim 1 having the formula:
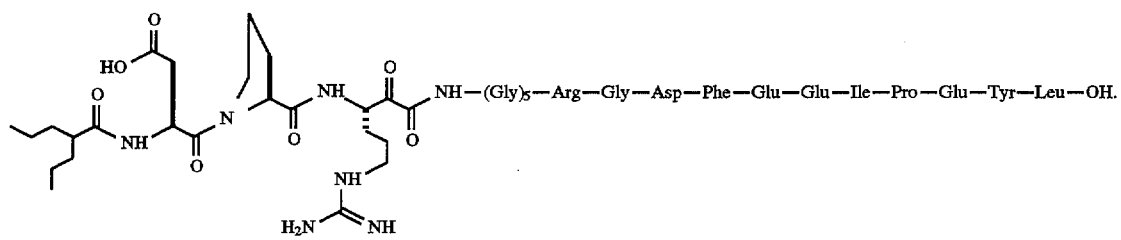
[11]
14. A compound of claim 1 having the formula:
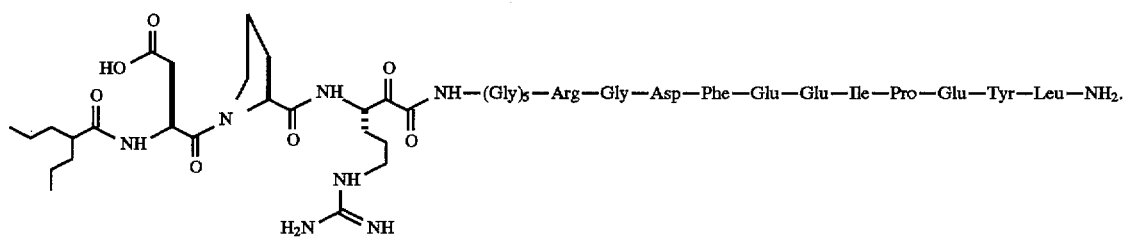
[42]
15. A compound of claim 1 having the formula:
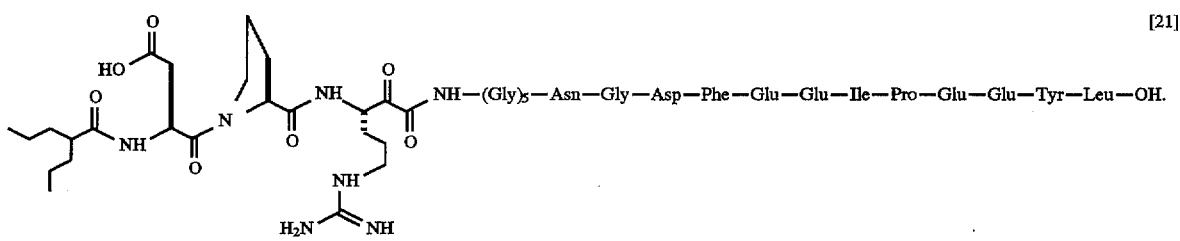
[21]
16. A compound of claim 1 having the formula:
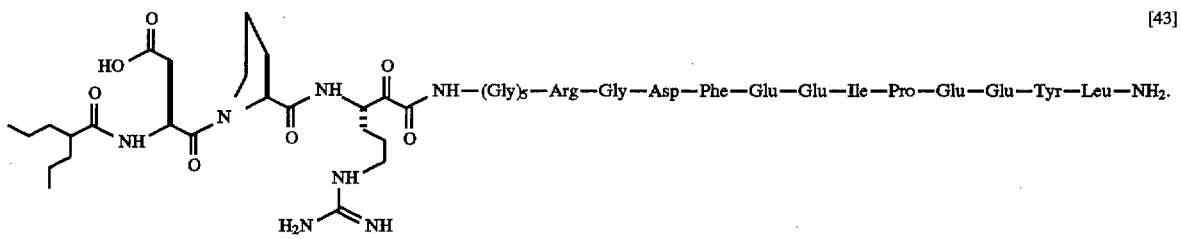
[43]
17. A compound of claim 1 having the formula:
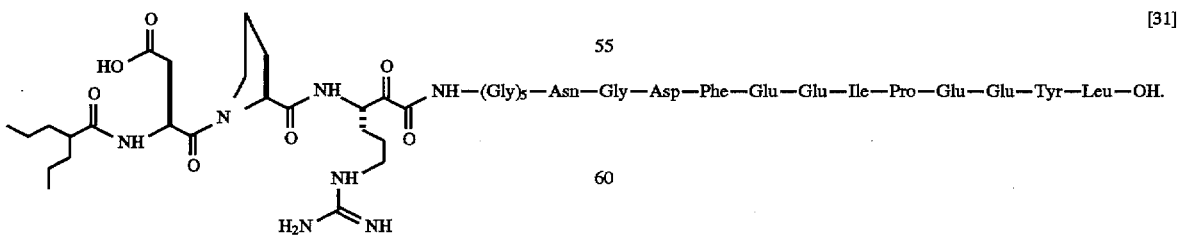
[31]

18. A compound of claim 1 having the formula:

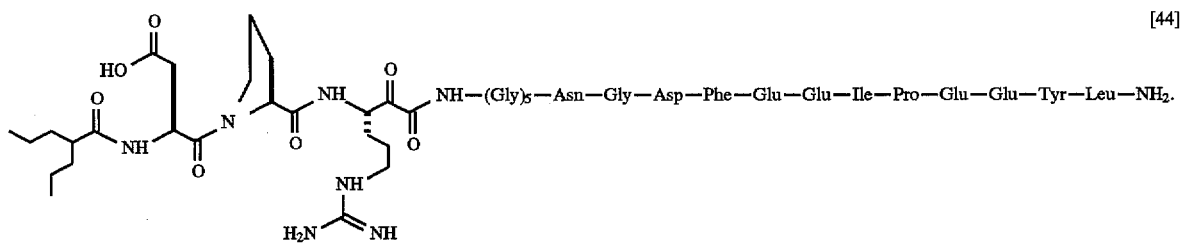

[44]

19. A compound of claim 2, wherein C is selected from the group consisting of -Glu-Glu-Ile-Pro-Glu-Tyr(3-iodo)-Leu-OH, -Glu-Glu-Ile-Pro-Glu-Tyr(3,5-diiodo)-Leu-OH, -Glu-Glu-Ile-Pro-Glu-Glu-Tyr(3-iodo)-Leu-OH, -Glu-Glu-Ile-Pro-Glu-Glu-Tyr(3,5-diiodo)-Leu-OH, -Glu-Glu-Ile-pro-Glu-Tyr(3-iodo)-Leu-$NH_2$, -Glu-Glu-Ile-Pro-Glu-Tyr (3,5-diiodo)-Leu-$NH_2$, -Glu-Glu-Ile-Pro-Glu-Glu-Tyr(3-iodo)-Leu-$NH_2$, and -Glu-Glu-Ile-Pro-Glu-Glu-Tyr(3,5-diiodo)-Leu-$NH_2$.

20. A compound of claim 19 wherein B is -Gly-Gly-Gly-Gly-Gly-Asn-Gly-Asp-Phe- and C is selected from the group consisting of -Glu-Glu-Ile-Pro-Glu-Tyr(3-iodo)-Leu-OH and -Glu-Glu-Ile-Pro-Glu-Tyr(3,5-diiodo)-Leu-OH.

21. A compound of claim 19 wherein B is -Gly-Gly-Gly-Gly-Gly-Asn-Gly-Asp-Phe- and C is selected from the group consisting of -Glu-Glu-Ile-Pro-Glu-Glu-Tyr(3-iodo)-Leu-OH and -Glu-Glu-Ile-Pro-Glu-Glu-Tyr(3,5-diiodo)-Leu-OH.

22. A compound of claim 19 wherein B is -Gly-Gly-Gly-Gly-Gly-Arg-Gly-Asp-Phe- and C is selected from the group consisting of -Glu-Glu-Ile-Pro-Glu-Tyr(3-iodo)-Leu-OH and-Glu-Glu-Ile-Pro-Glu-Tyr (3,5-diiodo) -Leu-OH.

23. A compound of claim 19 wherein B is -Gly-Gly-Gly-Gly-Gly-Arg-Gly-Asp-Phe- and C is selected from the group consisting of -Glu-Glu-Ile-Pro-Glu-Glu-Tyr(3-iodo)-Leu-OH and-Glu-Glu-Ile-Pro-Glu-Glu-Tyr(3,5-diiodo) -Leu-OH.

24. A compound of claim 19, 20, 21, 22 or 23, wherein $R_1$ is alkyl of about 1 to about 10 carbon atoms or aralkyl of about 7 to about 12 carbon atoms.

25. A compound of claim 24, wherein $R_1$ is selected from the group consisting of cyclohexyl, 4-heptyl, 3-methylpentyl, 2-methylpropyl, 3-octyl and 2-phenylethyl.

26. A compound of claim 25, wherein $R_1$ is 4-heptyl.

27. A compound of claim 26, wherein A is selected from the group consisting of

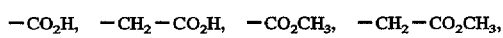

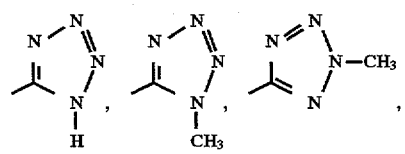

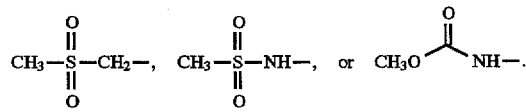

28. A compound of claim 27, wherein A is —$CO_2H$.

29. A compound of claim 19, 20, 21, 22 or 23, wherein all iodine atoms are together selected from the group consisting of I-123, I-125 and I-131.

30. A compound of claim 29, wherein $R_1$ is alkyl of about 1 to about 10 carbon atoms or aralkyl of about to about 12 carbon atoms.

31. A compound of claim 30, wherein $R_1$ is selected from the group consisting of cyclohexyl, 4-heptyl, 3-methylpentyl, 2-methylpropyl, 3-octyl and 2-phenylethyl.

32. A compound of claim 31, wherein $R_1$ is 4-heptyl.

33. A compound of claim 32, wherein A is selected from the group consisting of —$CO_2H$, —$CH_2$—$CO_2H$, —$CO_2CH3$ and —$CH_2$—$CO_2CH_3$.

34. A compound of claim 33, wherein A is —$CO_2H$.

35. A compound having the formula:

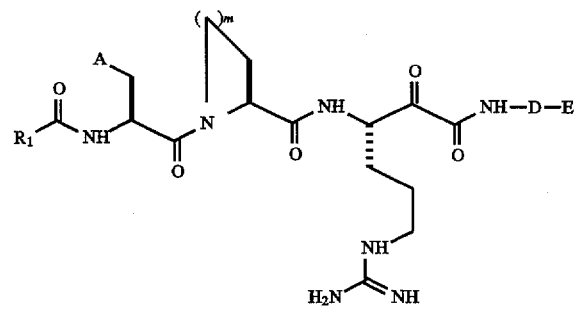

wherein $R^1$ is alkyl of 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of 1 to about 12 carbon atoms, alkenyloxy of about 3 to about 8 carbon atoms, aryloxy of about 6 to about 14 carbon atoms, or aralkyloxy of about 6 to about 15 carbon atoms;

A is selected from the group consisting of

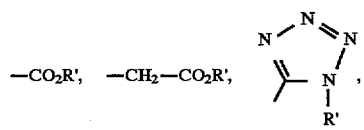

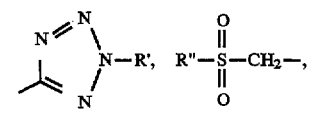

-continued

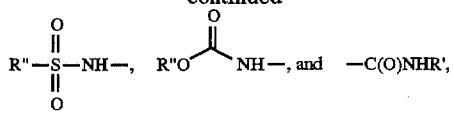

wherein R' is H, alkyl of 1 to about 6 carbon atoms, or aralkyl of about 6 to about 15 carbon atoms and R" is alkyl of 1 to 6 carbon atoms or aralkyl of about 6 to about 15 carbon atoms;

m is 1, 2 or 3;

D is selected from the group consisting of -X-Gly-Gly-Gly-Gly-Asn-Gly-Asp-Phe-, -Gly-X-Gly-Gly-Gly-Asn-Gly-Asp-Phe-, -Gly-Gly-X-Gly-Gly-Asn-Gly-Asp-Phe-, -Gly-Gly-Gly-X-Gly-Asn-Gly-Asp-Phe-, -Gly-Gly-Gly-Gly-X-Asn-Gly-Asp-Phe-, -X-Gly-Gly-Gly-Gly-Arg-Gly-Asp-Phe-, -Gly-X-Gly-Gly-Gly-Arg-Gly-Asp-Phe-, -Gly-Gly-X-Gly-Gly-Arg-Gly-Asp-Phe-, -Gly-Gly-Gly-X-Gly-Arg-Gly-Asp-Phe-, -Gly-Gly-Gly-Gly-X-Arg-Gly-Asp-Phe-, and -Gly-Gly-Gly-Gly-Gly-X-Gly-Asp-Phe-, wherein X has the formula:

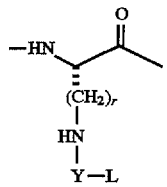

wherein R is an integer selected from R to 6, L is a chelating means for chelating a radioactive or paramagnetic atom, and Y is an attaching means for attaching chelating means to the amino group;

E is selected from the group consisting of -Glu-Glu-Ile-Pro-Glu-Tyr-Leu-OH, -Glu-Glu-Ile-Pro-Glu-Glu-Tyr-Leu-OH, -Glu-Glu-Ile-Pro-Glu-Tyr(3-iodo)-Leu-OH, -Glu-Glu-Ile-Pro-Glu-Tyr(3,5-diiodo)-Leu-OH, -Glu-Glu-Ile-Pro-Glu-Glu-Tyr(3-iodo)-Leu-OH, -Glu-Glu-Ile-Pro-Glu-Glu-Tyr(3,5-diiodo)-Leu-OH, -Glu-Glu-Ile-Pro-Glu-Tyr-Leu-NH$_2$, -Glu-Glu-Ile-Pro-Glu-Glu-Tyr-Leu-NH$_R$, -Glu-Glu-Ile-Pro-Glu-Tyr(3-iodo)-Leu-NH$_2$, -Glu-Glu-Ile-Pro-Glu-Tyr(3,5-diiodo)-Leu-NH$_2$, -Glu-Glu-Ile-Pro-Glu-Glu-Tyr(3-iodo)-Leu-NH$_2$, and -Glu-Glu-Ile-Pro-Glu-Glu-Tyr(3,5-diiodo)-Leu-NH$_2$;

or pharmaceutically acceptable salt thereof.

36. A compound of claim 35, wherein m is 2.

37. A compound of claim 36, wherein E is selected from the group consisting of -Glu-Glu-Ile-Pro-Glu-Tyr-Leu-OH and -Glu-Glu-Ile-Pro-Glu-Glu-Tyr-Leu-OH.

38. A compound of claim 37, wherein D is selected from the group consisting of -Gly-Gly-X-Gly-Gly-Asn-Gly-Asp-Phe-, -Gly-Gly-X-Gly-Gly-Arg-Gly-Asp-Phe- and -Gly-Gly-Gly-Gly-X-Gly-Asp-Phe-.

39. A compound of claim 38, wherein Y has the formula and —C(=S)— and L is 1-(p-aminobenzyl)diethylenetriaminepentaacetic acid.

40. A compound of claim 39, wherein R$_1$ is alkyl of 1 to about 10 carbon atoms or aralkyl of about 7 to about 12 carbon atoms.

41. A compound of claim 40, wherein R$_1$ is selected from the group consisting of cyclohexyl, 4-heptyl, 3-methylpentyl, 2-methylpropyl, 3-octyl and 2-phenylethyl.

42. A compound of claim 41, wherein R$_1$ is 4-heptyl.

43. A compound of claim 42, wherein A is selected from the group consisting of

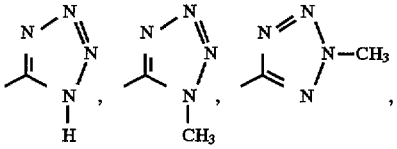

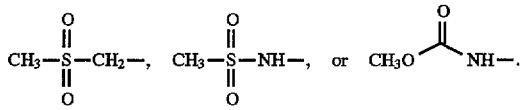

44. A compound of claim 43, where A is —CO$_2$H.

45. A compound of claim 38, wherein Y has the formula

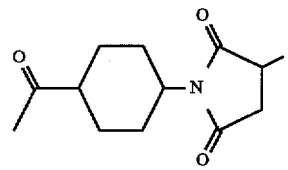

and L is metallothionein.

46. A compound of claim 45, wherein R$_1$ is alkyl of 1 to about 10 carbon atoms or aralkyl of about 7 to about 12 carbon atoms.

47. A compound of claim 46, wherein R$_1$ is selected from the group consisting of cyclohexyl, 4-heptyl, 3-methylpentyl, 2-methylpropyl, 3-octyl and 2-phenylethyl.

48. A compound of claim 47, wherein R$_1$ is 4-heptyl.

49. A compound of claim 48, wherein A is selected from the group consisting of

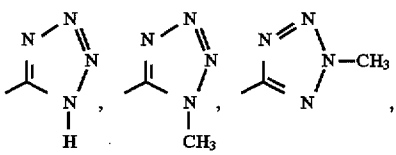

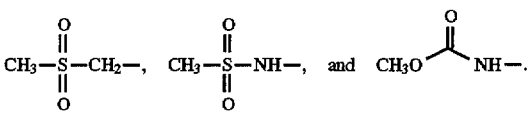

50. A compound of claim 49, where A is —CO$_2$H.

51. A pharmaceutical composition comprising a pharmaceutically acceptable carrier and a therapeutically effective amount of a compound of claim 1.

52. A pharmaceutical composition comprising a pharmaceutically acceptable carrier and a therapeutically effective amount of the compound of claim 11.

53. A composition comprising a radioactive atom complexed with a compound of claim 44 or 50.

54. A composition of claim 53, wherein the radioactive atom is selected from the group consisting of In-111 and Tc-99m.

55. A composition comprising a paramagnetic atom complexed with a compound of claim 44.

56. A composition of claim 55, wherein the paramagnetic atom is elected from the group consisting of gadolinium, copper, cobalt, nickel and manganese.

57. A diagnostic composition comprising a pharmaceutically acceptable carrier and a diagnostically effective amount of the compound of claim 44.

58. A diagnostic composition comprising a pharmaceutically acceptable carrier and a diagnostically effective amount of the compound of claim 50.

59. A diagnostic composition comprising a pharmaceutically acceptable carrier and a diagnostically effective amount of the composition of claim 54.

60. A diagnostic composition comprising a pharmaceutically acceptable carrier and a diagnostically effective amount of the composition of claim 56.

* * * * *

SEQUENCE LISTING ( 1 ) GENERAL INFORMATION:

( i i i ) NUMBER OF SEQUENCES: 165

( 2 ) INFORMATION FOR SEQ ID NO: 1:

( i ) SEQUENCE CHARACTERISTICS:
        ( A ) LENGTH: 5 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 1:

```
Gly   Gly   Val   Arg   Gly
 1                       5
```

( 2 ) INFORMATION FOR SEQ ID NO: 2:

( i ) SEQUENCE CHARACTERISTICS:
        ( A ) LENGTH: 5 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 2:

```
Phe   Ser   Ala   Arg   Gly
 1                       5
```

( 2 ) INFORMATION FOR SEQ ID NO: 3:

( i ) SEQUENCE CHARACTERISTICS:
        ( A ) LENGTH: 65 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 63 is Tyr(SO3).

( x i ) SEQUENCE DESCRIPTION: SEQ ID NO: 3:

```
Val  Val  Tyr  Thr  Asp  Cys  Thr  Glu  Ser  Gly  Gln  Asn  Leu  Cys
 1              5                            10

Leu  Cys  Glu  Gly  Ser  Asn  Val  Cys  Gly  Gln  Gly  Asn  Lys  Cys
15                  20                            25

Ile  Leu  Gly  Ser  Asp  Gly  Glu  Lys  Asn  Gln  Cys  Val  Thr  Gly
     30                       35                            40

Glu  Gly  Thr  Pro  Lys  Pro  Gln  Ser  His  Asn  Asp  Gly  Asp  Phe
          45                       50                            55

Glu  Glu  Ile  Pro  Glu  Glu  Xaa  Leu  Gln
               60                       65
```

( 2 ) INFORMATION FOR SEQ ID NO: 4:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 4:

```
Gly  Gly  Gly  Gly  Gly  Asn  Gly  Asp  Phe
 1                    5
```

( 2 ) INFORMATION FOR SEQ ID NO: 5:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 5:

```
Gly  Gly  Gly  Gly  Gly  Arg  Gly  Asp  Phe
 1                    5
```

( 2 ) INFORMATION FOR SEQ ID NO: 6:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 6:

```
        Glu   Glu   Ile   Pro   Glu   Tyr   Leu
        1                       5
```

( 2 ) INFORMATION FOR SEQ ID NO: 7:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 7:

```
Glu   Glu   Ile   Pro   Glu   Glu   Tyr   Leu
1                       5
```

( 2 ) INFORMATION FOR SEQ ID NO: 8:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 8:

```
Glu   Glu   Ile   Pro   Glu   Tyr   Leu
1                       5
```

( 2 ) INFORMATION FOR SEQ ID NO: 9:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 9:

```
Glu   Glu   Ile   Pro   Glu   Glu   Tyr   Leu
1                       5
```

( 2 ) INFORMATION FOR SEQ ID NO: 10:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 10:

```
Gly   Gly   Gly   Gly   Gly   Asn   Gly   Asp   Phe
1                       5
```

( 2 ) INFORMATION FOR SEQ ID NO: 11:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 11:

Glu   Glu   Ile   Pro   Glu   Tyr   Leu
1                                  5

( 2 ) INFORMATION FOR SEQ ID NO: 12:

( i ) SEQUENCE CHARACTERISTICS:
    ( A ) LENGTH: 9 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 12:

Gly   Gly   Gly   Gly   Gly   Asn   Gly   Asp   Phe
1                                  5

( 2 ) INFORMATION FOR SEQ ID NO: 13:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 13:

Glu   Glu   Ile   Pro   Glu   Glu   Tyr   Leu
1                                  5

( 2 ) INFORMATION FOR SEQ ID NO: 14:

( i ) SEQUENCE CHARACTERISTICS:
    ( A ) LENGTH: 9 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 14:

Gly   Gly   Gly   Gly   Gly   Arg   Gly   Asp   Phe
1                                  5

( 2 ) INFORMATION FOR SEQ ID NO: 15:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 15:

Glu   Glu   Ile   Pro   Glu   Tyr   Leu
1                       5

( 2 ) INFORMATION FOR SEQ ID NO: 16:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 16:

Gly   Gly   Gly   Gly   Gly   Arg   Gly   Asp   Phe
1                       5

( 2 ) INFORMATION FOR SEQ ID NO: 17:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 17:

Glu   Glu   Ile   Pro   Glu   Glu   Tyr   Leu
1                       5

( 2 ) INFORMATION FOR SEQ ID NO: 18:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 18:

Gly   Gly   Gly   Gly   Gly   Asn   Gly   Asp   Phe   Glu   Glu   Ile   Pro   Glu
1                       5                                   10

Tyr   Leu
15

( 2 ) INFORMATION FOR SEQ ID NO: 19:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 19:

Gly Gly Gly Gly Gly Asn Gly Asp Phe Glu Glu Ile Pro Glu
1               5                       10

Tyr Leu
15

( 2 ) INFORMATION FOR SEQ ID NO: 20:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 20:

Gly Gly Gly Gly Gly Asn Gly Asp Phe Glu Glu Ile Pro Glu
1               5                       10

Tyr Leu
15

( 2 ) INFORMATION FOR SEQ ID NO: 21:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 21:

Gly Gly Gly Gly Gly Asn Gly Asp Phe Glu Glu Ile Pro Glu
1               5                       10

Tyr Leu
15

( 2 ) INFORMATION FOR SEQ ID NO: 22:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 22:

Gly Gly Gly Gly Gly Asn Gly Asp Phe Glu Glu Ile Pro Glu
1               5                       10

Tyr Leu
15

( 2 ) INFORMATION FOR SEQ ID NO: 23:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 23:

Gly  Gly  Gly  Gly  Gly  Asn  Gly  Asp  Phe  Glu  Glu  Ile  Pro  Glu
1                     5                         10

Tyr  Leu
15

( 2 ) INFORMATION FOR SEQ ID NO: 24:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 24:

Gly  Gly  Gly  Gly  Gly  Asn  Gly  Asp  Phe  Glu  Glu  Ile  Pro  Glu
1                     5                         10

Tyr  Leu
15

( 2 ) INFORMATION FOR SEQ ID NO: 25:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 25:

Gly  Gly  Gly  Gly  Gly  Asn  Gly  Asp  Phe  Glu  Glu  Ile  Pro  Glu
1                     5                         10

Tyr  Leu
15

( 2 ) INFORMATION FOR SEQ ID NO: 26:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 26:

Gly  Gly  Gly  Gly  Gly  Asn  Gly  Asp  Phe  Glu  Glu  Ile  Pro  Glu
1                     5                         10

Tyr  Leu
15

( 2 ) INFORMATION FOR SEQ ID NO: 27:

( i ) SEQUENCE CHARACTERISTICS:
        ( A ) LENGTH: 16 AMINO ACIDS
        ( B ) TYPE: AMINO ACID
        ( D ) TOPOLOGY: LINEAR (ii) MOLECULE TYPE: PEPTIDE (ix) FEATURE:
    (D) OTHER INFORMATION:

(xi) SEQUENCE DESCRIPTION: SEQ ID NO: 27:

Gly Gly Gly Gly Gly Asn Gly Asp Phe Glu Glu Ile Pro Glu
1               5                   10
Tyr Leu
15

(2) INFORMATION FOR SEQ ID NO: 28:

(i) SEQUENCE CHARACTERISTICS:
        (A) LENGTH: 16 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 28:

Gly Gly Gly Gly Gly Arg Gly Asp Phe Glu Glu Ile Pro Glu
1               5                   10
Tyr Leu
15

(2) INFORMATION FOR SEQ ID NO: 29:

(i) SEQUENCE CHARACTERISTICS:
        (A) LENGTH: 16 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 29:

Gly Gly Gly Gly Gly Arg Gly Asp Phe Glu Glu Ile Pro Glu
1               5                   10
Tyr Leu
15

(2) INFORMATION FOR SEQ ID NO: 30:

(i) SEQUENCE CHARACTERISTICS:
        (A) LENGTH: 16 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 30:

Gly Gly Gly Gly Gly Arg Gly Asp Phe Glu Glu Ile Pro Glu
1               5                   10
Tyr Leu
15

(2) INFORMATION FOR SEQ ID NO: 31:

(i) SEQUENCE CHARACTERISTICS:

( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 31:

Gly  Gly  Gly  Gly  Gly  Arg  Gly  Asp  Phe  Glu  Glu  Ile  Pro  Glu
 1                    5                         10

Tyr  Leu
 15

( 2 ) INFORMATION FOR SEQ ID NO: 32:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 32:

Gly  Gly  Gly  Gly  Gly  Arg  Gly  Asp  Phe  Glu  Glu  Ile  Pro  Glu
 1                    5                         10

Tyr  Leu
 15

( 2 ) INFORMATION FOR SEQ ID NO: 33:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 33:

Gly  Gly  Gly  Gly  Gly  Arg  Gly  Asp  Phe  Glu  Glu  Ile  Pro  Glu
 1                    5                         10

Tyr  Leu
 15

( 2 ) INFORMATION FOR SEQ ID NO: 34:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 34:

Gly  Gly  Gly  Gly  Gly  Arg  Gly  Asp  Phe  Glu  Glu  Ile  Pro  Glu
 1                    5                         10

Tyr  Leu
 15

( 2 ) INFORMATION FOR SEQ ID NO: 35:

( i ) SEQUENCE CHARACTERISTICS:
    ( A ) LENGTH: 16 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 35:

Gly Gly Gly Gly Gly Arg Gly Asp Phe Glu Glu Ile Pro Glu
1               5                       10

Tyr Leu
15

( 2 ) INFORMATION FOR SEQ ID NO: 36:

( i ) SEQUENCE CHARACTERISTICS:
    ( A ) LENGTH: 16 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 36:

Gly Gly Gly Gly Gly Arg Gly Asp Phe Glu Glu Ile Pro Glu
1               5                       10

Tyr Leu
15

( 2 ) INFORMATION FOR SEQ ID NO: 37:

( i ) SEQUENCE CHARACTERISTICS:
    ( A ) LENGTH: 16 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 37:

Gly Gly Gly Gly Gly Arg Gly Asp Phe Glu Glu Ile Pro Glu
1               5                       10

Tyr Leu
15

( 2 ) INFORMATION FOR SEQ ID NO: 38:

( i ) SEQUENCE CHARACTERISTICS:
    ( A ) LENGTH: 17 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 38:

Gly Gly Gly Gly Gly Arg Gly Asp Phe Glu Glu Ile Pro Glu
1               5                       10

Glu Tyr Leu
15

( 2 ) INFORMATION FOR SEQ ID NO: 39:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 39:

Gly Gly Gly Gly Gly Arg Gly Asp Phe Glu Glu Ile Pro Glu
1               5                       10

Glu Tyr Leu
15

( 2 ) INFORMATION FOR SEQ ID NO: 40:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 40:

Gly Gly Gly Gly Gly Arg Gly Asp Phe Glu Glu Ile Pro Glu
1               5                       10

Glu Tyr Leu
15

( 2 ) INFORMATION FOR SEQ ID NO: 41:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 41:

Gly Gly Gly Gly Gly Arg Gly Asp Phe Glu Glu Ile Pro Glu
1               5                       10

Glu Tyr Leu
15

( 2 ) INFORMATION FOR SEQ ID NO: 42:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 42:

| Gly | Gly | Gly | Gly | Gly | Arg | Gly | Asp | Phe | Glu | Glu | Ile | Pro | Glu |
| 1   |     |     |     | 5   |     |     |     |     | 10  |     |     |     |     |

| Glu | Tyr | Leu |
| 15  |     |     |

( 2 ) INFORMATION FOR SEQ ID NO: 43:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 43:

| Gly | Gly | Gly | Gly | Gly | Arg | Gly | Asp | Phe | Glu | Glu | Ile | Pro | Glu |
| 1   |     |     |     | 5   |     |     |     |     | 10  |     |     |     |     |

| Glu | Tyr | Leu |
| 15  |     |     |

( 2 ) INFORMATION FOR SEQ ID NO: 44:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 44:

| Gly | Gly | Gly | Gly | Gly | Arg | Gly | Asp | Phe | Glu | Glu | Ile | Pro | Glu |
| 1   |     |     |     | 5   |     |     |     |     | 10  |     |     |     |     |

| Glu | Tyr | Leu |
| 15  |     |     |

( 2 ) INFORMATION FOR SEQ ID NO: 45:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 45:

| Gly | Gly | Gly | Gly | Gly | Arg | Gly | Asp | Phe | Glu | Glu | Ile | Pro | Glu |
| 1   |     |     |     | 5   |     |     |     |     | 10  |     |     |     |     |

| Glu | Tyr | Leu |
| 15  |     |     |

( 2 ) INFORMATION FOR SEQ ID NO: 46:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 46:

Gly Gly Gly Gly Gly Arg Gly Asp Phe Glu Glu Ile Pro Glu
1               5                   10

Glu Tyr Leu
15

( 2 ) INFORMATION FOR SEQ ID NO: 47:

( i ) SEQUENCE CHARACTERISTICS:
       ( A ) LENGTH: 17 AMINO ACIDS
       ( B ) TYPE: AMINO ACID
       ( D ) TOPOLOGY: LINEAR ( i i ) MOLECULE TYPE: PEPTIDE ( i x ) FEATURE:
       ( D ) OTHER INFORMATION:

( x i ) SEQUENCE DESCRIPTION: SEQ ID NO: 47:

Gly Gly Gly Gly Gly Arg Gly Asp Phe Glu Glu Ile Pro Glu
1               5                   10

Glu Tyr Leu
15

( 2 ) INFORMATION FOR SEQ ID NO: 48:

( i ) SEQUENCE CHARACTERISTICS:
       ( A ) LENGTH: 17 AMINO ACIDS
       ( B ) TYPE: AMINO ACID
       ( D ) TOPOLOGY: LINEAR ( i i ) MOLECULE TYPE: PEPTIDE ( i x ) FEATURE:
       ( D ) OTHER INFORMATION:

( x i ) SEQUENCE DESCRIPTION: SEQ ID NO: 48:

Gly Gly Gly Gly Gly Asn Gly Asp Phe Glu Glu Ile Pro Glu
1               5                   10

Glu Tyr Leu
15

( 2 ) INFORMATION FOR SEQ ID NO: 49:

( i ) SEQUENCE CHARACTERISTICS:
       ( A ) LENGTH: 17 AMINO ACIDS
       ( B ) TYPE: AMINO ACID
       ( D ) TOPOLOGY: LINEAR ( i i ) MOLECULE TYPE: PEPTIDE ( i x ) FEATURE:
       ( D ) OTHER INFORMATION:

( x i ) SEQUENCE DESCRIPTION: SEQ ID NO: 49:

Gly Gly Gly Gly Gly Asn Gly Asp Phe Glu Glu Ile Pro Glu
1               5                   10

Glu Tyr Leu
15

( 2 ) INFORMATION FOR SEQ ID NO: 50:

( i ) SEQUENCE CHARACTERISTICS:
       ( A ) LENGTH: 17 AMINO ACIDS (B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 50:

| Gly | Gly | Gly | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Glu | Tyr | Leu |
|-----|-----|-----|
| 15  |     |     |

(2) INFORMATION FOR SEQ ID NO: 51:

(i) SEQUENCE CHARACTERISTICS:
(A) LENGTH: 17 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 51:

| Gly | Gly | Gly | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Glu | Tyr | Leu |
|-----|-----|-----|
| 15  |     |     |

(2) INFORMATION FOR SEQ ID NO: 52:

(i) SEQUENCE CHARACTERISTICS:
(A) LENGTH: 17 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 52:

| Gly | Gly | Gly | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Glu | Tyr | Leu |
|-----|-----|-----|
| 15  |     |     |

(2) INFORMATION FOR SEQ ID NO: 53:

(i) SEQUENCE CHARACTERISTICS:
(A) LENGTH: 17 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 53:

| Gly | Gly | Gly | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Glu | Tyr | Leu |
|-----|-----|-----|
| 15  |     |     |

( 2 ) INFORMATION FOR SEQ ID NO: 54:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 54:

```
Gly   Gly   Gly   Gly   Gly   Asn   Gly   Asp   Phe   Glu   Glu   Ile   Pro   Glu
 1                       5                             10

Glu   Tyr   Leu
15
```

( 2 ) INFORMATION FOR SEQ ID NO: 55:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 55:

```
Gly   Gly   Gly   Gly   Gly   Asn   Gly   Asp   Phe   Glu   Glu   Ile   Pro   Glu
 1                       5                             10

Glu   Tyr   Leu
15
```

( 2 ) INFORMATION FOR SEQ ID NO: 56:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 56:

```
Gly   Gly   Gly   Gly   Gly   Asn   Gly   Asp   Phe   Glu   Glu   Ile   Pro   Glu
 1                       5                             10

Glu   Tyr   Leu
15
```

( 2 ) INFORMATION FOR SEQ ID NO: 57:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 57:

```
Gly   Gly   Gly   Gly   Gly   Asn   Gly   Asp   Phe   Glu   Glu   Ile   Pro   Glu
 1                       5                             10
```

Glu Tyr Leu
15

(2) INFORMATION FOR SEQ ID NO: 58:

(i) SEQUENCE CHARACTERISTICS:
        (A) LENGTH: 16 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 58:

Gly Gly Gly Gly Gly Asn Gly Asp Phe Glu Glu Ile Pro Glu
1               5                   10

Tyr Leu
15

(2) INFORMATION FOR SEQ ID NO: 59:

(i) SEQUENCE CHARACTERISTICS:
        (A) LENGTH: 16 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 59:

Gly Gly Gly Gly Gly Arg Gly Asp Phe Glu Glu Ile Pro Glu
1               5                   10

Tyr Leu
15

(2) INFORMATION FOR SEQ ID NO: 60:

(i) SEQUENCE CHARACTERISTICS:
        (A) LENGTH: 17 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 60:

Gly Gly Gly Gly Gly Arg Gly Asp Phe Glu Glu Ile Pro Glu
1               5                   10

Glu Tyr Leu
15

(2) INFORMATION FOR SEQ ID NO: 61:

(i) SEQUENCE CHARACTERISTICS:
        (A) LENGTH: 17 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 61:

```
Gly   Gly   Gly   Gly   Gly   Asn   Gly   Asp   Phe   Glu   Glu   Ile   Pro   Glu
 1                       5                             10

Glu   Tyr   Leu
15
```

(2) INFORMATION FOR SEQ ID NO: 62:

(i) SEQUENCE CHARACTERISTICS:
        (A) LENGTH: 9 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 62:

```
Gly   Gly   Gly   Gly   Gly   Asn   Gly   Asp   Phe
 1                       5
```

(2) INFORMATION FOR SEQ ID NO: 63:

(i) SEQUENCE CHARACTERISTICS:
        (A) LENGTH: 9 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 63:

```
Gly   Gly   Gly   Gly   Gly   Arg   Gly   Asp   Phe
 1                       5
```

(2) INFORMATION FOR SEQ ID NO: 64:

(i) SEQUENCE CHARACTERISTICS:
        (A) LENGTH: 7 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa at location 6 is Tyr(3,5-diiodo).

(xi) SEQUENCE DESCRIPTION: SEQ ID NO: 64:

```
Glu   Glu   Ile   Pro   Glu   Xaa   Leu
 1                       5
```

(2) INFORMATION FOR SEQ ID NO: 65:

(i) SEQUENCE CHARACTERISTICS:
        (A) LENGTH: 7 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa at location 6 is Tyr(3,5-diiodo).

(xi) SEQUENCE DESCRIPTION: SEQ ID NO: 65:

```
Glu   Glu   Ile   Pro   Glu   Xaa   Leu
 1                       5
```

( 2 ) INFORMATION FOR SEQ ID NO: 66:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
     Xaa at location 6 is Tyr(3-iodo).

( x i ) SEQUENCE DESCRIPTION: SEQ ID NO: 66:

Glu Glu Ile Pro Glu Xaa Leu
1          5

( 2 ) INFORMATION FOR SEQ ID NO: 67:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
     Xaa at location 6 is Tyr(3,5-diiodo).

( x i ) SEQUENCE DESCRIPTION: SEQ ID NO: 67:

Glu Glu Ile Pro Glu Xaa Leu
1          5

( 2 ) INFORMATION FOR SEQ ID NO: 68:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
     Xaa at location 7 is Tyr(3-iodo).

( x i ) SEQUENCE DESCRIPTION: SEQ ID NO: 68:

Glu Glu Ile Pro Glu Glu Xaa Leu
1          5

( 2 ) INFORMATION FOR SEQ ID NO: 69:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
     Xaa at location 7 is Tyr(3,5-diiodo).

( x i ) SEQUENCE DESCRIPTION: SEQ ID NO: 69:

Glu Glu Ile Pro Glu Glu Xaa Leu
1          5

( 2 ) INFORMATION FOR SEQ ID NO: 70:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
        Xaa at location 7 is Tyr(3-iodo).

( x i ) SEQUENCE DESCRIPTION: SEQ ID NO: 70:

Glu Glu Ile Pro Glu Glu Xaa Leu
1                   5

( 2 ) INFORMATION FOR SEQ ID NO: 71:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
        Xaa at location 7 is Tyr(3,5-diiodo).

( x i ) SEQUENCE DESCRIPTION: SEQ ID NO: 71:

Glu Glu Ile Pro Glu Glu Xaa Leu
1                   5

( 2 ) INFORMATION FOR SEQ ID NO: 72:

( i ) SEQUENCE CHARACTERISTICS:
    ( A ) LENGTH: 9 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 72:

Gly Gly Gly Gly Gly Asn Gly Asp Phe
1                   5

( 2 ) INFORMATION FOR SEQ ID NO: 73:

( i ) SEQUENCE CHARACTERISTICS:
    ( A ) LENGTH: 9 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 73:

Gly Gly Gly Gly Gly Arg Gly Asp Phe
1                   5

( 2 ) INFORMATION FOR SEQ ID NO: 74:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
        Xaa at location 6 is Tyr(3-iodo).

( x i ) SEQUENCE DESCRIPTION: SEQ ID NO: 74:

Glu  Glu  Ile  Pro  Glu  Xaa  Leu
1                   5

( 2 ) INFORMATION FOR SEQ ID NO: 75:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 6 is Tyr(3,5-diiodo).

( x i ) SEQUENCE DESCRIPTION: SEQ ID NO: 75:

Glu  Glu  Ile  Pro  Glu  Xaa  Leu
1                   5

( 2 ) INFORMATION FOR SEQ ID NO: 76:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 7 is Tyr(3-iodo).

( x i ) SEQUENCE DESCRIPTION: SEQ ID NO: 76:

Glu  Glu  Ile  Pro  Glu  Glu  Xaa  Leu
1                   5

( 2 ) INFORMATION FOR SEQ ID NO: 77:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 7 is Tyr(3,5-diiodo).

( x i ) SEQUENCE DESCRIPTION: SEQ ID NO: 77:

Glu  Glu  Ile  Pro  Glu  Glu  Xaa  Leu
1                   5

( 2 ) INFORMATION FOR SEQ ID NO: 78:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 78:

Glu  Glu  Ile  Pro  Glu  Tyr  Leu
 1                    5

( 2 ) INFORMATION FOR SEQ ID NO: 79:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 79:

Glu  Glu  Ile  Pro  Glu  Glu  Tyr  Leu
 1                    5

( 2 ) INFORMATION FOR SEQ ID NO: 80:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 80:

Glu  Glu  Ile  Pro  Glu  Tyr  Leu
 1                    5

( 2 ) INFORMATION FOR SEQ ID NO: 81:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 81:

Glu  Glu  Ile  Pro  Glu  Glu  Tyr  Leu
 1                    5

( 2 ) INFORMATION FOR SEQ ID NO: 82:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 82:

Glu  Glu  Ile  Pro  Glu  Tyr  Leu
 1                    5

( 2 ) INFORMATION FOR SEQ ID NO: 83:

(i) SEQUENCE CHARACTERISTICS:
        (A) LENGTH: 8 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 83:

Glu  Glu  Ile  Pro  Glu  Glu  Tyr  Leu
1                   5

(2) INFORMATION FOR SEQ ID NO: 84:

(i) SEQUENCE CHARACTERISTICS:
        (A) LENGTH: 9 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa at location 3 is X.

(xi) SEQUENCE DESCRIPTION: SEQ ID NO: 84:

Gly  Gly  Xaa  Gly  Gly  Asn  Gly  Asp  Phe
1                   5

(2) INFORMATION FOR SEQ ID NO: 85:

(i) SEQUENCE CHARACTERISTICS:
        (A) LENGTH: 9 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa at location 6 is X.

(xi) SEQUENCE DESCRIPTION: SEQ ID NO: 85:

Gly  Gly  Xaa  Gly  Gly  Arg  Gly  Asp  Phe
1                   5

(2) INFORMATION FOR SEQ ID NO: 86:

(i) SEQUENCE CHARACTERISTICS:
        (A) LENGTH: 9 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa at location 6 is X.

(xi) SEQUENCE DESCRIPTION: SEQ ID NO: 86:

Gly  Gly  Gly  Gly  Gly  Xaa  Gly  Asp  Phe
1                   5

(2) INFORMATION FOR SEQ ID NO: 87:

(i) SEQUENCE CHARACTERISTICS:
        (A) LENGTH: 16 AMINO ACIDS
        (B) TYPE: AMINO ACID
        (D) TOPOLOGY: LINEAR (ii) MOLECULE TYPE: PEPTIDE (ix) FEATURE:
 (D) OTHER INFORMATION:

(xi) SEQUENCE DESCRIPTION: SEQ ID NO: 87:

| Pro | Gly | Gly | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Tyr | Leu |
|-----|-----|
| 15  |     |

(2) INFORMATION FOR SEQ ID NO: 88:

(i) SEQUENCE CHARACTERISTICS:
  (A) LENGTH: 16 AMINO ACIDS
  (B) TYPE: AMINO ACID
  (D) TOPOLOGY: LINEAR (ii) MOLECULE TYPE: PEPTIDE (ix) FEATURE:
  (D) OTHER INFORMATION:
   Xaa at location 15 is Tyr(O-SO3H).

(xi) SEQUENCE DESCRIPTION: SEQ ID NO: 88:

| Gly | Gly | Gly | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Xaa | Leu |
|-----|-----|
| 15  |     |

(2) INFORMATION FOR SEQ ID NO: 89:

(i) SEQUENCE CHARACTERISTICS:
  (A) LENGTH: 16 AMINO ACIDS
  (B) TYPE: AMINO ACID
  (D) TOPOLOGY: LINEAR (ii) MOLECULE TYPE: PEPTIDE (ix) FEATURE:
  (D) OTHER INFORMATION:
   Xaa at location 15 is Tyr(3,5-diiodo).

(xi) SEQUENCE DESCRIPTION: SEQ ID NO: 89:

| Gly | Gly | Gly | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Xaa | Leu |
|-----|-----|
| 15  |     |

(2) INFORMATION FOR SEQ ID NO: 90:

(i) SEQUENCE CHARACTERISTICS:
  (A) LENGTH: 16 AMINO ACIDS
  (B) TYPE: AMINO ACID
  (D) TOPOLOGY: LINEAR (ii) MOLECULE TYPE: PEPTIDE (ix) FEATURE:
  (D) OTHER INFORMATION:

(xi) SEQUENCE DESCRIPTION: SEQ ID NO: 90:

| Gly | Gly | Lys | Gly | Gly | Asn | Gly | Asp | Phe | Glu | Glu | Ile | Pro | Glu |
|-----|-----|-----|-----|-----|-----|-----|-----|-----|-----|-----|-----|-----|-----|
| 1   |     |     |     | 5   |     |     |     |     | 10  |     |     |     |     |

| Tyr | Leu |
|-----|-----|
| 15  |     |

(2) INFORMATION FOR SEQ ID NO: 91:

( i ) SEQUENCE CHARACTERISTICS:
 ( A ) LENGTH: 13 AMINO ACIDS
 ( B ) TYPE: AMINO ACID
 ( D ) TOPOLOGY: LINEAR ( i i ) MOLECULE TYPE: PEPTIDE ( i x ) FEATURE:
 ( D ) OTHER INFORMATION:

( x i ) SEQUENCE DESCRIPTION: SEQ ID NO: 91:

Gly Gly Asn Gly Asp Phe Glu Glu Ile Pro Glu Tyr Leu
1               5                   10

( 2 ) INFORMATION FOR SEQ ID NO: 92:

( i ) SEQUENCE CHARACTERISTICS:
  ( A ) LENGTH: 13 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 92:

Gly Gly Asn Gly Asp Phe Glu Glu Ile Pro Glu Tyr Leu
1               5                   10

( 2 ) INFORMATION FOR SEQ ID NO: 93:

( i ) SEQUENCE CHARACTERISTICS:
  ( A ) LENGTH: 16 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 93:

Gly Gly Gly Gly Gly Arg Gly Asp Phe Glu Glu Ile Pro Glu
1               5                   10

Tyr Leu
15

( 2 ) INFORMATION FOR SEQ ID NO: 94:

( i ) SEQUENCE CHARACTERISTICS:
  ( A ) LENGTH: 16 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 94:

Gly Gly Gly Gly Gly Arg Gly Asp Phe Glu Glu Ile Pro Glu
1               5                   10

Tyr Leu
15

( 2 ) INFORMATION FOR SEQ ID NO:95:

( i ) SEQUENCE CHARACTERISTICS:

( A ) LENGTH: 16 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 95:

Gly Gly Gly Gly Gly Arg Gly Asp Phe Glu Glu Ile Pro Glu
 1               5                   10

Tyr Leu
 15

( 2 ) INFORMATION FOR SEQ ID NO: 96:

( i ) SEQUENCE CHARACTERISTICS:
    ( A ) LENGTH: 9 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 96:

Gly Gly Gly Gly Gly Asn Gly Asp Phe
 1               5

( 2 ) INFORMATION FOR SEQ ID NO: 97:

( i ) SEQUENCE CHARACTERISTICS:
    ( A ) LENGTH: 9 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 97:

Gly Gly Gly Gly Gly Arg Gly Asp Phe
 1               5

( 2 ) INFORMATION FOR SEQ ID NO: 98:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 98:

Glu Glu Ile Pro Glu Tyr Leu
 1               5

( 2 ) INFORMATION FOR SEQ ID NO: 99:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 99:

Glu  Glu  Ile  Pro  Glu  Glu  Tyr  Leu
1                   5

( 2 ) INFORMATION FOR SEQ ID NO: 100:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
      Xaa at location 6 is Tyr(3-iodo).

( x i ) SEQUENCE DESCRIPTION: SEQ ID NO: 100:

Glu  Glu  Ile  Pro  Glu  Xaa  Leu
1                   5

( 2 ) INFORMATION FOR SEQ ID NO: 101:

( i ) SEQUENCE CHARACTERISTICS:
    ( A ) LENGTH: 7 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
      Xaa at location 6 is Tyr(3,5-diiodo).

( x i ) SEQUENCE DESCRIPTION: SEQ ID NO: 101:

Glu  Glu  Ile  Pro  Glu  Xaa  Leu
1                   5

( 2 ) INFORMATION FOR SEQ ID NO: 102:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
      Xaa at location 7 is Tyr(3-iodo).

( x i ) SEQUENCE DESCRIPTION: SEQ ID NO: 102:

Glu  Glu  Ile  Pro  Glu  Glu  Xaa  Leu
1                   5

( 2 ) INFORMATION FOR SEQ ID NO: 103:

( i ) SEQUENCE CHARACTERISTICS:
    ( A ) LENGTH: 8 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:
      Xaa at location 7 is Tyr(3,5-diiodo).

( x i ) SEQUENCE DESCRIPTION: SEQ ID NO: 103:

Glu  Glu  Ile  Pro  Glu  Glu  Xaa  Leu
 1                    5

( 2 ) INFORMATION FOR SEQ ID NO: 104:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 104:

Glu  Glu  Ile  Pro  Glu  Tyr  Leu
 1                    5

( 2 ) INFORMATION FOR SEQ ID NO: 105:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 105:

Glu  Glu  Ile  Pro  Glu  Glu  Tyr  Leu
 1                    5

( 2 ) INFORMATION FOR SEQ ID NO: 106:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 6 is Tyr(3-iodo).

( x i ) SEQUENCE DESCRIPTION: SEQ ID NO: 106:

Glu  Glu  Ile  Pro  Glu  Xaa  Leu
 1                    5

( 2 ) INFORMATION FOR SEQ ID NO: 107:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 6 is Tyr(3,5-diiodo).

( x i ) SEQUENCE DESCRIPTION: SEQ ID NO: 107:

Glu  Glu  Ile  Pro  Glu  Xaa  Leu
 1                    5

( 2 ) INFORMATION FOR SEQ ID NO: 108:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 7 is Tyr(3-iodo).

( x i ) SEQUENCE DESCRIPTION: SEQ ID NO: 108:

Glu   Glu   Ile   Pro   Glu   Glu   Xaa   Leu
1                                 5

( 2 ) INFORMATION FOR SEQ ID NO: 109:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 7 is Tyr(3,5-diiodo).

( x i ) SEQUENCE DESCRIPTION: SEQ ID NO: 109:

Glu   Glu   Ile   Pro   Glu   Glu   Xaa   Leu
1                                 5

( 2 ) INFORMATION FOR SEQ ID NO: 110:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 110:

Gly   Gly   Gly   Gly   Gly   Asn   Gly   Asp   Phe
1                                 5

( 2 ) INFORMATION FOR SEQ ID NO: 111:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 111:

Glu   Glu   Ile   Pro   Glu   Tyr   Leu
1                                 5

( 2 ) INFORMATION FOR SEQ ID NO: 112:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 112:

Gly Gly Gly Gly Gly Asn Gly Asp Phe
1               5

( 2 ) INFORMATION FOR SEQ ID NO: 113:

( i ) SEQUENCE CHARACTERISTICS:
( A ) LENGTH: 8 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 113:

Glu Glu Ile Pro Glu Glu Tyr Leu
1               5

( 2 ) INFORMATION FOR SEQ ID NO: 114:

( i ) SEQUENCE CHARACTERISTICS:
( A ) LENGTH: 9 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 114:

Gly Gly Gly Gly Gly Arg Gly Asp Phe
1               5

( 2 ) INFORMATION FOR SEQ ID NO: 115:

( i ) SEQUENCE CHARACTERISTICS:
( A ) LENGTH: 7 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 115:

Glu Glu Ile Pro Glu Tyr Leu
1               5

( 2 ) INFORMATION FOR SEQ ID NO: 116:

( i ) SEQUENCE CHARACTERISTICS:
( A ) LENGTH: 9 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 116:

```
Gly   Gly   Gly   Gly   Gly   Arg   Gly   Asp   Phe
 1                             5
```

( 2 ) INFORMATION FOR SEQ ID NO: 117:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 117:

```
Glu   Glu   Ile   Pro   Glu   Glu   Tyr   Leu
 1                       5
```

( 2 ) INFORMATION FOR SEQ ID NO: 118:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 6 is Tyr(3-iodo).

( x i ) SEQUENCE DESCRIPTION: SEQ ID NO: 118:

```
Glu   Glu   Ile   Pro   Glu   Xaa   Leu
 1                       5
```

( 2 ) INFORMATION FOR SEQ ID NO: 119:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 6 is Tyr(3,5-diiodo).

( x i ) SEQUENCE DESCRIPTION: SEQ ID NO: 119:

```
Glu   glu   Ile   Pro   Glu   Xaa   Leu
 1                       5
```

( 2 ) INFORMATION FOR SEQ ID NO: 120:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 7 is Tyr(3-iodo).

( x i ) SEQUENCE DESCRIPTION: SEQ ID NO: 120:

```
Glu   Glu   Ile   Pro   Glu   Glu   Xaa   Leu
 1                       5
```

( 2 ) INFORMATION FOR SEQ ID NO: 121:

(i) SEQUENCE CHARACTERISTICS:
    (A) LENGTH: 8 AMINO ACIDS
    (B) TYPE: AMINO ACID
    (D) TOPOLOGY: LINEAR (ii) MOLECULE TYPE: PEPTIDE (ix) FEATURE:
    (D) OTHER INFORMATION:
        Xaa at location 7 is Tyr(3,5-diiodo).

(xi) SEQUENCE DESCRIPTION: SEQ ID NO: 121:

Glu  Glu  Ile  Pro  Glu  Glu  Xaa  Leu
 1                    5

(2) INFORMATION FOR SEQ ID NO: 122:

(i) SEQUENCE CHARACTERISTICS:
    (A) LENGTH: 7 AMINO ACIDS
    (B) TYPE: AMINO ACID
    (D) TOPOLOGY: LINEAR (ii) MOLECULE TYPE: PEPTIDE (ix) FEATURE:
    (D) OTHER INFORMATION:
        Xaa at location 6 is Tyr(3-iodo).

(xi) SEQUENCE DESCRIPTION: SEQ ID NO: 122:

Glu  Glu  Ile  Pro  Glu  Xaa  Leu
 1                    5

(2) INFORMATION FOR SEQ ID NO: 123:

(i) SEQUENCE CHARACTERISTICS:
    (A) LENGTH: 7 AMINO ACIDS
    (B) TYPE: AMINO ACID
    (D) TOPOLOGY: LINEAR (ii) MOLECULE TYPE: PEPTIDE (ix) FEATURE:
    (D) OTHER INFORMATION:
        Xaa at location 6 is Tyr(3,5-diiodo).

(xi) SEQUENCE DESCRIPTION: SEQ ID NO: 123:

Glu  Glu  Ile  Pro  Glu  Xaa  Leu
 1                    5

(2) INFORMATION FOR SEQ ID NO: 124:

(i) SEQUENCE CHARACTERISTICS:
    (A) LENGTH: 8 AMINO ACIDS
    (B) TYPE: AMINO ACID
    (D) TOPOLOGY: LINEAR (ii) MOLECULE TYPE: PEPTIDE (ix) FEATURE:
    (D) OTHER INFORMATION:
        Xaa at location 7 is Tyr(3-iodo).

(xi) SEQUENCE DESCRIPTION: SEQ ID NO: 124:

Glu  Glu  Ile  Pro  Glu  Glu  Xaa  Leu
 1                    5

(2) INFORMATION FOR SEQ ID NO: 125:

(i) SEQUENCE CHARACTERISTICS:
    (A) LENGTH: 8 AMINO ACIDS
    (B) TYPE: AMINO ACID ( D ) TOPOLOGY: LINEAR ( i i ) MOLECULE TYPE: PEPTIDE ( i x ) FEATURE:
    ( D ) OTHER INFORMATION:
        Xaa at location 7 is Tyr(3,5-diiodo).

( x i ) SEQUENCE DESCRIPTION: SEQ ID NO: 125:

Glu　Glu　Ile　Pro　Glu　Glu　Xaa　Leu ( 2 ) INFORMATION FOR SEQ ID NO: 126:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 126:

Gly　Gly　Gly　Gly　Gly　Asn　Gly　Asp　Phe
1　　　　　　　　　　　　5

( 2 ) INFORMATION FOR SEQ ID NO: 127:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
        Xaa in location 6 is Tyr(3-iodo).

( x i ) SEQUENCE DESCRIPTION: SEQ ID NO: 127:

Glu　Glu　Ile　Pro　Glu　Xaa　Leu
1　　　　　　　　　　5

( 2 ) INFORMATION FOR SEQ ID NO: 128:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
        Xaa in location 6 is Tyr(3,5-diiodo).

( x i ) SEQUENCE DESCRIPTION: SEQ ID NO: 128:

Glu　Glu　Ile　Pro　Glu　Xaa　Leu
1　　　　　　　　　　5

( 2 ) INFORMATION FOR SEQ ID NO: 129:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

(xi) SEQUENCE DESCRIPTION: SEQ ID NO: 129:

Gly Gly Gly Gly Gly Asn Gly Asp Phe
1               5

(2) INFORMATION FOR SEQ ID NO: 130:

(i) SEQUENCE CHARACTERISTICS:
        (A) LENGTH: 8 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa in location 7 is Tyr(3-iodo).

(xi) SEQUENCE DESCRIPTION: SEQ ID NO: 130:

Glu Glu Ile Pro Glu Glu Xaa Leu
1               5

(2) INFORMATION FOR SEQ ID NO: 131:

(i) SEQUENCE CHARACTERISTICS:
        (A) LENGTH: 8 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa in location 7 is Tyr(3,5-diiodo).

(xi) SEQUENCE DESCRIPTION: SEQ ID NO: 131:

Glu Glu Ile Pro Glu Glu Xaa Leu
1               5

(2) INFORMATION FOR SEQ ID NO: 132:

(i) SEQUENCE CHARACTERISTICS:
        (A) LENGTH: 9 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 132:

Gly Gly Gly Gly Gly Arg Gly Asp Phe
1               5

(2) INFORMATION FOR SEQ ID NO: 133:

(i) SEQUENCE CHARACTERISTICS:
        (A) LENGTH: 7 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa in location 6 is Tyr(3-iodo).

(xi) SEQUENCE DESCRIPTION: SEQ ID NO: 133:

Glu Glu Ile Pro Glu Xaa Leu
1               5

( 2 ) INFORMATION FOR SEQ ID NO: 134:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 6 is Tyr(3,5-diiodo).

( x i ) SEQUENCE DESCRIPTION: SEQ ID NO: 134:

Glu Glu Ile Pro Glu Xaa Leu
1               5

( 2 ) INFORMATION FOR SEQ ID NO: 135:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 135:

Gly Gly Gly Gly Gly Arg Gly Asp Phe
1               5

( 2 ) INFORMATION FOR SEQ ID NO: 136:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 7 is Tyr(3-iodo).

( x i ) SEQUENCE DESCRIPTION: SEQ ID NO: 136:

Glu Glu Ile Pro Glu Glu Xaa Leu
1               5

( 2 ) INFORMATION FOR SEQ ID NO: 137:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 7 is Tyr(3,5-diiodo)

( x i ) SEQUENCE DESCRIPTION: SEQ ID NO: 137:

Glu Glu Ile Pro Glu Glu Xaa Leu
1               5

( 2 ) INFORMATION FOR SEQ ID NO: 138:

( i ) SEQUENCE CHARACTERISTICS:

(A) LENGTH: 9 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:
Xaa in location 1 is X.

(xi) SEQUENCE DESCRIPTION: SEQ ID NO: 138:

Xaa Gly Gly Gly Gly Asn Gly Asp Phe
1               5

(2) INFORMATION FOR SEQ ID NO: 139:

(i) SEQUENCE CHARACTERISTICS:
(A) LENGTH: 9 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:
Xaa in location 2 is X.

(xi) SEQUENCE DESCRIPTION: SEQ ID NO: 139:

Gly Xaa Gly Gly Gly Asn Gly Asp Phe
1               5

(2) INFORMATION FOR SEQ ID NO: 140:

(i) SEQUENCE CHARACTERISTICS:
(A) LENGTH: 9 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:
Xaa in location 3 is X.

(xi) SEQUENCE DESCRIPTION: SEQ ID NO: 140:

Gly Gly Xaa Gly Gly Asn Gly Asp Phe
1               5

(2) INFORMATION FOR SEQ ID NO: 141:

(i) SEQUENCE CHARACTERISTICS:
(A) LENGTH: 9 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:
Xaa in location 4 is X.

(xi) SEQUENCE DESCRIPTION: SEQ ID NO: 141:

Gly Gly Gly Xaa Gly Asn Gly Asp Phe
1               5

(2) INFORMATION FOR SEQ ID NO: 142:

(i) SEQUENCE CHARACTERISTICS:
(A) LENGTH: 9 AMINO ACIDS
(B) TYPE: AMINO ACID
(D) TOPOLOGY: LINEAR (i i) MOLECULE TYPE: PEPTIDE (i x) FEATURE:
(D) OTHER INFORMATION:
Xaa in location 5 is X.

(x i) SEQUENCE DESCRIPTION: SEQ ID NO: 142:

Gly   Gly   Gly   Gly   Xaa   Asn   Gly   Asp   Phe
 1                       5

(2) INFORMATION FOR SEQ ID NO: 143:

(i) SEQUENCE CHARACTERISTICS:
(A) LENGTH: 9 AMINO ACIDS
(B) TYPE: AMINO ACID
(D) TOPOLOGY: LINEAR (i i) MOLECULE TYPE: PEPTIDE (i x) FEATURE:
(D) OTHER INFORMATION:
Xaa in location 1 is X.

(x i) SEQUENCE DESCRIPTION: SEQ ID NO: 143:

Xaa   Gly   Gly   Gly   Gly   Arg   Gly   Asp   Phe
 1                       5

(2) INFORMATION FOR SEQ ID NO: 144:

(i) SEQUENCE CHARACTERISTICS:
(A) LENGTH: 9 AMINO ACIDS
(B) TYPE: AMINO ACID
(D) TOPOLOGY: LINEAR (i i) MOLECULE TYPE: PEPTIDE (i x) FEATURE:
(D) OTHER INFORMATION:
Xaa in location 2 is X.

(x i) SEQUENCE DESCRIPTION: SEQ ID NO: 144:

Gly   Xaa   Gly   Gly   Gly   Arg   Gly   Asp   Phe
 1                       5

(2) INFORMATION FOR SEQ ID NO: 145:

(i) SEQUENCE CHARACTERISTICS:
(A) LENGTH: 9 AMINO ACIDS
(B) TYPE: AMINO ACID
(D) TOPOLOGY: LINEAR (i i) MOLECULE TYPE: PEPTIDE (i x) FEATURE:
(D) OTHER INFORMATION:
Xaa in location 3 is X.

(x i) SEQUENCE DESCRIPTION: SEQ ID NO: 145:

Gly   Gly   Xaa   Gly   Gly   Arg   Gly   Asp   Phe
 1                       5

(2) INFORMATION FOR SEQ ID NO: 146:

(i) SEQUENCE CHARACTERISTICS:
(A) LENGTH: 9 AMINO ACIDS
(B) TYPE: AMINO ACID
(D) TOPOLOGY: LINEAR (i i) MOLECULE TYPE: PEPTIDE (i x) FEATURE:
(D) OTHER INFORMATION:

Xaa in position 4 is X.

( x i ) SEQUENCE DESCRIPTION: SEQ ID NO: 146:

Gly  Gly  Gly  Xaa  Gly  Arg  Gly  Asp  Phe
1                  5

( 2 ) INFORMATION FOR SEQ ID NO: 147:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 5 is X.

( x i ) SEQUENCE DESCRIPTION: SEQ ID NO: 147:

Gly  Gly  Gly  Gly  Xaa  Arg  Gly  Asp  Phe
1                  5

( 2 ) INFORMATION FOR SEQ ID NO: 148:

( i ) SEQUENCE CHARACTERISTICS:
        ( A ) LENGTH: 9 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 6 is X.

( x i ) SEQUENCE DESCRIPTION: SEQ ID NO: 148:

Gly  Gly  Gly  Gly  Gly  Xaa  Gly  Asp  Phe
1                  5

( 2 ) INFORMATION FOR SEQ ID NO: 149:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 149:

Glu  Glu  Ile  Pro  Glu  Tyr  Leu
1                  5

( 2 ) INFORMATION FOR SEQ ID NO: 150:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 150:

Glu  Glu  Ile  Pro  Glu  Glu  Tyr  Leu
1                  5

( 2 ) INFORMATION FOR SEQ ID NO: 151:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 6 is Tyr(3-iodo).

( x i ) SEQUENCE DESCRIPTION: SEQ ID NO: 151:

Glu  Glu  Ile  Pro  Glu  Xaa  Leu
1                        5

( 2 ) INFORMATION FOR SEQ ID NO: 152:

( i ) SEQUENCE CHARACTERISTICS:
        ( A ) LENGTH: 7 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 6 is Tyr(3,5-diiodo).

( x i ) SEQUENCE DESCRIPTION: SEQ ID NO: 152:

Glu  Glu  Ile  Pro  Glu  Xaa  Leu
1                        5

( 2 ) INFORMATION FOR SEQ ID NO: 153:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 7 is Tyr(3-iodo).

( x i ) SEQUENCE DESCRIPTION: SEQ ID NO: 153:

Glu  Glu  Ile  Pro  Glu  Glu  Xaa  Leu
1                        5

( 2 ) INFORMATION FOR SEQ ID NO: 154:

( i ) SEQUENCE CHARACTERISTICS:
        ( A ) LENGTH: 8 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa in location 7 is Tyr(3,5-diiodo).

( x i ) SEQUENCE DESCRIPTION: SEQ ID NO: 154:

Glu  Glu  Ile  Pro  Glu  Glu  Xaa  Leu
1                        5

( 2 ) INFORMATION FOR SEQ ID NO: 155:

( i ) SEQUENCE CHARACTERISTICS:
   ( A ) LENGTH: 7 AMINO ACIDS
   ( B ) TYPE: AMINO ACID
   ( D ) TOPOLOGY: LINEAR ( i i ) MOLECULE TYPE: PEPTIDE ( i x ) FEATURE:
   ( D ) OTHER INFORMATION:

( x i ) SEQUENCE DESCRIPTION: SEQ ID NO: 155:

Glu  Glu  Ile  Pro  Glu  Tyr  Leu
1                    5

( 2 ) INFORMATION FOR SEQ ID NO: 156:

( i ) SEQUENCE CHARACTERISTICS:
      ( A ) LENGTH: 8 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:

( x i ) SEQUENCE DESCRIPTION: SEQ ID NO: 156:

Glu  Glu  Ile  Pro  Glu  Glu  Tyr  Leu
1                    5

( 2 ) INFORMATION FOR SEQ ID NO: 157:

( i ) SEQUENCE CHARACTERISTICS:
      ( A ) LENGTH: 7 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:
         Xaa in location 6 is Tyr(3-iodo).

( x i ) SEQUENCE DESCRIPTION: SEQ ID NO: 157:

Glu  Glu  Ile  Pro  Glu  Xaa  Leu
1                    5

( 2 ) INFORMATION FOR SEQ ID NO: 158:

( i ) SEQUENCE CHARACTERISTICS:
      ( A ) LENGTH: 7 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:
         Xaa in location 6 is Tyr(3,5-diiodo).

( x i ) SEQUENCE DESCRIPTION: SEQ ID NO: 158:

Glu  Glu  Ile  Pro  Glu  Xaa  Leu
1                    5

( 2 ) INFORMATION FOR SEQ ID NO: 159:

( i ) SEQUENCE CHARACTERISTICS:
      ( A ) LENGTH: 8 AMINO ACIDS
      ( B ) TYPE: AMINO ACID
      ( D ) TOPOLOGY: LINEAR ( i i ) MOLECULE TYPE: PEPTIDE ( i x ) FEATURE:
        ( D ) OTHER INFORMATION:
                Xaa in location 7 is Tyr(3-iodo).

( x i ) SEQUENCE DESCRIPTION: SEQ ID NO: 159:

Glu  Glu  Ile  Pro  Glu  Glu  Xaa  Leu
1                     5

( 2 ) INFORMATION FOR SEQ ID NO: 160:

( i ) SEQUENCE CHARACTERISTICS:
            ( A ) LENGTH: 8 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:
                    Xaa in location 7 is Tyr(3,5-diiodo).

( x i ) SEQUENCE DESCRIPTION: SEQ ID NO: 160:

Glu  Glu  Ile  Pro  Glu  Glu  Xaa  Leu
1                     5

( 2 ) INFORMATION FOR SEQ ID NO: 161:

( i ) SEQUENCE CHARACTERISTICS:
            ( A ) LENGTH: 7 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 161:

Glu  Glu  Ile  Pro  Glu  Tyr  Leu
1                     5

( 2 ) INFORMATION FOR SEQ ID NO: 162:

( i ) SEQUENCE CHARACTERISTICS:
            ( A ) LENGTH: 8 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 162:

Glu  Glu  Ile  Pro  Glu  Glu  Tyr  Leu
1                     5

( 2 ) INFORMATION FOR SEQ ID NO: 163:

( i ) SEQUENCE CHARACTERISTICS:
            ( A ) LENGTH: 9 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:
                    Xaa in location 3 is X.

( x i ) SEQUENCE DESCRIPTION: SEQ ID NO: 163:

```
Gly   Gly   Xaa   Gly   Gly   Asn   Gly   Asp   Phe
 1                       5
```

( 2 ) INFORMATION FOR SEQ ID NO: 164:

( i ) SEQUENCE CHARACTERISTICS:
      ( A ) LENGTH: 9 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:
          Xaa in location 3 is X.

( x i ) SEQUENCE DESCRIPTION: SEQ ID NO: 164:

```
Gly   Gly   Xaa   Gly   Gly   Arg   Gly   Asp   Phe
 1                       5
```

( 2 ) INFORMATION FOR SEQ ID NO: 165:

( i ) SEQUENCE CHARACTERISTICS:
      ( A ) LENGTH: 9 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:
          Xaa in location 6 is X.

( x i ) SEQUENCE DESCRIPTION: SEQ ID NO: 165:

```
Gly   Gly   Gly   Gly   Gly   Xaa   Gly   Asp   Phe
 1                       5
```